United States Patent
Gallagher, Jr. et al.

(10) Patent No.: US 7,666,875 B2
(45) Date of Patent: Feb. 23, 2010

(54) HYDANTOIN COMPOUNDS

(75) Inventors: Brian M. Gallagher, Jr., Merrimac, MA (US); Eric Carlson, Merrimack, NH (US); Qian Chen, Methuen, MA (US); Heather Davis, Haverhill, MA (US); Shawn Schiller, Haverhill, MA (US); Christina Shaffer, Litchfield, NH (US); Mark Spyvee, Hampstead, NH (US); Nancy Wong, North Andover, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 11/441,950

(22) Filed: May 26, 2006

(65) Prior Publication Data

US 2006/0270696 A1 Nov. 30, 2006

Related U.S. Application Data

(60) Provisional application No. 60/685,594, filed on May 27, 2005.

(51) Int. Cl.
*A61K 31/438* (2006.01)
*C07D 471/10* (2006.01)

(52) U.S. Cl. .................. 514/278; 546/20; 544/124; 514/231.5

(58) Field of Classification Search .............. 514/278, 514/231.5; 546/20; 544/124
See application file for complete search history.

(56) References Cited

FOREIGN PATENT DOCUMENTS

| EP | 1 619 193 A1 | 1/2006 |
|---|---|---|
| WO | WO 2004/092169 | * 10/2004 |
| WO | WO 2005/023810 A1 | 3/2005 |
| WO | WO 2006/000096 A1 | 1/2006 |

OTHER PUBLICATIONS

Balashov et al. "CCR5+ and CXCR3+ T cells are increased in multiple sclerosis and their Ilgands MIP-1α and IP-10 are expressed in demyelinating brain lesions" *Proc. Natl. Acad. Sci. USA* 96:6873-6878 (1999).

Bleicher et al. "Parallel Solution- and Solid-Phase Synthesis of Spirohydantoin Derivatives as Neurokinin-1 Receptor Ligands" *Bioorganic &Medicinal Chemistry Letters* 12:2519-2522 (2002).
International Search Report and Written Opinion for PCT/US2006/020848; date of mailing Nov. 24, 2006.
Sellebjerg et al. "CCR5 Δ 32, matrix matealloproteinase-9 and disease activity in multiple sclerosis" *Journal of Neuroimmunology* 102:98-106 (2000).
Szabo S J et al. A novel transcription factor, T-bet, directs Th1 lineage commitment. Cell (Mar. 17, 2000), vol. 100, pp. 655-669.
Gerli R et al. In vivo activated T cells in rheumatoid synovitis. Analysis of Th1- and Th2-type cytokine production at clonal level in different stages of disease. Clinical and Experimental Immunology (2002), vol. 129, pp. 549-555.
Skapenko A et al. The role of the T cell in autoimmune inflammation. Arthritis Research & Therapy (Mar. 2005), vol. 7, supp. 2, pp. S4-S14.
Dunn S E et al. Isoprenoids determine Th1/Th2 fate in pathogenic T cells, providing a mechanism of modulation of autoimmunity by atorvastatin. The Journal of Experimental Medicine (Feb. 20, 2006), vol. 203, No. 2, pp. 401-412.
International Preliminary Report on Patentability and Written Opinion for PCT/US2006/020848; date of mailing Dec. 27, 2007.
Weigmann B and Neurath N. T-bet as a possible therapeutic target in autoimmune disease. Expert Opin. Ther. Targets 6, 619 (2002) (abstract only).
Neurath M et al. The Transcription Factor T-bet Regulates Mucosal T Cell Activation in Experimental Colitis and Crohn's Disease. J. Exp. Med. 195, 1129 (2002).
Peng S et al. T-bet regulates IgG class switching and pathogenic autoantibody production. Proc. Natl. Acad. Sci. USA 99, 5545 (2002).
Juedes A et al. T-bet Controls Autoaggressive CD8 Lymphocyte Responses in Type 1 Diabetes, J. Exp. Med. 199, 1153 (2004).
Bettelli E et al. Loss of T-bet, But Not STAT1, prevents the Development of Experimental Autoimmune Encephalomyelitis. J. Exp. Med. 200, 79 (2004).
Buono C et al. T-bet deficiency reduces atherosclerosis and alters plaque antigen-specific immune responses. Proc. Natl. Acad. Sci. USA 102, 1596 (Feb. 2005).

* cited by examiner

*Primary Examiner*—Charanjit S Aulakh
(74) *Attorney, Agent, or Firm*—Myers Bigel Sibley & Sajovec, P.A.

(57) ABSTRACT

The invention relates to the use of hydantoin compounds useful for treating or preventing autoimmune disorders. The present invention also provides compositions and uses thereof.

30 Claims, No Drawings

HYDANTOIN COMPOUNDS

CROSS-REFERENCE TO RELATED APPLICATIONS

The present application claims priority to U.S. provisional patent application Ser. No. 60/685,594, filed May 27, 2005, the entirety of which is hereby incorporated herein by reference.

BACKGROUND OF THE INVENTION

Upon encountering antigen, naive CD4+ T helper precursor (Thp) cells are differentiated into two distinct subsets, Type 1 T helper (Th1) and Type 2 T helper (Th2). These differentiated Th cells are defined both by their distinct functional abilities and by unique cytokine profiles. Specifically, Th1 cells produce interferon-gamma, interleukin (IL)-2, and tumor necrosis factor (TNF)-beta, which activate macrophages and are responsible for cell-mediated immunity and phagocyte-dependent protective responses. In contrast, Th2 cells are known to produce IL-4, IL-5, IL-6, IL-9, IL-10 and IL-13, which are responsible for strong antibody production, eosinophil activation, and inhibition of several macrophage functions, thus providing phagocyte-independent protective responses. Accordingly, Th1 and Th2 cells are associated with different immunopathological responses.

In addition, the development of each type of Th cell is mediated by a different cytokine pathway. Specifically, it has been shown that IL-4 promotes Th2 differentiation and simultaneously blocks Th1 development. In contrast, IL-12, IL-18 and IFN-gamma are the cytokines critical for the development of Th1 cells. Accordingly, the cytokines themselves form a positive and negative feedback system that drives Th polarization and keeps a balance between Th1 and Th2.

Th1 cells are involved in the pathogenesis of a variety of organ-specific autoimmune disorders, Crohn's disease, *Helicobacter pylori*-induced peptic ulcer, acute kidney allograft rejection, and unexplained recurrent abortions. In contrast, allergen-specific Th2 responses are responsible for atopic disorders in genetically susceptible individuals. Moreover, Th2 responses against still unknown antigens predominate in Omenn's syndrome, idiopathic pulmonary fibrosis, and progressive systemic sclerosis.

There remains a high unmet medical need to develop new therapeutic treatments that are useful in treating the various conditions associated with imbalanced Th1/Th2 cellular differentiation. Accordingly, the Th1/Th2 paradigm provides the rationale for the development of strategies for the therapy of allergic and autoimmune disorders.

SUMMARY OF THE INVENTION

As described herein, the present invention provides compounds of formula I:

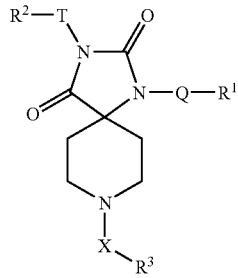

I wherein:

Q is methylene or ethylene;

$R^1$ is hydrogen, $C_{1-6}$ alkyl, $C_{1-6}$ alkoxy, $C_{1-8}$ hydroxyalkyl, $(C_{1-3}$ alkoxy$)C_{1-3}$ alkyl, $C_{1-3}$ alkylthio, $C_{2-5}$ alkenyl, phenyl, indolyl, quinolyl, pyrazolyl, pyrrolyl, pyridinyl, furyl, N-methylbenzotriazolyl, hydroxyethyl, propenyl, (ethoxycarbonyl)propyl, or tetrahydropyranyloxybutyl, wherein $R^1$ has 0-3 substituents independently selected from cyano, methyl, methoxy, pyrazolyl, furyl, hydroxyethyl, acetamido, pyrrolyl, and propenyl, and 0-1 substituents selected from benzotriazolyl, N-methyl-benzotriazolyl, and benzo[d][1,3]dioxolyl, or Q and R' taken together are hydrogen;

T is —C(═O)—, —CH$_2$—, —CH$_2$—CH$_2$—, —CH═CH— (cis or trans), propenylene, —CH═CH—CH$_2$— (cis or trans), —CH$_2$—CH═CH— (cis or trans), ethynylene, or vinylene;

$R^2$ is selected from $C_{2-6}$ alkenyl, $C_{1-12}$ alkyl, phenyl, phenoxy, benzyloxy, naphthyl, furyl, isoquinolinyl, quinolyl, indolyl, pyrazolyl, thiazolyl, anthryl, and benzothienyl, wherein $R^2$ is substituted with 0 to 3 substituents, wherein between 0 and 3 substituents are independently selected from methyl, methoxy, trifluoromethoxy, hydroxyl, hydroxymethyl, fluoro, chloro, bromo, dimethylamino, t-butyl, and isobutoxy; and between 0 and 1 substituents are selected from phenyl, pyridyl, pyrazolyl, furyl, benzoyl, pyrrolyl, pyridinyl, naphthyl, phenoxy, benzo[d][1,3]dioxolyl, cyclohexyl, cyclopentyl, cyclobutyl, and cyclopropyl;

X is a covalent bond, methylene, ethylene, or propenylene; and $R^3$ is selected from phenyl, biphenylyl, thiophenyl, bithiophenylyl, diphenylmethanyl, triazolyl, thienyl, benzofuryl, phenanthryl, anthryl, fluorenyl, acenaphthyl, pyrenyl, indanyl, adamantyl, carbazolyl, N-methylcarbazolyl, indolyl, pyrrolidinyl, quinolyl, pyrrolyl, naphthyl, methylnaphthyl, methoxynaphthyl, dimethylthienyl, benzothiadiazolyl, benzimidazolyl, benzothienyl, benzodioxanyl, benzodioxepinyl, benzodioxocinyl, and benzo[d][1,3]dioxolyl, wherein $R^3$ is substituted with 0 to 5 substituents, wherein between 0 and 5 substituents are independently selected from methyl, trifluoromethyl, methoxy, trifluoromethoxy, chloro, fluoro, bromo, ethenyl, ethoxy, ethyl, isopropyl, t-butyl, propyloxy, amino, dimethylamino, methylamino, allyloxy, (methyl)(phenyl)amino, methanesulfonyl, t-butoxycarbonylmethylamino, t-butoxycarbonyl, boronic acid moiety, and methylcarbonylamino; and wherein between 0 and 2 substituents are independently selected from phenyl, phenoxy, benzyl, benzyloxy, benzoyl, (methyl)(phenyl)amino, N-morpholinyl, piperidyl, pyrrolidinyl, thienyl, furyl, hydroxyphenyl, naphthyl, methylnaphthyl, methoxynaphthyl, dimethylthienyl, benzimidazolyl, indolyl, isoquinolinyl, quinolinyl, dibenzofuryl, benzofuranyl, biphenylyl, and benzo[d][1,3]dioxolyl;

or a pharmaceutically acceptable salt, $C_{1-6}$ alkyl ester or amide, or $C_{2-6}$ alkenyl ester or amide thereof.

According to another embodiment, the present invention provides a compound of formula II:

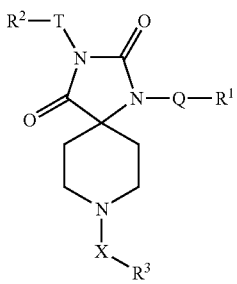

wherein:

Q is a straight or branched, saturated or unsaturated C<sub>1-6</sub> alkylene chain;

$R^1$ is an optionally substituted phenyl ring or an optionally substituted 6-membered heteroaryl ring having 1-2 nitrogens;

T is a straight or branched, saturated or unsaturated $C_{1-6}$ alkylene chain;

$R^2$ is an optionally substituted phenyl or naphthyl ring, or an optionally substituted 5-membered heteroaryl ring having 1-3 heteroatoms independently selected from nitrogen, oxygen, and sulfur;

X is a straight or branched, saturated or unsaturated $C_{1-4}$ alkylene chain; and $R^3$ is phenyl, naphthyl, quinolinyl, isoquinolinyl, indolyl, benzimidazolyl, benzofuranyl, benzothiophenyl, thienyl, furyl, pyrazolyl, triazolyl, isoxazolyl, or thiazolyl; wherein $R^3$ is optionally substituted with pyrrolidinyl, morpholinyl, piperidinyl, furyl, thienyl, phenyl, —N(Me)phenyl, —N(Me)$_2$, —OMe, —OEt, -Me, t-butyl, pyridyl, —NHMe, —C(=O)OMe, —C(=O)OCH$_2$phenyl, —NH$_2$, —OH, —OCH$_2$CH$_2$OH, —OCF$_3$, —CF$_3$, or —SO$_2$phenyl;

or a pharmaceutically acceptable salt, $C_{1-6}$ alkyl ester or amide, or $C_{2-6}$ alkenyl ester or amide thereof.

In certain embodiments, the present invention provides a compound of formula III:

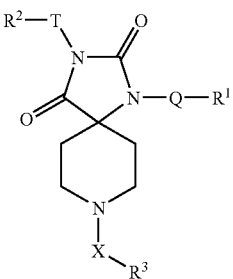

wherein:

Q is —CH$_2$O—, —(CH$_2$)$_2$O—, —(CH$_2$)$_3$O—, —(CH$_2$)$_4$O—, —(CH$_2$)$_6$O—, —CH$_2$OCH$_2$—, —(CH$_2$)$_2$OCH$_2$—, —(CH$_2$)$_3$OCH$_2$—, —(CH$_2$)$_4$OCH$_2$—, —(CH$_2$)$_6$OCH$_2$—, —(CH$_2$)$_2$S—, —CH$_2$—, —(CH$_2$)$_2$—, —(CH$_2$)$_3$—, —(CH$_2$)$_4$—, —CH$_2$CH=CH—, —CH$_2$C(=CH$_2$)CH$_2$—, —CH$_2$CH=CHCH$_2$—, —CH$_2$CH(CH$_3$)CH$_2$—, —CH$_2$C(=O)OCH$_2$—, —CH$_2$CH=C(CH$_3$)CH$_2$CH$_2$CH=C(CH$_3$)—, —CH$_2$C≡CCH$_2$CH$_2$—, —CH$_2$C(=O)CH$_2$—, —(CH$_2$)$_4$C(=O)OCH$_2$CH$_2$—, —(CH$_2$)$_5$C(=O)OCH$_2$CH$_2$—, —(CH$_2$)$_6$C(=O)OCH$_2$CH$_2$—CH$_2$C(=O)N(Et)CH$_2$CH$_2$—, or —CH$_2$CH$_2$N(CH$_3$)CH$_2$—;

$R^1$ is CN, pyridyl, thiazolyl, tetrahydrofuranyl, tetrahydro-2H-pyranyl, phenyl, isoxazolyl, pyrrolyl, benztriazolyl, cyclohexyl, cyclopropyl, or thienyl;

T is —CH$_2$O—, —(CH$_2$)$_2$O—, —(CH$_2$)$_3$O—, —(CH$_2$)$_4$O—, —(CH$_2$)$_6$O—, —CH$_2$OCH$_2$—, —(CH$_2$)$_2$OCH$_2$—, —(CH$_2$)$_3$OCH$_2$—, —(CH$_2$)$_4$OCH$_2$—, —(CH$_2$)$_6$OCH$_2$—, —(CH$_2$)$_2$S—, —CH$_2$—, —(CH$_2$)$_2$—, —(CH$_2$)$_3$—, —(CH$_2$)$_4$—, —CH$_2$CH=CH—, —CH$_2$CH=CHCH$_2$—, —CH$_2$C(=CH$_2$)CH$_2$—, —CH$_2$CH$_2$CH=CH—, —CH$_2$CH(CH$_3$)CH$_2$—, —CH$_2$C(=O)OCH$_2$—, —CH$_2$CH=C(CH$_3$)CH$_2$CH$_2$CH=C(CH$_3$)—, —CH$_2$C≡C— or —CH$_2$C≡CCH$_2$CH$_2$—;

$R^2$ is optionally substituted phenyl, naphthyl, quinolinyl, phthalimidyl, isoquinolinyl, indolyl, thienyl, furyl, isoxazolyl, or thiazolyl;

X is —CH$_2$—, —CH$_2$CH$_2$—, —CH$_2$C≡C—, —CH$_2$CH=CH—, —CH$_2$C(CH$_3$)—CH— or —CH$_2$CH(CH$_3$)—; and $R^3$ is phenyl or naphthyl; wherein $R^3$ is optionally substituted with pyrrolidinyl, morpholinyl, piperidinyl, furyl, thienyl, phenyl, —N(Me)phenyl, —N(Me)$_2$, —OMe, —OEt, -Me, t-butyl, pyridyl, —NHMe, —C(=O)OMe, —C(=O)OCH$_2$phenyl, —NH$_2$, —OH, —OCH$_2$CH$_2$OH, —OCF$_3$, —CF$_3$, or —SO$_2$phenyl;

or a pharmaceutically acceptable salt, $C_{1-6}$ alkyl ester or amide, or $C_{2-6}$ alkenyl ester or amide thereof.

In other embodiments, the present invention provides a compound of formula IV:

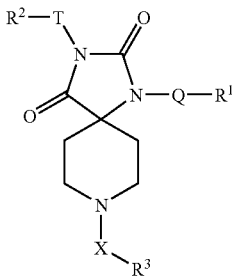

wherein:

Q is —CH$_2$O—, —(CH$_2$)$_2$O—, —(CH$_2$)$_3$O—, —(CH$_2$)$_4$O—, —(CH$_2$)$_6$O—, —CH$_2$OCH$_2$—, —(CH$_2$)$_2$OCH$_2$—, —(CH$_2$)$_3$OCH$_2$—, —(CH$_2$)$_4$OCH$_2$—, —(CH$_2$)$_6$OCH$_2$—, or —(CH$_2$)$_2$S—;

$R^1$ is hydrogen;

T is —CH$_2$—, —(CH$_2$)$_2$—, —(CH$_2$)$_3$—, —(CH$_2$)$_4$—, —CH$_2$CH=CH—, —CH$_2$CH=CHCH$_2$—, —CH$_2$C(=CH$_2$)CH$_2$—, —CH$_2$CH$_2$CH=CH—, —CH$_2$CH(CH$_3$)CH$_2$—, —CH$_2$C(=O)OCH$_2$—, —CH$_2$CH=C(CH$_3$)CH$_2$CH$_2$CH=C(CH$_3$)—, —CH$_2$C≡C— or —CH$_2$C≡CCH$_2$CH$_2$—;

$R^2$ is optionally substituted phenyl or naphthyl;

X is —CH$_2$—; and $R^3$ is a phenyl or naphthyl ring; wherein $R^3$ is optionally substituted with pyrrolidinyl, morpholinyl, piperidinyl, furyl, thienyl, phenyl, —N(Me)phenyl, —N(Me)$_2$, —OMe, —OEt, -Me, t-butyl, pyridyl, —NHMe, —C(=O)OMe, —C(=O)OCH$_2$phenyl, —NH$_2$, —OH, —OCH$_2$CH$_2$OH, —OCF$_3$, —CF$_3$, or —SO$_2$phenyl;

or a pharmaceutically acceptable salt, C$_{1-6}$ alkyl ester or amide, or C$_{2-6}$ alkenyl ester or amide thereof.

In other embodiments, the present invention provides a pharmaceutical composition comprising a compound of formula I, II, III, or IV, or subsets and examples thereof as defined herein. In certain embodiments, the pharmaceutical composition is useful for treating rheumatoid arthritis or multiple sclerosis.

According to another aspect, the present invention provides a method for treating an autoimmune disease in a patient, comprising administering to the patient a pharmaceutical composition comprising a compound of formula I, II, III, or IV, or subsets and examples thereof as defined herein. In certain embodiments, the autoimmune disease is rheumatoid arthritis or multiple sclerosis.

The present invention also provides the use of a compound of formula I, II, III, or IV, or subsets and examples thereof as defined herein, in the manufacture of a medicament useful for treating an autoimmune disease, such as rheumatoid arthritis or multiple sclerosis.

DETAILED DESCRIPTION OF CERTAIN EMBODIMENTS OF THE INVENTION

A. Definitions

Compounds of this invention include those described generally above, and are further illustrated by the embodiments, sub-embodiments, and species disclosed herein. As used herein, the following definitions shall apply unless otherwise indicated.

As described herein, compounds of the invention may optionally be substituted with one or more substituents, such as are illustrated generally above, or as exemplified by particular classes, subclasses, and species of the invention. In general, the term "substituted" refers to the replacement of hydrogen radicals in a given structure with the radical of a specified substituent. Unless otherwise indicated, a substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "alkyl" or "alkyl group," as used herein, means a straight-chain (i.e., unbranched), branched, or cyclic hydrocarbon chain that is completely saturated. In certain embodiments, alkyl groups contain 1-6 carbon atoms. In still other embodiments, alkyl groups contain 2-5 carbon atoms, and in yet other embodiments alkyl groups contain 1-4, 2-4, or 1-3 carbon atoms. In certain embodiments, the term "alkyl" or "alkyl group" refers to a cycloalkyl group, also known as carbocyclyl. Exemplary C$_{1-6}$ alkyl groups include methyl, ethyl, propyl, isopropyl, cyclopropyl, cyclopropylmethyl, cyclopropylethyl, cyclopropylpropyl, butyl, isobutyl, cyclobutyl, cyclobutylmethyl, cyclobutylethyl, pentyl, isopentyl, neopentyl, cyclopentyl, hexyl, isohexyl, and cyclohexyl.

The term "alkenyl" or "alkenyl group," as used herein, refers to a straight-chain (i.e., unbranched), branched, or cyclic hydrocarbon chain that has one or more double bonds. In certain embodiments, alkenyl groups contain 2-6 carbon atoms. In still other embodiments, alkenyl groups contain 2-5 carbon atoms, and in yet other embodiments alkenyl groups contain 2-4 carbon atoms. In other embodiments, the term "alkenyl" or "alkenyl group" refers to a cycloalkenyl group. Exemplary C$_{2-6}$ alkenyl groups include —CH=CH$_2$, —CH$_2$CH=CH$_2$ (also referred to as allyl), —CH=CHCH$_3$, —CH$_2$CH$_2$CH=CH$_2$, —CH$_2$CH=CHCH$_3$, —CH=CH$_2$CH$_2$CH$_3$, —CH$_2$CH$_2$CH$_2$CH=CH$_2$, —CH=CHCH$_2$CH$_2$CH$_3$, —CH$_2$CH=CHCH$_2$CH$_3$, —CH$_2$CH$_2$CH=CHCH$_3$, —CH$_2$CH$_2$CH$_2$CH$_2$CH=CH$_2$, —CH=CHCH$_2$CH$_2$CH$_2$CH$_3$, —CH$_2$CH=CHCH$_2$CH$_2$CH$_3$, —CH$_2$CH$_2$CH=CHCH$_2$CH$_3$, —CH$_2$CH$_2$CH$_2$CH=CHCH$_3$, —CH$_2$CH$_2$CH$_2$CH$_2$CH=CH$_2$, cyclobutenyl, cyclobutenemethyl, cyclopentenyl, cyclopentadienyl, cyclopentenemethyl, cyclohexenyl, and cyclohexadienyl.

The term "alkynyl" or "alkynyl group," as used herein, refers to a straight-chain (i.e., unbranched) or branched hydrocarbon chain that has one or more triple bonds. In certain embodiments, alkynyl groups contain 2-6 carbon atoms. In still other embodiments, alkynyl groups contain 2-5 carbon atoms, and in yet other embodiments alkynyl groups contain 2-4 or 2-3 carbon atoms. In other embodiments, the term "alkynyl" or "alkynyl group" refers to a cycloalkynyl group. Exemplary C$_{2-6}$ alkynyl groups include —C≡CH, —CH$_2$C≡CH (also referred to as vinyl), —C≡CCH$_3$, —CH$_2$CH$_2$C≡CH, —CH$_2$C≡CCH$_3$, —C≡CHCH$_2$CH$_3$, —CH$_2$CH$_2$CH$_2$C≡CH, —C—CCH$_2$CH$_2$CH$_3$, —CH$_2$C≡CCH$_2$CH$_3$, —CH$_2$CH$_2$C≡CCH$_3$, —CH$_2$CH$_2$CH$_2$CH$_2$C≡CH, —C—CCH$_2$CH$_2$CH$_2$CH$_3$, —CH$_2$C≡CCH$_2$CH$_2$CH$_3$, —CH$_2$CH$_2$C≡CCH$_2$CH$_3$, —CH$_2$CH$_2$CH$_2$C≡CCH$_3$, cyclobutynyl, cyclobutynemethyl, cyclopentynyl, cyclopentynemethyl, and cyclohexynyl.

The term "alkoxy", or "alkylthio", as used herein, refers to an alkyl group, as previously defined, attached to the principal carbon chain through an oxygen ("alkoxy") or sulfur ("alkylthio") atom.

As used herein, the term "alkylene" refers to a straight or branched, saturated or unsaturated bivalent hydrocarbon chain. In certain embodiments, alkylene groups contain 1-6 carbon atoms. In other embodiments, alkylene groups contain 2-5, 1-4, 2-4, 1-3, or 2-3 carbon atoms. Exemplary alkylene groups include methylene, ethylene, and propylene. In certain embodiments, alkylene groups have a double bond, referred to herein as "alkenylene." In other embodiments, alkylene groups have a triple bond, referred to herein as "alkynylene."

As used herein the terms methylene and ethylene refer to the bivalent moieties —CH$_2$— and —CH$_2$CH$_2$—, respectively. The term propenylene refers to the bivalent moieties —CH=CHCH$_2$— and —CH$_2$CH=CH—, where each propenylene group is in the cis or trans configuration. In certain embodiments, a propenylene group can be in the trans configuration.

As used herein, the term "C$_{1-6}$ alkyl ester or amide" refers to a C$_{1-6}$ alkyl ester or a C$_{1-6}$ alkyl amide where each C$_{1-6}$ alkyl group is as defined above. Such C$_{1-6}$ alkyl ester groups are of the formula ($C_{1-6}$ alkyl)OC(=O)— or ($C_{1-6}$ alkyl)C(=O)O—. Such $C_{1-6}$ alkyl amide groups are of the formula ($C_{1-6}$ alkyl)NHC(=O)— or ($C_{1-6}$ alkyl)C(=O)NH—.

As used herein, the term "$C_{2-6}$ alkenyl ester or amide" refers to a $C_{2-6}$ alkenyl ester or a $C_{2-6}$ alkenyl amide where each $C_{2-6}$ alkenyl group is as defined above. Such $C_{2-6}$ alkenyl ester groups are of the formula ($C_{2-6}$ alkenyl)OC(=O)— or ($C_{2-6}$ alkenyl)C(=O)O—. Such $C_{2-6}$ alkenyl amide groups are of the formula ($C_{2-6}$ alkenyl)NHC(=O)— or ($C_{2-6}$ alkenyl)C(=O)NH—.

As used herein, the term "6-membered heteroaryl ring having 1-2 nitrogens" refers to a monocyclic, aromatic ring containing 1-2 nitrogen atoms. Such rings include pyridin-2-yl, pyridin-3-yl, pyridin-4-yl, pyrimidin-2-yl, pyrimidin-4-yl, pyrimidin-5-yl, pyridazin-3-yl, pyrazin-3-yl, and pyrazin-4-yl.

As used herein, the term "5-membered heteroaryl ring having 1-3 heteroatoms independently selected from nitrogen, oxygen, or sulfur" refers to a monocyclic, aromatic ring containing 1-3 heteroatoms independently selected from nitrogen, oxygen, or sulfur. Such rings include furan-2-yl, furan-3-yl, N-imidazolyl, imidazol-2-yl, imidazol-4-yl, imidazol-5-yl, isoxazol-3-yl, isoxazol-4-yl, isoxazol-5-yl, oxadiazol-2-yl, oxadiazol-5-yl, oxazol-2-yl, oxazol-4-yl, oxazol-5-yl, pyrrol-1-yl, pyrrol-2-yl, pyrrol-3-yl, pyridin-2-yl, pyridin-3-yl, pyridin-4-yl, pyrimidin-2-yl, pyrimidin-4-yl, pyrimidin-5-yl, pyridazin-3-yl, thiazol-2-yl, thiazol-4-yl, thiazol-5-yl, tetrazol-5-yl, triazol-2-yl, triazol-5-yl, thien-2-yl, and thien-3-yl.

Unless indicated otherwise, nomenclature used to describe chemical groups or moieties as used herein follow the convenion where, reading the name from left to right, the point of attachment to the rest of the molecule is at the right-hand side of the named fragment. For example, the group "(ethoxycarbonyl)propyl," is attached to the rest of the molecule at the propyl end. Further examples include hydroxyethyl, where the point of attachment is at the ethyl end, and acetamido, where the point of attachment is at the amide end.

Unless indicated otherwise, a chemical group described herein by its chemical formula, including a bond moiety indicated by a "-," it will be understood that the chemical group is attached to the rest of the molecule at the indicated "-." For example, the group —SO$_2$phenyl is attached to the rest of the molecule at the left-hand side via the indicated bond. Where a bivalent group is described by its chemical formula, including two terminal bond moieties indicated by "-," it will be understood that the attachment is read from left to right. By way of example, when Q is —CH$_2$O—, Q is attached to the nitrogen of the hydantoin core at the left-hand side methylene and Q is attached to R$^1$ at the right-hand side oxygen atom. Similarly, when T is —CH$_2$O—, T is attached to the nitrogen of the hydantoin core at the left-hand side methylene and T is attached to R$^2$ at the right-hand side oxygen atom.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. In certain embodiment, when the —T—R$^2$ group of formula I comprises a double bond, that double bond is in the trans (Z) conformation. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

As used herein, the terms "treatment," "treat," and "treating" refer to reversing, alleviating, delaying the onset of, or inhibiting the progress of a disease or disorder as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

B. Compounds

In one embodiment, the present invention provides a compound of formula I:

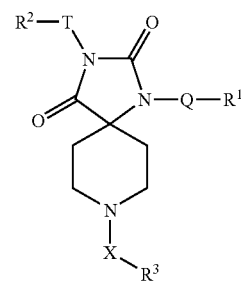

wherein:

Q is methylene or ethylene;

R$^1$ is hydrogen, $C_{1-6}$ alkyl, $C_{1-6}$ alkoxy, $C_{1-8}$ hydroxyalkyl, ($C_{1-3}$ alkoxy)$C_{1-3}$ alkyl, $C_{1-3}$ alkylthio, $C_{2-5}$ alkenyl, phenyl, indolyl, quinolyl, pyrazolyl, pyrrolyl, pyridinyl, furyl, N-methylbenzotriazolyl, hydroxyethyl, propenyl, (ethoxycarbonyl)propyl, or tetrahydropyranyloxybutyl,
 wherein R$^1$ has 0-3 substituents independently selected from cyano, methyl, methoxy, pyrazolyl, furyl, hydroxyethyl, acetamido, pyrrolyl, and propenyl, and 0-1 substituents selected from benzotriazolyl, N-methyl-benzotriazolyl, and benzo[d][1,3]dioxolyl,
 or Q and R' taken together are hydrogen;

T is —C(=O)—, —CH$_2$—, —CH$_2$—CH$_2$—, —CH=CH— (cis or trans), propenylene, —CH=CH—CH$_2$— (cis or trans), —CH$_2$—CH=CH— (cis or trans), ethynylene, or vinylene;

R$^2$ is selected from $C_{2-6}$ alkenyl, $C_{1-12}$ alkyl, phenyl, phenoxy, benzyloxy, naphthyl, furyl, isoquinolinyl, quinolyl, indolyl, pyrazolyl, thiazolyl, anthryl, and benzothienyl,
 wherein R$^2$ is substituted with 0 to 3 substituents, wherein between 0 and 3 substituents are independently selected from methyl, methoxy, trifluoromethoxy, hydroxyl, hydroxymethyl, fluoro, chloro, bromo, dimethylamino, t-butyl, and isobutoxy; and between 0 and 1 substituents are selected from phenyl, pyridyl, pyrazolyl, furyl, benzoyl, pyrrolyl, pyridinyl, naphthyl, phenoxy, benzo[d] [1,3]dioxolyl, cyclohexyl, cyclopentyl, cyclobutyl, and cyclopropyl;

X is a covalent bond, methylene, ethylene, or propenylene; and $R^3$ is selected from phenyl, biphenylyl, thiophenyl, bithiophenylyl, diphenylmethanyl, triazolyl, thienyl, benzofuryl, phenanthryl, anthryl, fluorenyl, acenaphthyl, pyrenyl, indanyl, adamantyl, carbazolyl, N-methylcarbazolyl, indolyl, pyrrolidinyl, quinolyl, pyrrolyl, naphthyl, methylnaphthyl, methoxynaphthyl, dimethylthienyl, benzothiadiazolyl, benzimidazolyl, benzothienyl, benzodioxanyl, benzodioxepinyl, benzodioxocinyl, and benzo[d][1,3]dioxolyl, wherein $R^3$ is substituted with 0 to 5 substituents, wherein between 0 and 5 substituents are independently selected from methyl, trifluoromethyl, methoxy, trifluoromethoxy, chloro, fluoro, bromo, ethenyl, ethoxy, ethyl, isopropyl, t-butyl, propyloxy, amino, dimethylamino, methylamino, allyloxy, (methyl)(phenyl) amino, methanesulfonyl, t-butoxycarbonylmethylamino, t-butoxycarbonyl, boronic acid moiety, and methylcarbonylamino; and wherein between 0 and 2 substituents are independently selected from phenyl, phenoxy, benzyl, benzyloxy, benzoyl, (methyl)(phenyl) amino, N-morpholinyl, piperidyl, pyrrolidinyl, thienyl, furyl, hydroxyphenyl, naphthyl, methylnaphthyl, methoxynaphthyl, dimethylthienyl, benzimidazolyl, indolyl, isoquinolinyl, quinolinyl, dibenzofuranyl, benzofuranyl, biphenylyl, and benzo[d][1,3]dioxolyl;

or a pharmaceutically acceptable salt, $C_{1-6}$ alkyl ester or amide, or $C_{2-6}$ alkenyl ester or amide thereof.

In certain embodiments, $R^1$ is hydrogen, methyl, hydroxymethyl, methoxy, methoxymethyl, methylthio, isopropyl, phenyl, indolyl, pyrazolyl, pyrrolyl, pyridinyl, furyl, N-methylbenxotriazolyl, or hydroxyethyl; and wherein $R^1$ has 0 to 2 substituents. In other embodiments, $R^1$ is methoxymethyl, hydroxymethyl, or methyl.

In other embodiments, $R^1$ is hydrogen, $C_{1-4}$ alkyl, $C_{1-4}$ hydroxyalkyl, ($C_{1-3}$ alkoxy)$C_{1-3}$ alkyl, $C_{1-3}$ alkylthio, $C_{2-5}$ alkenyl, hydroxyethyl, propenyl, or (ethoxycarbonyl)propyl; wherein $R^1$ has 0-3 substituents independently selected from cyano, methyl, methoxy, hydroxyethyl, acetamido, and propenyl.

In still other embodiments, $R^1$ is hydrogen, $C_{1-4}$ alkyl, $C_{1-4}$ hydroxyalkyl, ($C_{1-3}$ alkoxy)$C_{1-3}$ alkyl, $C_{1-3}$ alkylthio, $C_{2-5}$ alkenyl, indolyl, quinolyl, pyrazolyl, pyrrolyl, pyridinyl, furyl, N-methylbenzotriazolyl, hydroxyethyl, propenyl, (ethoxycarbonyl)propyl, or tetrahydropyranyloxybutyl; wherein $R^1$ has 0-3 substituents independently selected from cyano, methyl, methoxy, pyrazolyl, furyl, hydroxyethyl, acetamido, pyrrolyl, and propenyl, and 0-1 substituents selected from benzotriazolyl, N-methyl-benzotriazolyl, and benzo[d][1,3]dioxolyl.

In certain embodiments, —Q—$R^1$ taken together form methyl, methoxyethyl, 4-(pyrazol-1-yl)phenylmethyl, ethyl, hydroxyethyl, methoxymethyl, 3-(pyrrol-1-yl)phenylmethyl, N-methylbenzotriazolylmethyl, or pyridin-4-ylmethyl.

According to one embodiment, the present invention provides a compound of formula I wherein $R^2$ is substituted with between 0 and 3 substituents. According to another embodiment, $R^2$ is selected from $C_{2-4}$ alkenyl, phenyl, naphthyl, furyl, isoquinolinyl, quinolyl, indolyl, pyrazolyl, thiazolyl, and benzothienyl, wherein $R^2$ is substituted with 0 to 2 groups; wherein between 0 and 2 substituents are independently selected from methyl, methoxy, trifluoromethoxy, hydroxyl, fluoro, and hydroxymethyl. According to another embodiment, $R^2$ is a phenyl group with between 0 and 3 substituents independently selected from methoxy, trifluoromethoxy, fluoro, and methyl.

It will be appreciated that substituents indicated for the $R^2$ group of compounds of formula I are also intended to be suitable substituents for the $R^2$ group of compounds of formulae II, III, and IV.

In other embodiments, X is methylene. In still other embodiments, X is methylene, ethylene, or propenylene. In certain embodiments, X is —CH$_2$CH=CH— in the trans configuration.

In certain embodiments, Q is ethylene.

According to another aspect, T is —CH$_2$—, —CH=CH— (cis or trans), —CH=CH—CH$_2$-(cis or trans), —CH$_2$—CH=CH— (cis or trans), ethynylene, or vinylene. In other embodiments, T is methylene, —CH=CH—CH$_2$— (trans), or —CH$_2$—CH=CH— (trans).

In certain embodiments, the $R^3$ group of formula I is substituted with between 0 and 4 substituents, or 0-3, 1-2, or 2-3 substituents, as defined above. In other embodiments, $R^3$ is selected from phenyl, biphenylyl, thiophenyl, bithiophenylyl, triazolyl, thienyl, benzofuryl, phenanthryl, indolyl, pyrrolidinyl, quinolyl, pyrrolyl, naphthyl, methylnaphthyl, methoxynaphthyl, dimethylthienyl, benzothiadiazolyl, benzimidazolyl, benzothiophenyl, benzodioxanyl, benzodioxepinyl, benzodioxocinyl, and benzo[d][1,3]dioxolyl; wherein $R^3$ is substituted with between 0 and 3 substituents, wherein between 0 and 3 substituents are independently selected from methyl, trifluoromethyl, methoxy, trifluoromethoxy, chloro, fluoro, bromo, ethenyl, ethoxy, ethyl, isopropyl, t-butyl, propyloxy, amino, dimethylamino, methylamino, allyloxy, (methyl)(phenyl)amino, methanesulfonyl, t-butoxycarbonylmethylamino, t-butoxycarbonyl, boronic acid moiety, and methylcarbonylamino; and wherein between 0 and 1 substituents is independently selected from phenyl, phenoxy, benzyl, benzyloxy, benzoyl, (methyl)(phenyl)amino, N-morpholinyl, piperidyl, pyrrolidinyl, thienyl, furyl, hydroxyphenyl, naphthyl, methylnaphthyl, methoxynaphthyl, dimethylthienyl, benzimidazolyl, indolyl, quinolinyl, dibenzofuranyl, benzofuranyl, biphenylyl, and benzo[d][1,3]dioxolyl.

In other embodiments, $R^3$ is phenyl, naphthyl, anthryl, biphenylyl, fluorenyl, or acenapthyl with between 0 and 3 substituents independently selected from fluoro, bromo methyl, methoxy, and hydroxymethyl.

In certain embodiments, $R^3$ is phenyl wherein the phenyl group is substituted according to one of the following substitution patterns: (a) the para position is unsubstituted (i.e., has a hydrogen); (b) the phenyl comprises two substituents in the 3- and 5-positions; and (c) the phenyl has at least two substituents selected from the 2-, 3-, and 5-positions.

It will be appreciated that substituents indicated for the $R^3$ group of compounds of formula I are also intended to be suitable substituents for the $R^3$ group of compounds of formulae II, III, and IV.

According to another aspect of the present invention, the present invention provides a compound of formula I wherein:

$R^1$ is hydrogen, methyl, hydroxymethyl, methoxy, methoxymethyl, methylthio, phenyl, pyrazolyl, pyrrolyl, pyridinyl, furyl, or N-methylbenzotriazolyl; or $R^1$ is phenyl independently substituted with methyl, methoxy, pyrazolyl, furyl; benzotriazolyl, N-methyl-benzotriazolyl, or pyrrolyl;

T is —CH$_2$—, —CH$_2$—CH$_2$—, —CH=CH—CH$_2$— (trans), ethynylene, or allyl;

$R^2$ is selected from phenyl, naphthyl, furyl, quinolyl, indolyl, pyrazolyl, thiazolyl, and benzothienyl, wherein $R^2$ is substituted with 0-2 groups, wherein between 0 and 2 substituents are independently selected from methyl, methoxy, trifluoromethoxy, hydroxyl, and hydroxymethyl; and $R^3$ is selected from phenyl, naphthyl, thienyl, benzofuryl, indolyl, isoquinolinyl, quinolyl, pyridinyl, pyrrolyl, benzothiadiazolyl, and benzimidazolyl, wherein $R^3$ is substituted with between 0 and 2 substituents, wherein between 0 and 2 substituents are independently selected from methyl, trifluoromethyl, methoxy, trifluoromethoxy, chloro, fluoro, bromo, ethenyl, ethoxy, ethyl, dimethylamino, and methylamino.

According to yet another aspect of the present invention, the present invention provides a compound of formula I wherein:

$R^1$ is hydrogen, methyl, hydroxymethyl, methoxy, methoxymethyl, methylthio, phenyl, pyrazolyl, pyrrolyl, pyridinyl, furyl, $C_{1-8}$ hydroxyalkyl, or N-methylbenzotriazolyl;

or $R^1$ is substituted with 0 to 1 substituents selected from methyl, methoxy, pyrazolyl, furyl, pyridinyl, benzotriazolyl, N-methyl-benzotriazolyl, and pyrrolyl;

T is —CH$_2$—, —CH$_2$—CH$_2$—, —CH=CH—CH$_2$— (trans), ethynylene, or allyl;

$R^2$ is selected from phenyl, naphthyl, furyl, quinolyl, indolyl, pyrazolyl, benzo[d][1,3]dioxolyl, thiazolyl, and benzothienyl, wherein $R^2$ is substituted with 0-3 groups, wherein between 0 and 3 substituents are independently selected from methyl, methoxy, trifluoromethoxy, hydroxyl, and hydroxymethyl;

X is methylene;

$R^3$ is selected from phenyl, naphthyl, thienyl, benzofuryl, indolyl, pyrrolidinyl, isoquinolyl, quinolyl, pyrrolyl, benzothiadiazolyl, benzimidazolyl, and benzothiophenyl;

wherein $R^3$ is substituted with between 0 and 2 substituents, wherein between 0 and 2 substituents are independently selected from methyl, trifluoromethyl, methoxy, trifluoromethoxy, chloro, fluoro, bromo, ethenyl, ethoxy, ethyl, dimethylamino, and methylamino.

Exemplary compounds of formula I are set forth in the Examples section and in Tables 1-4, below.

C. Uses, Formulation and Administration

Pharmaceutically Acceptable Compositions

The compounds and compositions described herein are generally useful for the inhibition of Th1 cell formation. In particular, these compounds, and compositions thereof, are useful as inhibitors of T-bet function. Thus, the compounds and compositions of the invention are therefore also particularly suited for the treatment of diseases and disease symptoms that are mediated by Th1 cells and/or T-bet.

In one particular embodiment, the compounds and compositions of the invention are inhibitors of T-bet function, and thus the compounds and compositions are particularly useful for treating or lessening the severity of disease or disease symptoms associated with T-bet.

According to another embodiment, the invention provides a composition comprising a compound of this invention or a pharmaceutically acceptable salt thereof and a pharmaceutically acceptable carrier, adjuvant, or vehicle. The amount of the composition is such that is effective to detectably inhibit and/or lessen T-bet function, in a biological sample or in a patient. Preferably the composition of this invention is formulated for administration to a patient in need of such composition.

The term "detectably inhibit", as used-herein means a measurable change in T-bet function between a sample comprising said compound or composition and T-bet and an equivalent sample comprising T-bet in the absence of said compound or composition.

The term "patient", as used herein, means an animal, preferably a mammal, and most preferably a human.

In certain embodiments, the present invention provides a composition comprising a compound of formula I. In other embodiments, the present invention provides a composition comprising a compound of formula II, III, or IV. In still other embodiments, the present invention provides a composition comprising any compound of Examples 1 through 301. According to another aspect, the present invention provides a composition comprising a compound selected from ER 818561, ER 817135, ER 813508, ER 813509, ER 813493, ER 813510, ER 813511, ER 817118, ER 817137, ER 817119, ER 818573, ER 818567, ER 818550, and ER 813512. According to yet another aspect, the present invention provides a composition comprising a compound selected from ER 813499, ER 813081, ER 813077, ER 818528, ER 818574, ER 813411, ER 813078, ER 813521, ER 817116, ER 813080, ER 813519, ER 813492, ER 813452, ER 813410, and ER 812605. In other embodiments, the present invention provides a composition comprising a compound selected from ER 818568, ER 813091, ER 813075, ER 818562, ER 813096, ER 819695, ER 813092, ER 813082, ER 820087, ER 813079, ER 813089, ER 813529, ER 813414, and ER 813516. In still other embodiments, the present invention provides a composition comprising a compound selected from ER 818558, ER 818559, ER 818560, ER 818554, ER 818535, ER 818564, ER 818524, and ER 817117.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, cyclodextrins, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+($C_{1-4}$ alkyl)$_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, and the particular mode of administration. Preferably, the compositions should be formulated so that a dosage of between 0.01-100 mg/kg body weight/day of the inhibitor can be administered to a patient receiving these compositions. In certain embodiments, the compositions of the present invention provide a dosage of between 0.01 mg and 50 mg is provided. In other embodiments, a dosage of between 0.1 and 25 mg, or between 5 and 40 mg is provided.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

T-bet (T-box expressed in T cells) is a Th1 specific transcription factor that is a key regulator of the Th1/Th2 balance. See S. J. Szabo, et al., *Cell*, 100:655-669 (2000). T-bet is selectively induced in Th1 cells and can transactivate the interferon-gamma gene, induce interferon-gamma production, redirect polarized Th2 cells into the Th1 pathway. T-bet also controls IFN-gamma production in CD8+ T cells, as well as in cells of the innate immune system, e.g., NK cells and dendritic cells. Accordingly, inhibitors of T-bet are therapeutically useful in balancing over-active Th1 responses, and therefore be of value in treating Th1-mediated diseases, such as: IBD (Crohn's Disease), RA, MS, and systemic lupus erythrematosus ("SLE").

According to one embodiment, the invention relates to a method of inhibiting the formation of Th1 cells in a biological sample comprising the step of contacting said biological sample with a compound of this invention, or a composition comprising said compound. In certain embodiments, the invention relates to a method of inhibiting the formation of Th1 cells in a biological sample comprising the step of contacting said biological sample with a compound of any of formulae I, II, III, and IV.

According to another embodiment, the invention relates to a method of inhibiting T-bet activity in a biological sample comprising the step of contacting said biological sample with a compound of this invention, or a composition comprising said compound. According to another embodiment, the invention relates to a method of inhibiting T-bet activity in a biological sample comprising the step of contacting said biological sample with a compound any of formulae I, II, III, and IV.

The term "biological sample", as used herein, includes, without limitation, cell cultures or extracts thereof, biopsied material obtained from a mammal or extracts thereof; and blood, saliva, urine, feces, semen, tears, or other body fluids or extracts thereof.

According to one embodiment, the invention relates to a method of inhibiting the formation of Th1 cells in a patient comprising the step of administering to said patient a compound of this invention, or a composition comprising said compound. In other embodiments, the invention relates to a method of inhibiting the formation of Th1 cells in a patient comprising the step of administering to said patient a compound of any of formulae I, II, III, and IV.

According to another embodiment, the invention relates to a method of inhibiting T-bet activity in a in a patient comprising the step of administering to said patient a compound of this invention, or a composition comprising said compound. According to another embodiment, the invention relates to a method of inhibiting T-bet activity in a in a patient comprising the step of administering to said patient a compound of any of formulae I, II, III, and IV.

According to another embodiment, the invention provides a method for treating or lessening the severity of T-bet-mediated disease or condition in a patient comprising the step of administering to said patient a composition according to the present invention. According to another embodiment, the invention provides a method for treating or lessening the severity of T-bet-mediated disease or condition in a patient comprising the step of administering to said patient a composition comprising a compound of any of formulae I, II, III, and IV.

The term "T-bet mediated disease" or "condition", as used herein, means any disease or other deleterious condition in which T-bet is known to play a role. Accordingly, another embodiment of the present invention relates to treating or lessening the severity of one or more diseases in which T-bet is known to play a role. Specifically, the present invention relates to a method of treating or lessening the severity of an autoimmune disease, wherein said method comprises administering to a patient in need thereof a composition according to the present invention.

According to another embodiment, the present invention relates to a method of treating or lessening the severity of an autoimmune disorder selected from inflammatory bowel disease ("IBD"), and more specifically Crohn's disease (see Neurath, M. F. et al. *J. Exp. Med.* 2002, 195, 1129; and Matsuoka, K. et al. *Gut* 2004, 53, 1303), rheumatoid arthritis (see Chen, J. et al. *Inflammation Res.* 2004, 53, 670), multiple sclerosis (see Lovett-Racke, A. E. et al. *Immunity* 2004, 21, 719; and Bettelli, E. et al. *J. Exp. Med.* 2004, 200, 79), systemic lupus erythematosus (see Peng, S. L. et al. *PNAS* 2002, 99, 5545), type I diabetes mellitus (see Sasaki, Y. et al. *Human Genetics* 2004, 115, 177; and Juedes, A. E. et al. *J. Exp. Med.* 2004, 199, 1153), HTLV-1-associated myelopathy/tropical spastic paraparesis (see Nishura, Y. et al. *Tohoku J. Exp. Med.* 2004, 204, 289), artherosclerosis, (see Buono, C. et al. *PNAS* 2005, 102, 1596), Hodgkin's Lymphoma (see Dorfman, D. M. et al. *Human Pathology* 2005, 36, 10), B-cell lymphoblastic leukemia/lymphoblastic lymphoma (see Dorfman, D. M. et al. *Am. J. Clin. Pathol.* 2004, 122, 292), chronic lymphocytic leukemia, marginal zone lymphoma, and hairy cell leukemia (see Dorfman, D. M. et al. *Am. J. Clin. Pathol.* 2004, 122, 292), Behcet's disease (see Li, B. et al. *Yanke Yanjiu* 2004, 22, 1), Coeliac disease, (see Monteleone, I. et al. *Gut* 2004, 53, 1090), T-cell-mediated liver inflammation (see Siebler, J. et al. *Hepatology* 2003, 38, 1573), optic neuritis or inflammation or demyelination of the optic nerve (see Theodoridou, A. and Settas, L., *J. Neurol. Neurosurg. Psychiatry* 77(3) 290-5 (2006)), psoriasis, scleroderma, Graft v. Host disease, autoimmune hemolytic anemia, autoimmune thrombocytopenic purpura, goodpasture's syndrome, pemphigus vulgaris, acute rheumatic fever, mixed essential cryoglobulinemia, Grave's disease, Hashimoto's thyroiditis, autoimmune pernicious anemia, autoimmune Addison's Disease, vitiligo, myasthenia gravis, primary Sjögren's syndrome, polymyositis, primary myxoedema, thyrotoxicosis, autoimmune atrophic gastritis, juvenile diabetes, pemphigoid, sympathetic opthalmia, phacogenic uveitis, idiopathic leucopenia, primary biliary cirrhosis, active chronic hepatitis, dermatomyositis, or discoid lupus erythematosus.

According to another embodiment, the present invention relates to a method of treating or lessening the severity of an autoimmune disorder selected from inflammatory bowel disease ("IBD"), and more specifically Crohn's disease, rheumatoid arthritis, multiple sclerosis, systemic lupus erythematosus, type 1 diabetes mellitus, HTLV-1-associated myelopathy/tropical spastic paraparesis, artherosclerosis, Hodgkin's Lymphoma, B-cell lymphoblastic leukemia/lymphoblastic lymphoma, chronic lymphocytic leukemia, marginal zone lymphoma, and hairy cell leukemia, Behcet's disease, Coeliac disease, and T-cell-mediated liver inflammation.

According to another embodiment, the present invention relates to a method of treating or lessening the severity of an autoimmune disorder selected from psoriasis, scleroderma, Graft v. Host disease, autoimmune hemolytic anemia, autoimmune thrombocytopenic purpura, goodpasture's syndrome, pemphigus vulgaris, acute rheumatic fever, mixed essential cryoglobulinemia, Grave's disease, Hashimoto's thyroiditis, autoimmune pernicious anemia, autoimmune Addison's Disease, vitiligo, myasthenia gravis, primary Sjögren's syndrome, polymyositis, primary myxoedema, thyrotoxicosis, autoimmune atrophic gastritis, juvenile diabetes, pemphigoid, sympathetic opthalmia, phacogenic uveitis, idiopathic leucopenia, primary biliary cirrhosis, active chronic hepatitis, dermatomyositis, or discoid LE.

In certain embodiments, the present invention provides a method for treating a T-bet-mediated disease, as described herein, by administering a compound of formula I. In other embodiments, the present invention provides a method for treating a T-bet-mediated disease, as described herein, by administering a compound of Examples 1 through 301. According to another aspect, the present invention provides a method for treating a T-bet-mediated disease, as described herein, by administering a compound selected from ER 818561, ER 817135, ER 813508, ER 813509, ER 813493, ER 813510, ER 813511, ER 817118, ER 817137, ER 817119, ER 818573, ER 818567, ER 818550, and ER 813512. According to yet another aspect, the present invention provides a method for treating a T-bet-mediated disease, as described herein, by administering a compound selected from ER 813499, ER 813081, ER 813077, ER 818528, ER 818574, ER 813411, ER 813078, ER 813521, ER 817116, ER 813080, ER 813519, ER 813492, ER 813452, ER 813410, and ER 812605. In other embodiments, the present invention provides a method for treating a T-bet-mediated disease, as described herein, by administering a compound selected from ER 818568, ER 813091, ER 813075, ER 818562, ER 813096, ER 819695, ER 813092, ER 813082, ER 820087, ER 813079, ER 813089, ER 813529, ER 813414, and ER 813516. In still other embodiments, the present invention provides a method for treating a T-bet-mediated disease, as described herein, by administering a compound selected from ER 818558, ER 818559, ER 818560, ER 818554, ER 818535, ER 818564, ER 818524, and ER 817117.

In order that the invention described herein may be more fully understood, the following examples are set forth. It should be understood that these examples are for illustrative purposes only and are not to be construed as limiting this invention in any manner.

EXAMPLES

E. Chemical Examples

General: Microwave heating was done using an Emrys Liberator microwave. LC/MS was conducted using a Waters autopurifier and 19×100 mm XTerra 5 micron MS C18 column or 20×50 mm 5 micron PFC8 column and MeOH/0.05% TFA (aq) or acetone/0.05% TFA (aq) mobile phase. Final compounds were re-analyzed analytically by LC/MS using a Waters autopurifier and 4.6×100 mm XTerra 5 micron MS C18 column and MeOH/0.05% TFA (aq) mobile phase. All final compounds were determined to be >90% pure and displayed suitable spectroscopic properties. Evaporation and concentrations were conducted using a Genevac evaporator or a rotary evaporator.

As used herein, "DMF" refers to dimethylformamide, "DCE" refers to dichloroethane, "NMP" refers to N-methylpyrrolidine, "DBU" refers to 1,8-diazabicyclo[5.4.0]undec-7-ene, "MTBE" refers to methylt-butylether, and "DMSO" refers to dimethylsulfoxide.

General methods and experimentals for preparing compounds of the present invention are set forth below. In certain cases, a particular compound is described by way of example.

However, it will be appreciated that in each case a series of compounds of the present invention were prepared in accordance with the schemes and experimentals described below.

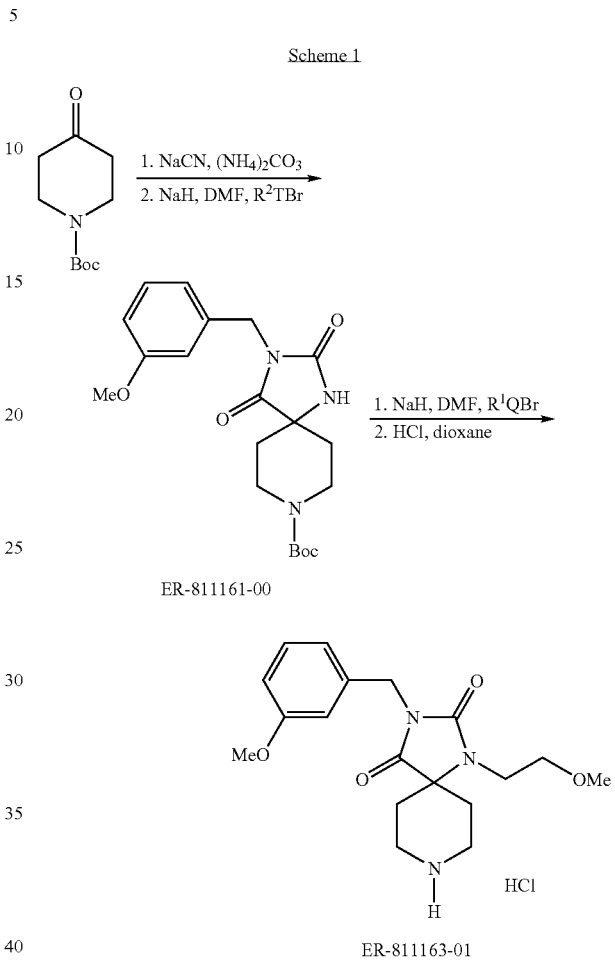

Exemplary Procedure for the Synthesis of Spiro-piperidine Hydantoin Scaffold for $R^3$ Analogs. As depicted in Scheme 1 above, N-Boc-4-piperidone (100 g, 502 mmol), NaCN (37 g, 755 mmol), and $(NH_4)_2CO_3$ (243 g, 253 mmol) in EtOH (250 mL) and $H_2O$ (250 mL) was heated at 60° C. overnight. Upon cooling to ambient temperature, the white solid was filtered, washed with warm $H_2O$, and dried in vacuo to provide 134 g. The solid (30 g, 112 mmol) was dissolved in DMF (300 mL), NaH (5.4 g of 60% dispersion in mineral oil, 135 mmol) was added, stirred at ambient temperature ~2 hours, then 3-methoxybenzyl bromide (112 mmol) was added and the reaction was stirred overnight. Typical aqueous work-up provided ER-811161-00 as an oil. ER-811161-00 was dissolved in DMF (300 mL), NaH (5.4 g of 60% dispersion in mineral oil, 135 mmol) was added, stirred at ambient temperature 15 minutes, then 2-methoxyethyl bromide was added and the reaction was stirred overnight. Typical aqueous work-up provided the Boc protected intermediate, which was dissolved in 4 M HCl in dioxane (100 mL). After stirring 2 hours, the reaction was concentrated to give 20.7 g of ER-811163-01 as a foam.

Scheme 2

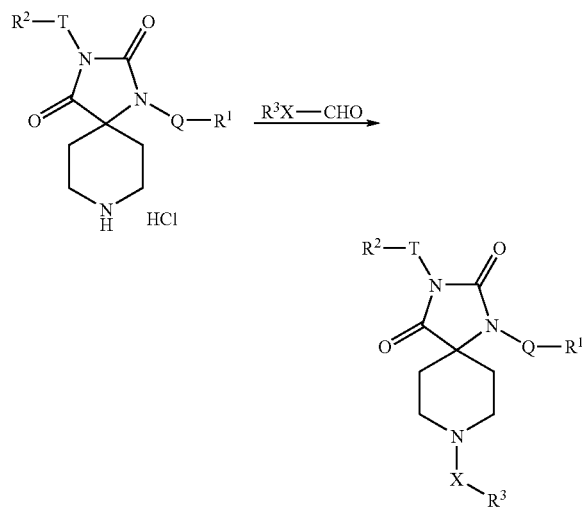

Exemplary Procedure for Reductive Amination with Aldehydes. As depicted in Scheme 2 above, a 0.20 M solution of scaffold (0.10 mmol) in DCE and a 0.10 M solution of TMAT (0.20 mmol) in DCE were added to a microwave reaction tube containing an aldehyde (0.10 mmol). The reaction was microwave heated at 170° C. for 180 s, concentrated, the residue was dissolved in 10% aqueous DMSO, and the reaction mixture was purified by LC/MS.

Scheme 3

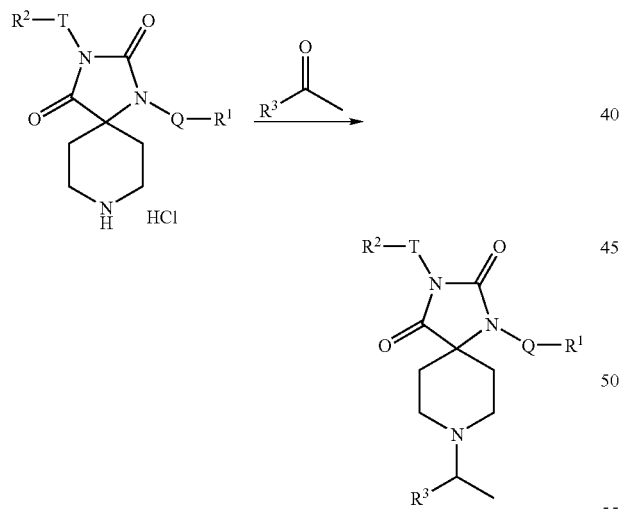

Exemplary Procedure for Reductive Aminations with Ketones. As depicted in Scheme 3 above, a 0.20 M solution of scaffold (0.25 mmol) in DCE and a 0.75 M solution of Ti(OiPr)$_4$ (0.53 mmol) in DCE were added to a microwave reaction tube containing a ketone (0.50 mmol), and microwave heated at 170° C. for 300 s. Polymer-supported borohydride (Aldrich Amberlite® IRA-400 2.5 mmol/g, 1.0 mmol) and EtOH (3.75 mL) was added and the reaction microwave heated at 100° C. for 300 s. PS-DEAM (Argonaut 1.63 mmol/g, 0.88 mmol) and DCE (1.25 mL) were added and the reaction placed on a shaker for 48-72 hours, then filtered and concentrated. The residue was dissolved in DMSO, filtered, and the reaction mixture was purified by LC/MS.

Scheme 4

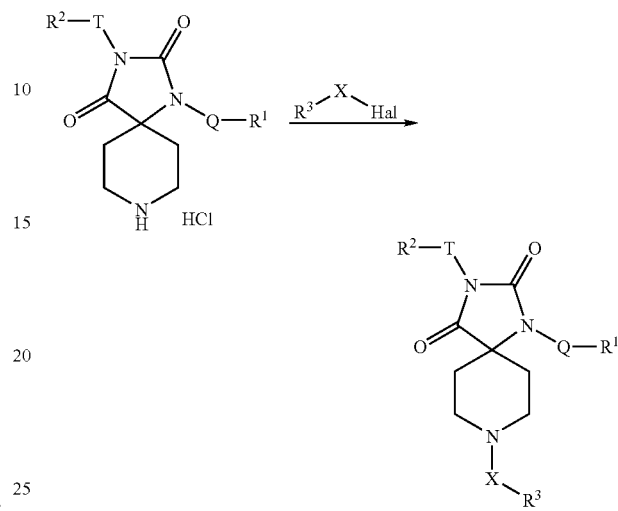

Exemplary Procedure for Alkylations of Piperidines. As depicted in Scheme 4 above, a 0.20 M solution of scaffold (0.25 mmol) in NMP and DBU (0.50 mmol) were added to a microwave reaction tube containing an R$^3$—X-halide (0.25-0.375 mmol) in NMP (1.2 mL). The reaction was microwave heated at 180° C. for 60 s, then purified by LC/MS.

Scheme 5

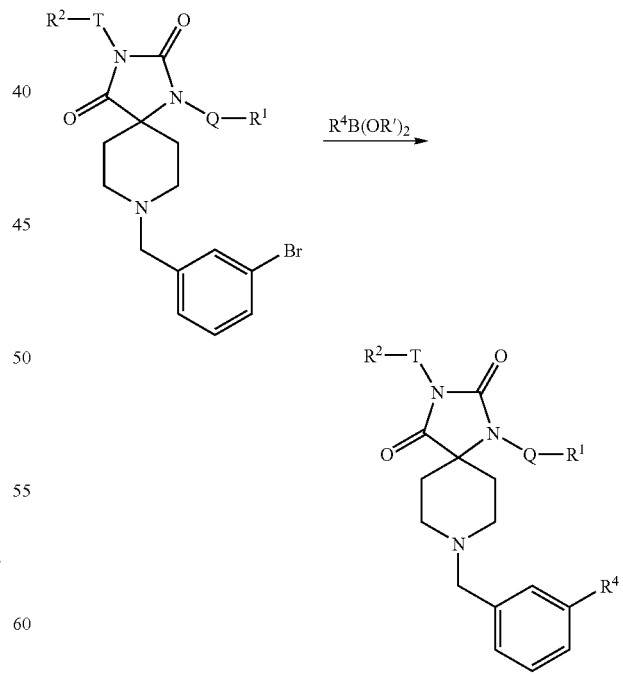

Exemplary Procedure for Suzuki Coupling at R$^3$. As depicted in Scheme 5 above, a 0.183 M solution of scaffold (0.10 mmol) in EtOH/NMP (2.25/1), a 0.50 M solution of Et$_3$N (0.20 mmol) in EtOH, and a 0.021 M solution of Pd(Ph₃P)₂Cl₂ (0.0075 mmol) in NMP were added to a microwave reaction tube containing a R⁴-boronic acid (0.30 mmol), wherein R⁴ corresponds to an aryl substituent on R³ as defined above. The reaction was microwave heated at 140° C. for 360 s, and re-subjected to microwave heating as need for complete reaction. The reaction was filtered and purified by LC/MS.

Scheme 6

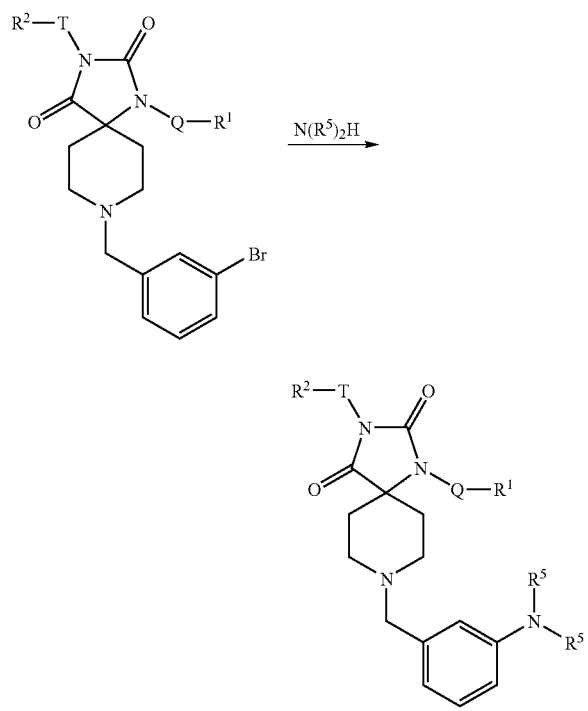

Exemplary Procedure for Aryl Amination at R³. As depicted in Scheme 6 above, scaffold (50 mg, 0.096 mmol), an amine (0.38 mmol), Pd(OAc)₂ (0.007 mmol), 2-(di-t-butylphosphino)biphenyl (0.008 mmol), and NaOtBu (0.10 mmol) were dissolved in DMF (0.5 mL), and microwave heated at 130° C. for 240 s, and re-subjected to microwave heating as need for complete reaction. The reaction was filtered and purified by LC/MS.

Scheme 7

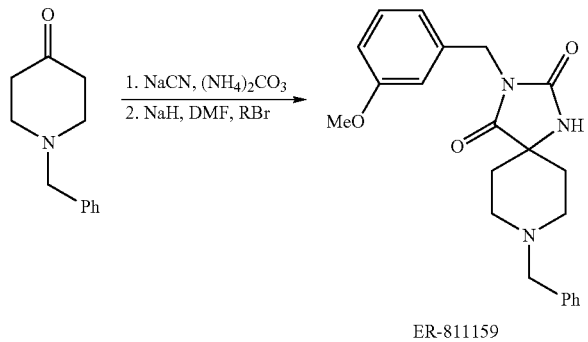

ER-811159

Exemplary Procedure for the Synthesis of Spiro-piperidine Hydantoin Scaffold for R¹ Analogs. As depicted in Scheme 7 above, N-benzyl-4-piperidone (20 g, 106 mmol), NaCN (7.9 g, 160.4 mmol), and (NH₄)₂CO₃ (52 g, 542 mmol) in EtOH (50 mL) and H₂O (50 mL) was heated at 60° C. overnight. Upon cooling to ambient temperature, the white solid was filtered, washed with warm H₂O, and dried in vacuo to provide 27.4 g. The solid (3.0 g, 11.6 mmol) was dissolved in DMF (30 mL), NaH (0.51 g of 60% dispersion in mineral oil, 12.8 mmol) was added, stirred at ambient temperature ~2 hours, then 3-methoxybenzyl bromide (11.6 mmol) was added and the reaction was stirred overnight. Typical aqueous work-up provided 5.5 g ER-811159 as a solid which could be recrystallized from MeOH.

Scheme 8

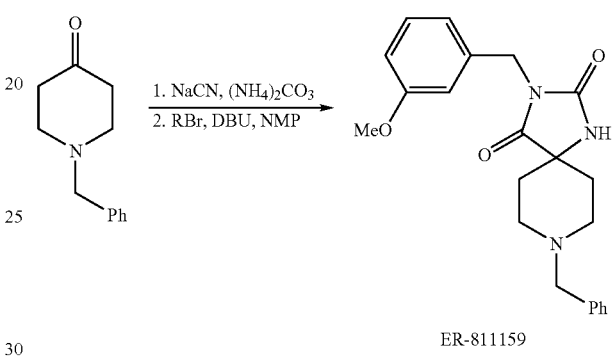

ER-811159

Alternative Procedure for the Synthesis of Spiro-piperidine Hydantoin Scaffold for R¹ Analogs. As depicted in Scheme 8 above, N-benzyl-4-piperidone (20 g, 106 mmol), NaCN (7.9 g, 160.4 mmol), and (NH₄)₂CO₃ (52 g, 542 mmol) in EtOH (50 mL) and H₂O (50 mL) was heated at 60° C. overnight. Upon cooling to ambient temperature, the white solid was filtered, washed with warm H₂O, and dried in vacuo to provide 27.4 g. The solid (3.5 g, 13.3 mmol), 3-methoxybenzyl bromide (13.3 mmol), and DBU (20 mmol) were dissolved in NMP (30 mL), separated into 5 vials and each vial was microwave heated at 180° C. for 60 s. The batches were combined, subjected to typical aqueous work-up, then recrystallized from MeOH/MTBE/hexanes to provided 2.2 g ER-811159.

Scheme 9

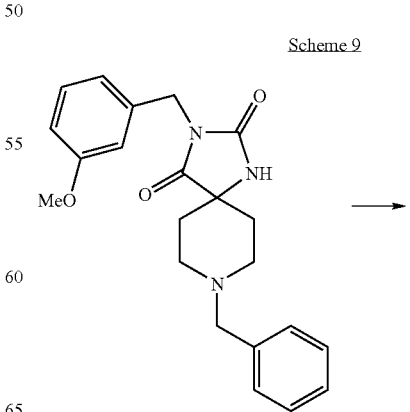

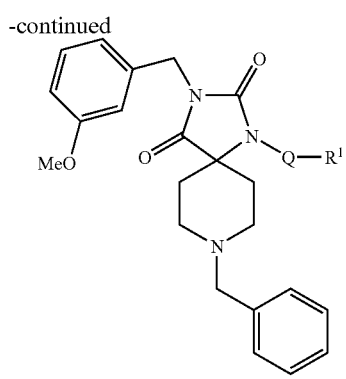

Exemplary Procedure for R¹ Analogs via Alkylation. As depicted in Scheme 9 above, a solution of scaffold (0.10 mmol) in NMP (0.4 mL) and a 1M solution of LiHMDS in THF (0.20 mL, 0.20 mmol) were added to a microwave reaction tube containing a R¹—Q-halide (0.20 mmol). The reaction was microwave heated at 180° C. for 90 s, then quenched with DMSO/H$_2$O (9/1) and purified by LC/MS.

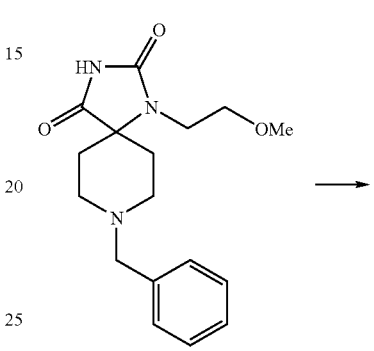

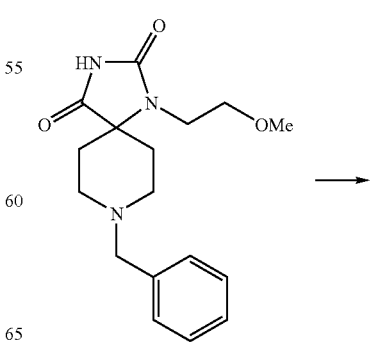

Exemplary Procedure for the Synthesis of Spiro-piperidine Hydantoin Scaffold for R² Analogs. As depicted in Scheme 10 above, N-benzyl-4-piperidone (142 mmol), 2-methoxyethylamine (142 mmol), and concentrated aqueous HCl (12 mL) were dissolved H$_2$O (25 mL)/MeOH (25 mL), and a solution of KCN (142 mmol) in H$_2$O (21 mL) was added dropwise. The reaction was stirred 16 hours, then subjected to typical aqueous workup. The crude oil (111 mmol) and chlorosulfonyl isocyanate (111 mmol) were dissolved in CH$_2$Cl$_2$ (30 mL), stirred 90 minutes, then concentrated and the residue was refluxed in 1M HCl (aq.) for 1 hour. Typical aqueous workup and chromatography provided the desired compound.

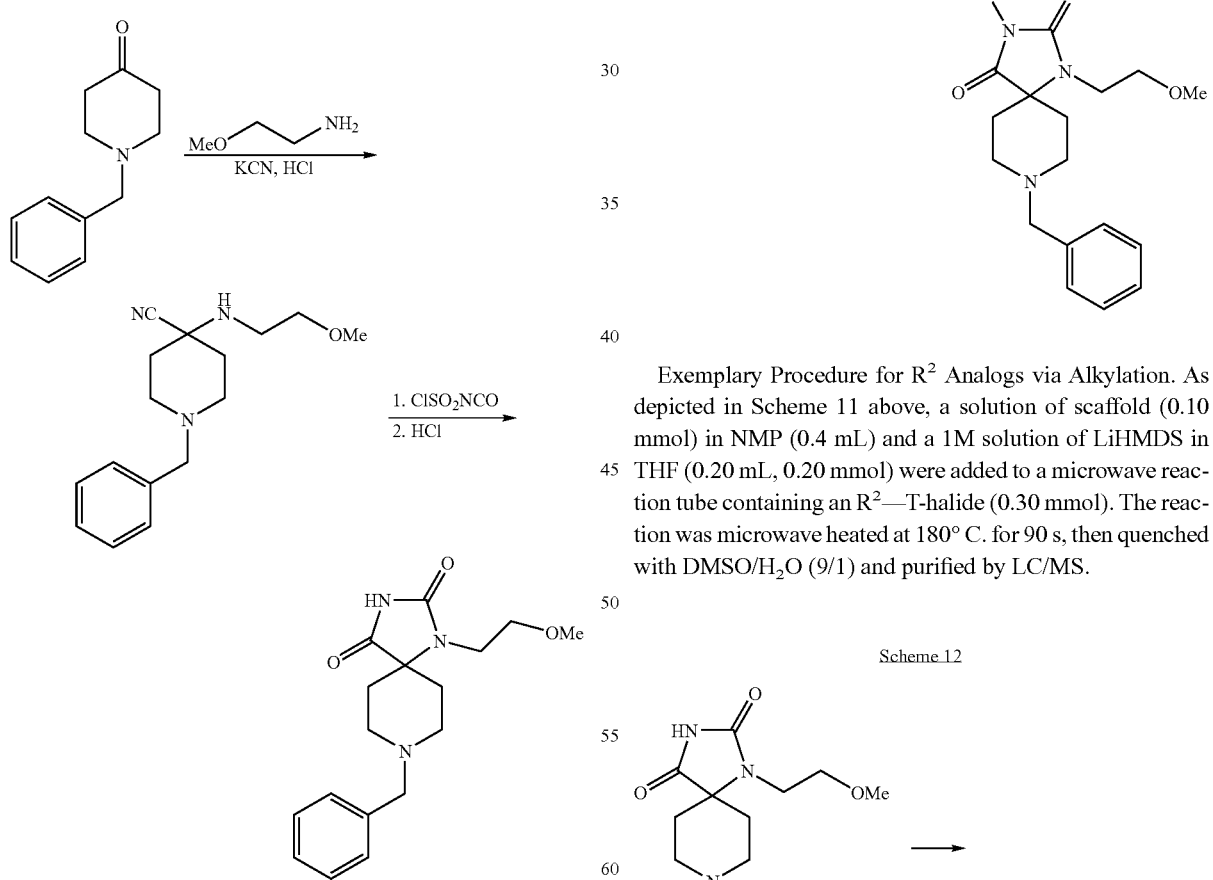

Exemplary Procedure for R² Analogs via Alkylation. As depicted in Scheme 11 above, a solution of scaffold (0.10 mmol) in NMP (0.4 mL) and a 1M solution of LiHMDS in THF (0.20 mL, 0.20 mmol) were added to a microwave reaction tube containing an R²—T-halide (0.30 mmol). The reaction was microwave heated at 180° C. for 90 s, then quenched with DMSO/H$_2$O (9/1) and purified by LC/MS.

-continued

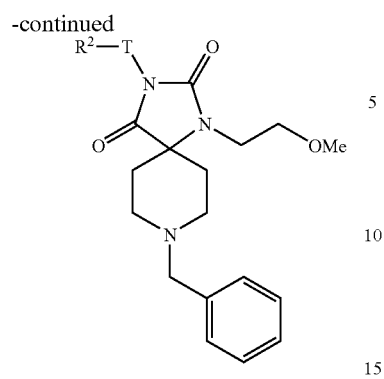

Alternate Procedure for R² Analogs via Alkylation. As depicted in Scheme 12 above, a solution of scaffold (0.20 mmol) in NMP (0.4 mL) and a 2M solution of DBU in NMP (0.20 mL, 0.40 mmol) were added to a microwave reaction tube containing an R²—T-halide (0.25 mmol). The reaction was microwave heated at 180° C. for 180 s, then purified by LC/MS.

Scheme 13

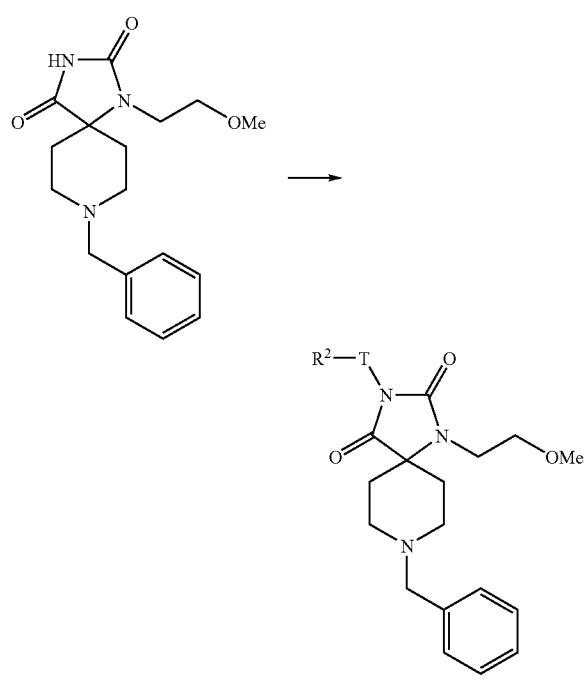

Exemplary Procedure for R² Analogs via Mitsunobu. As depicted in Scheme 13 above, scaffold (0.10 mmol), an R²—T-alcohol (0.20 mmol), perfluoronylazodicarboxylate (0.20 mmol), and diphenyl(perfluoronylphenyl)phosphine (0.30 mmol) were dissolved in THF (0.7 mL) and microwave heated at 60° C. for 180 s, then purified by LC/MS.

Scheme 14

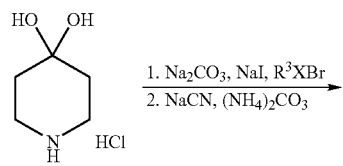

1. Na₂CO₃, NaI, R³XBr
2. NaCN, (NH₄)₂CO₃

-continued

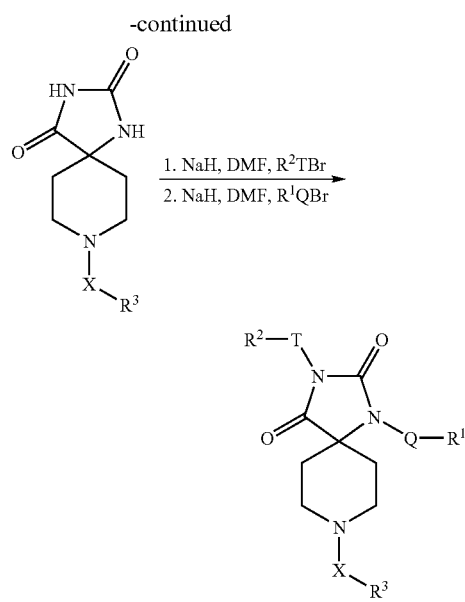

Alternate General Procedure for the Preparation of Spiro-piperidine Hydantoins. As depicted in Scheme 14 above, 4-piperidone hydrate (1.7 g, 11.1 mmol), sodium carbonate (2.1 g, 19.8 mmol), NaI (1.0 g, 6.9 mmol) and the R³X-bromide (10 mmol) were heated at 90° C. in DMF (40 mL) overnight. The reaction was filtered and subjected to typical aqueous workup produced 2.2 g. The ketone (10 mmol), NaCN (0.75 g, 15.3 mmol), and (NH₄)₂CO₃ (5.0 g, 52 mmol) in EtOH (10 mL) and H₂O (10 mL) was heated at 60° C. overnight. Upon cooling to ambient temperature, the white solid was filtered, washed with warm H₂O, and dried in vacuo to provide 2.2 g. The solid (6.6 mmol) was dissolved in DMF (20 mL), NaH (0.34 g of 60% dispersion in mineral oil, 8.5 mmol) was added, stirred at ambient temperature ~2 hours, then the R²T-bromide (6.6 mmol) was added and the reaction was stirred overnight and then subjected to typical aqueous work-up. The intermediate (1.6 mmol) was dissolved in DMF (15 mL), NaH (0.11 g of 60% dispersion in mineral oil, 2.75 mmol) was added, stirred at ambient temperature 15 minutes, then the R¹Q-bromide (1.9 mmol) was added and the reaction was stirred overnight. Typical aqueous work-up and chromatography provided the desired product.

Scheme 15

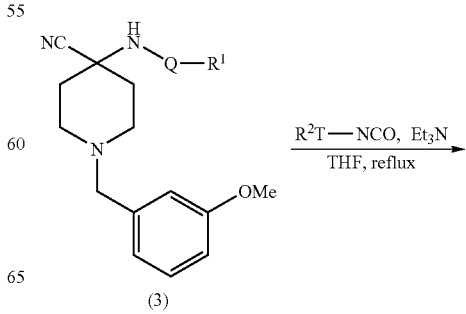

(3)

-continued

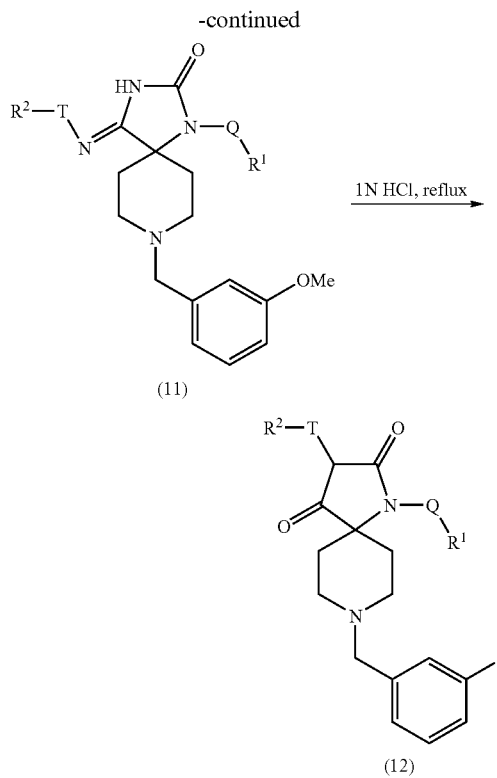

Exemplary Procedure for the Preparation of Iminohydantoins (11). As depicted in Scheme 15 above, to a solution of a suitably chosen isocyanate (1.1 equivalents) in a suitable amount of THF was added triethylamine (0.15 equivalents). This was followed by the slow addition of a solution of amino nitrile (3) in an appropriate amount of THF. The reaction solution was brought to reflux for 0.5 hours. The reaction was cooled to room temperature. Chromatographic purification gave the corresponding iminohydantoins (11).

Exemplary Procedure for the Preparation of Hydantoins (12). As depicted in Scheme 15 above, to a solution of iminohydantoin (11) in a suitable amount of methanol was added 1N HCl (2.5 equivalents). The reaction solution was refluxed for 1 hour, and then cooled back to room temperature. Basic aqueous work up gave the corresponding hydantoin (12).

-continued

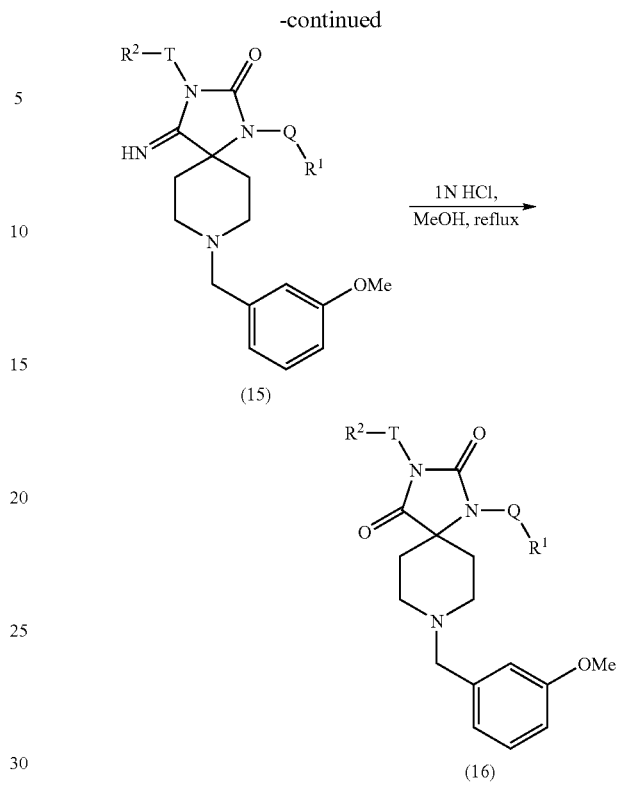

Exemplary Procedure for the Preparation of Iminohydantoins (15). As depicted in Scheme 16 above, to a solution of amino nitrile (3) in a suitable amount of toluene was added an appropriately chosen isocyanate (1.0 equivalent), followed by the addition of triethylamine (0.6 equivalents). The reaction solution was refluxed for 24 hours, and then cooled back to room temperature. Aqueous work up, followed by chromatographic purification gave the corresponding iminohydantoin (15).

Exemplary Procedure for the Preparation of Hydantoins (16). As depicted in Scheme 16 above, to a solution of iminohydantoin (15) in a suitable amount of methanol was added 1N HCl (2.5 equivalents). The reaction solution was refluxed for 1 hour, and then cooled back to room temperature. Basic aqueous work up gave the corresponding hydantoin (16).

Scheme 16

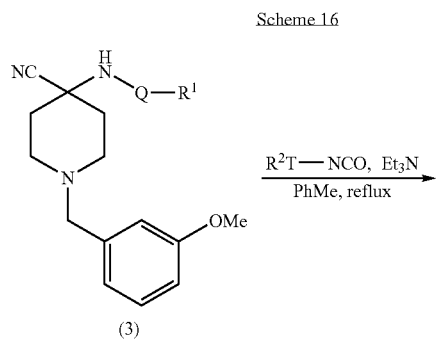

Scheme 17

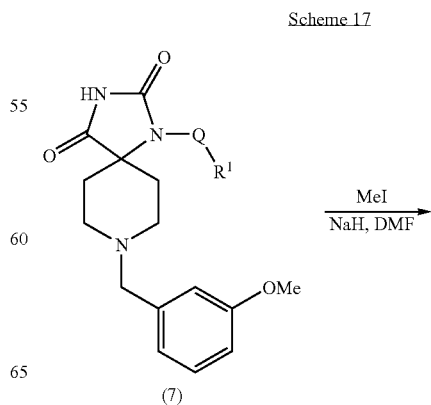

-continued

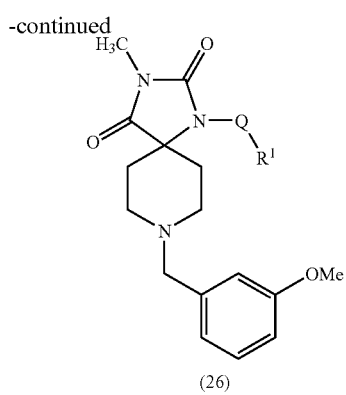

(26)

Exemplary Procedure for the Preparation of Hydantoins (26). As depicted in Scheme 17 above, to a solution of hydantoin (7) in a suitable amount of DMF was added NaH (1.5 equivalents). This was followed by the addition of methyl iodide (1.5 equivalents). The reaction solution was stirred overnight. Aqueous work up, followed by chromatographic purification gave the corresponding hydantoin (26).

Compounds of the present invention were prepared in accordance with the methods described herein and those known to one of ordinary skill in the art. Such compounds include those listed in Tables 1, 2, 3, and 4 set forth below. Table 1 provides analytical data, including $^1$H NMR data, for exemplary compounds of the present invention.

TABLE 1

$^1$H NMR Data for Exemplary Compounds of Formula I

| Example # | Structure | ER # | Analytical Data |
|---|---|---|---|
| 1 | 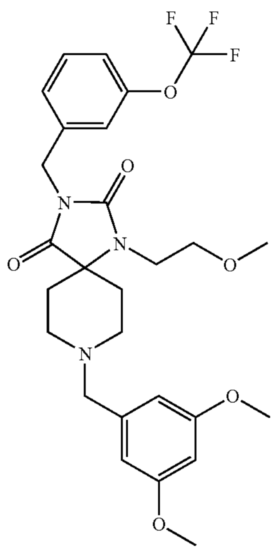 | 819711 (salt free) | NMR $^1$H (400 MHz, CDCl$_3$) δ 7.37-7.33 (t, J=7.8 Hz, 1H), 7.30-7.28(m, 1H), 7.21 (br, 1H), 7.15-7.12 (m, 1H), 6.52 (d, J=2.3 Hz, 2H), 6.37 (t, J=2.3, 1H), 4.64 (s, 2H), 3.80 (s, 6K), 3.57 (t, J=6.0 Hz, 2H) 3.52 (s, 2H), 3.44 (t, J=6.0 Hz, 2H), 3.35 (s, 3H), 2.80-2.73 (m, 4H), 2.09-2.01 (m, 2H), 1.62-1.58 (m, 2H) |
| 2 | 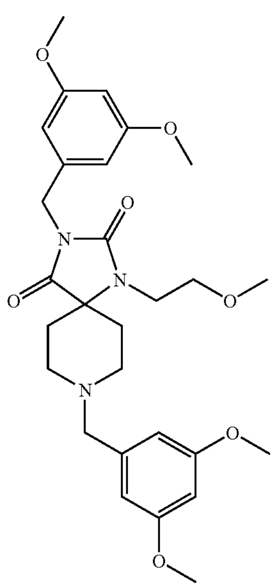 | 817116 (salt free) | NMR $^1$H (400 MHz, DMSO) δ 6.47-6.46 (m, 2H), 6.39-6.37 (m, 1H), 6.35 (br, 1H) 6.30 (br, 2H), 4.44 (s, 2H), 3.70 (s, 6H), 3.67 (s, 6H), 3.45-3.43 (m, 4H), 3.39-3.38 (m, 2H), 3.23 (s, 3H), 2.70-2.59 (m, 4H), 2.03-1.95 (m, 2H), 1.58-1.55 (m, 2H) |

TABLE 1-continued $^1$H NMR Data for Exemplary Compounds of Formula I

| Example # | Structure | ER # | Analytical Data |
|---|---|---|---|
| 3 | 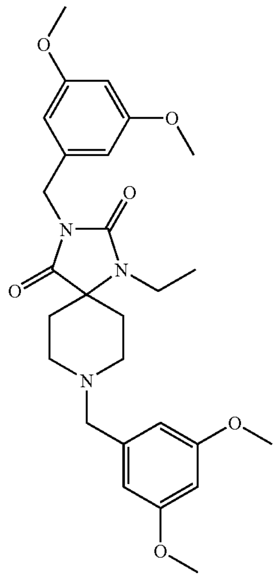 | 817118 (salt free) | NMR $^1$H (400 MHz, DMSO) δ 6.47-6.46 (m, 2H), 6.38-6.37(m, 1H), 6.35-3.34 (m, 1H), 6.30-6.29(m, 2H), 4.44 (s, 2H), 3.70 (s, 6H), 3.67 (s, 6H), 3.45 (s, 2H), 3.29-3.24 (m, 2H), 2.71-2.59 (m, 4H), 2.00-1.93 (m, 2H), 1.61-1.57 (m, 2H), 1.10 (t, J=7.4 Hz, 3H) |
| 4 | 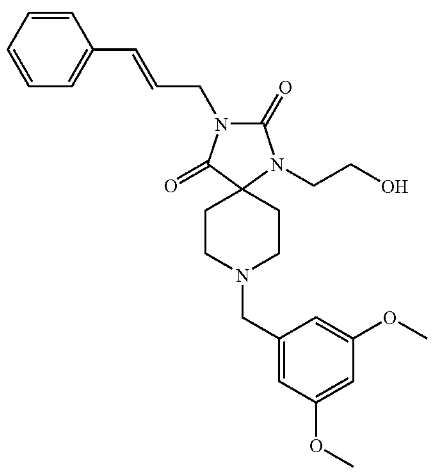 | 818528 (TFA salt) | NMR $^1$H (400 MHz, CD$_3$OD) δ 7.39-7.36 (m, 2H), 7.31-7.26 (m, 2H), 7.24-7.20 (m, 1H), 6.69-6.68 (m, 1H), 6.62-6.58 (m, 2H), 6.25-6.18 (m, 1H), 4.33 (s, 2H), 4.25-4.23 (m, 2H), 3.81 (s, 6H), 3.76-3.72 (m, 4H), 3.56-3.51 (m, 2H), 3.36-3.33 (m, 2H), 2.39-2.30 (m, 2H), 2.08-2.03 (m, 2H) |
| 5 | 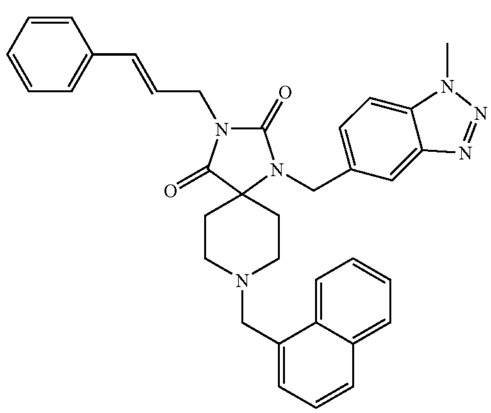 | 818554 (TFA salt) | NMR $^1$H (400 MHz, CD$_3$OD) δ 8.21-8.19 (m, 1H), 8.05 (d, 1H), 8.00 (d, 1H), 7.87 (s, 1H), 7.71-7.68(m, 3H), 7.64-7.54 (m, 3H), 7.43-7.40 (m, 2H), 7.34-7.25 (m, 3H), 6.68-6.64 (m, 1H), 6.34-6.27 (m, 1H), 4.89 (s, 2H), 4.72 (s, 2H), 4.37-4.35 (m, 2H), 4.29 (s, 3H), 3.93-3.86 (m, 2H), 3.56-3.48 (m, 2H), 2.25-2.18 (m, 2H), 2.01-1.97 (m, 2H) |

TABLE 1-continued
¹H NMR Data for Exemplary Compounds of Formula I
| Example # | Structure | ER # | Analytical Data |
|---|---|---|---|
| 6 | 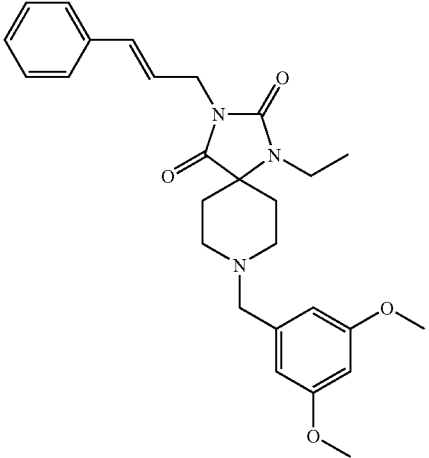 | 813509 (TFA salt) | NMR ¹H (400 MHz, CD$_3$OD) δ 7.40-7.37 (m, 2H), 7.32-7.28 (m, 2H), 7.25-7.22 (m, 1H), 6.70-6.69 (m, 2H), 6.61-6.57 (m, 2H), 6.26-6 19 (m, 1H), 4.33 (br, 2H), 4.25-4.23 (m, 2H), 3.82 (s, 6H), 3.77-3.69 (m, 2H), 3.55-3.50 (m, 2H), 3.35-3.31 (m, 2H), 2.35-2.28 (m, 2H), 2.10-2.06 (m, 2H), 1.24 (t, J=7.0 Hz, 3H) |
| 7 | 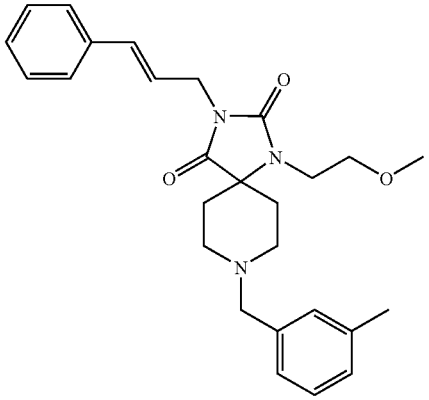 | 813493 (TFA salt) | NMR ¹H (400 MHz, CD$_3$OD) δ 7.39-7.23 (m, 8H), 6.61-6.57 (m, 1H), 6.26-6.19 (m, 1H), 4.37 (br, 2H), 4.26-4.23 (m, 2H), 3.78-3.71 (m, 2H), 3.57-3.51 (m, 4H), 3.43 (br, 2H), 3.31 (s, 3H) 2.40 (s, 3H), 2.36-2.32 (m, 2H), 2.06-2.02 (m, 2H) |
| 8 | 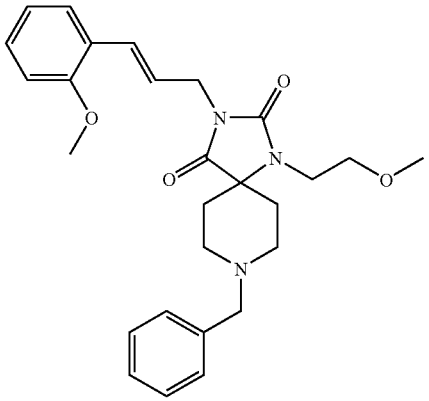 | 813410 (TFA salt) | NMR ¹H (400 MHz, CD$_3$OD) δ 7.55-7.52 (m, 5H), 7.42-7.39 (m, 1H), 7.25-7.21 (m, 1H), 6.96-6.83 (m, 3H), 6.25-6.18 (m, 1H), 4.43 (br 2H), 4.25-4.23 (m, 2H), 3.83 (s, 3H), 3.84-3.74 (m, 2H), 3.57-3.54 (m, 4H), 3.45-3.42 (2H), 3.31 (s, 3H), 2.40-2.33 (m, 2H), 2.07-2.03 (m, 2H), |

… TABLE 1-continued
¹H NMR Data for Exemplary Compounds of Formula I
| Example # | Structure | ER # | Analytical Data |
|---|---|---|---|
| 9 | 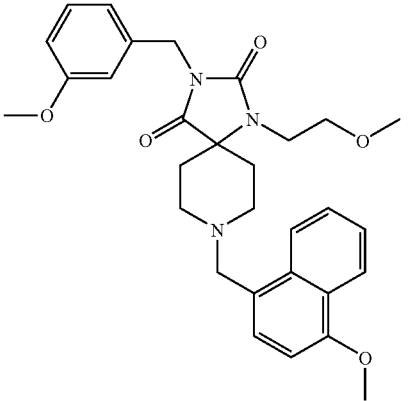 | 813081 (TFA salt) | NMR ¹H (400 MHz, CD₃OD) δ 8.38-8.35 (m, 1H), 8.19-8.15 (m, 1H), 7.74-7.69 (m, 2H), 7.62-7.58 (m, 1H), 7.26-7.22 (m, 1H), 7.04-7.02 (m, 1H), 6.90-6.85 (m, 3H), 4.84 (s, 2H), 4.62 (s, 2H), 4.07 (s, 3H), 3.88-3.82 (m, 2H), 3.78 (s, 3H), 3.63-3.59 (m, 2H), 3.53-3.51 (m, 2H), 3.40-3.36 (m, 2H), 3.27 (m, 3H), 2.36-2.30 (2H), 1.98-1.94 (m, 2H) |
| 10 | 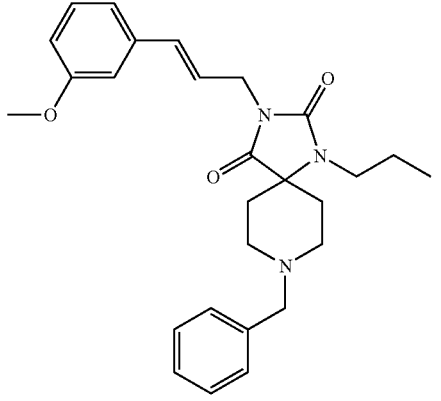 | 813411 (TFA salt) | NMR ¹H (400 MHz, CD₃OD) δ 7.56-7.51 (m, 5H), 7.21 (t, J=7.9 Hz, 1H), 6.97-6.93 (m, 2H), 6.83-6.80 (m, 1H), 6.56 (d, H32 15.8 Hz, 1H), 6.25-6.18 (m, 1H), 4.42 (s, 2H), 4.25-4.23 (m, 2H), 3.79 (m, 3H), 3.80-3.74 (m, 2H), 3.58-3.53 (m, 4H), 3.44-3.42 (m, 2H), 3.31 (s, 3H), 2.38-2.31 (m, 2H), 2.07-2.04 (m, 2H) |
| 11 | 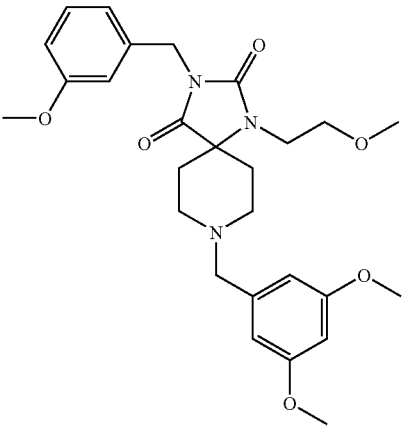 | 812605 (salt free) | NMR ¹H (400 MHz, CDCl₃) δ 7.23 (t, 17.9 Hz, 1H), 6.95-6.89 (m, 2H), 6.83-6.80 (m, 1H), 6.52-6.51 (m, 2H), 6.37-6.36 (t, J=2.2 Hz, 1H), 4.61 (s, 2H), 3.80 (s, 6H), 3.79 (s, 3H), 3.57-3.55 (m, 2H), 3.52 (s, 2H), 3.44-3.42 (m, 2H), 3.34 (s, 3H), 2.80-2.77 (m, 4H), 2.08-2.01 (m, 2H), 1.69-1.59 (m, 2H), |

TABLE 1-continued

¹H NMR Data for Exemplary Compounds of Formula I

| Example # | Structure | ER # | Analytical Data |
|---|---|---|---|
| 12 | 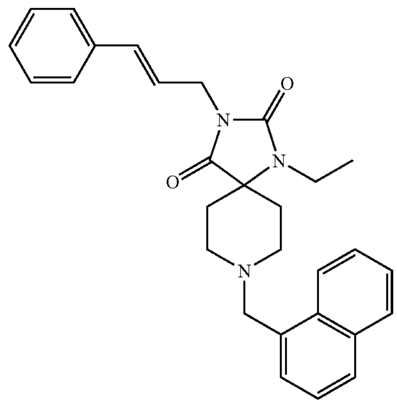 | 813511 (TFA salt) | NMR ¹H (400 MHz, CD₃OD) δ 8.27 (d, J=8.5 Hz, 1H), 8.08 (d, J=8.2 Hz, 1H), 8.02 (d, J=7.9 Hz, 1H), 7.79 (d, J=7.0 Hz, 1H), 7.74-7.70 (m, 1H), 7.66-7.60 (m, 2H), 7.40-7.38(m, 2H), 7.32-7.28 (m, 2H), 7.25-7.22(m, 1H), 6.60 (d, J=15.8 Hz, 1H), 6.27-6.20 (m, 1H), 4.96 (m, 2H), 4.26-2.24(m, 2H), 3.95-3.89 (m, 2H), 3.65-3.62(m, 2H), 3.31-3.26 (m, 2H), 2.33-2.27 (m, 2H), 2.10-2.06 (m, 2H), 1.20 (t, J=6.9 Hz, 3H) |
| 13 | 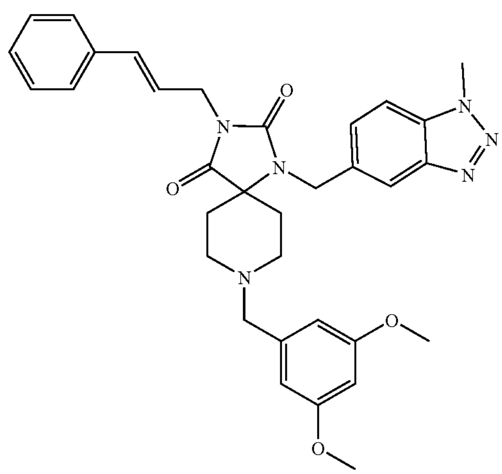 | 818560 (TFA salt) | NMR ¹H (400 MHz, CD₃OD) δ 7.93 (s, 1H), 7.77-7.75 (m, 1H), 7.60-7.58 (m, 1H), 7.42-7.38 (m, 2H), 7.34-7.23 (m, 3H), 6.67-6.58 (m, 4H), 6.33-6.26 (m, 1H), 4.77 (s, 2H), 4.35-4.28 (m, 7H), 3.79 (s, 6H), 3.76-3.69 (m, 2H), 3.49-3.43 (m, 2H), 2.26-2.2 1 (m, 2H), 2.03-1.99 (m, 2H) |
| 14 | 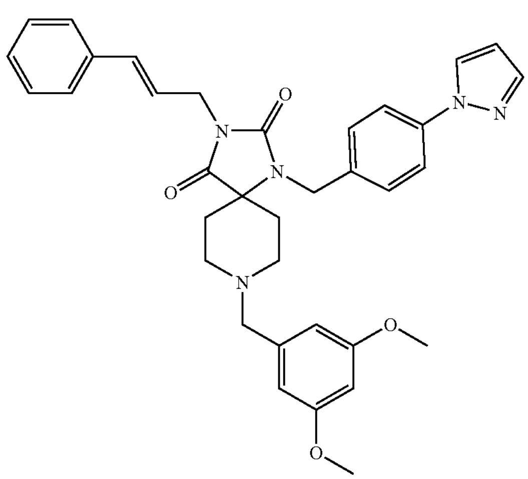 | 818558 (TFA salt) | NMR ¹H (400 MHz,CD₃OD) δ 8.21-8.20 (m, 1H), 7.73-7.72(m, 3H), 7.48-7.46 (m, 2H), 7.72-7.39 (m, 2H), 7.33-7.30 (m, 2H), 7.27-7.24 (m, 1H), 6.65-6.63 (m, 3H), 6.60-6.59 (m, 1H), 6.53-6.52 (m, 1H), 6.32-6.25(m, 1H), 4.63 (s, 2H), 4.34-4.29 (m, 4H), 3.80 (s, 6K), 3.77-3.69 (m, 2H), 3.49-3.45(m, 2H), 2.29-2.22 (m, 2H), 2.04-2.01 (m, 2H) |

TABLE 1-continued
<sup>1</sup>H NMR Data for Exemplary Compounds of Formula I
| Example # | Structure | ER # | Analytical Data |
|---|---|---|---|
| 15 | 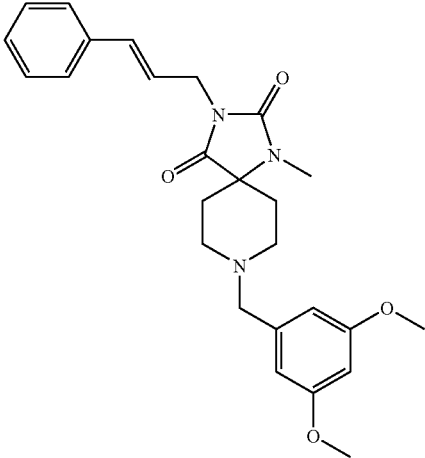 | 818561 (TFA salt) | NMR $^1$H (400 MHz, CD$_3$OD) δ 7.39-7.37 (m, 2H), 6.71-6.70 (m, 2H), 6.62-6.57 (m, 2H), 6.26-6.18 (m, 1H), 4.35 (s, 2H), 4.26-4.24 (m, 2H), 3.82 (s, 6H), 3.78-3.72 (m, 2H), 3.58-3.55 (m, 2H), 2.87 (s, 3H), 2.37-2.30 (m, 2H), 2.07-2.03 (m, 2H) |
| 16 | 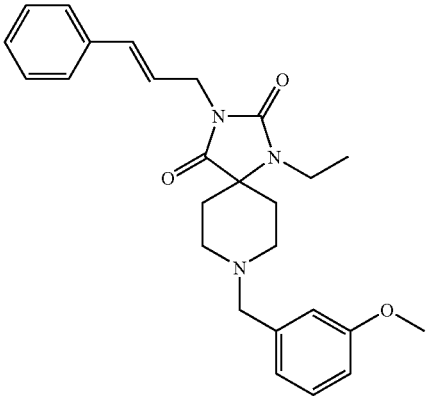 | 813508 (TFA salt) | NMR $^1$H (400 MHz, CD$_3$OD) δ 7.44-7.37 (m, 3H), 7.32-7.28 (m, 2H) 7.25-7.21 (m, 1H), 7.13-7.06 (m, 3H), 6.59 (d, J=16.1 Hz, 1H), 6.26-6.19 (m, 1H), 4.40 (s, 2H), 4.25-4.23 (m, 2H), 3.84 (s, 3H), 3.79-3.73 (m, 2H), 3.56-3.53 (m, 2H), 3.35-3.32 (m, 2H), 2.34-2.28 (m, 2H), 2.12-2.08 (m, 2H), 1.24 (t, J=7.03 Hz. 3H) |
| 17 | 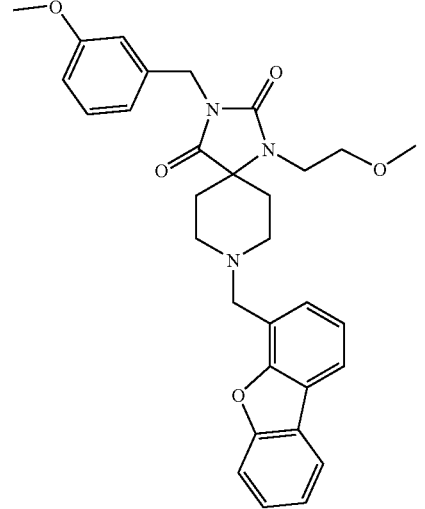 | 817088 (salt free) | M/Z (ES+) Calc.: 527.24 Found: 527.9 (M + H) |

TABLE 1-continued
<sup>1</sup>H NMR Data for Exemplary Compounds of Formula I
| Example # | Structure | ER # | Analytical Data |
|---|---|---|---|
| 18 | 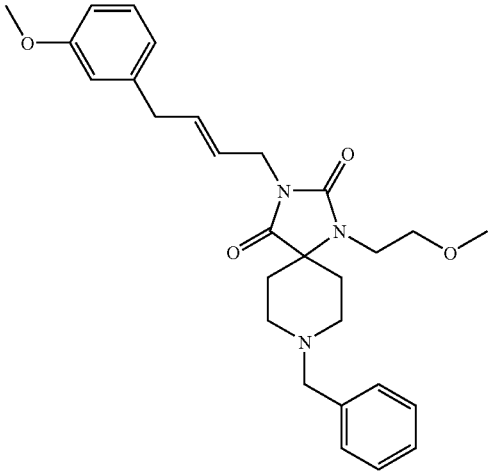 | 817079 (TFA salt) | M/Z (ES+) Calc.: 477.26 Found: 477.90 (M + H) |
| 19 | 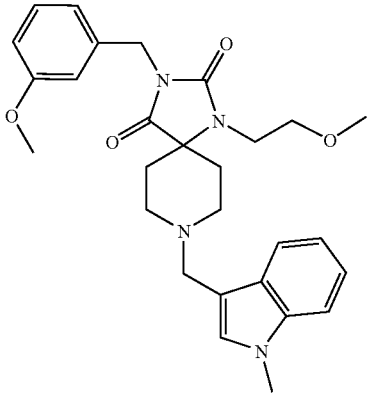 | 813317 (TFA salt) | M/Z (ES+) Calc.: 490.26 Found: 491.1 (M + H) |
| 20 | 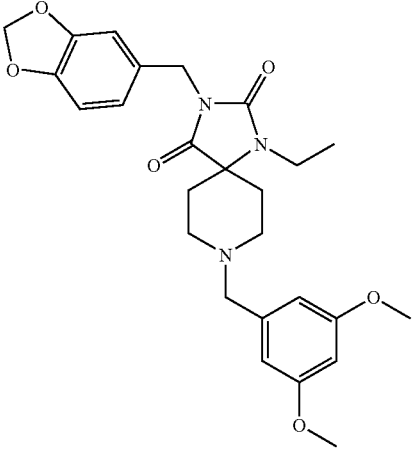 | 819680 (salt free) | M/Z (ES+) Calc.: 481.22 Found: 482.4 (M + H) |

TABLE 1-continued

<sup>1</sup>H NMR Data for Exemplary Compounds of Formula I

| Example # | Structure | ER # | Analytical Data |
|---|---|---|---|
| 21 | 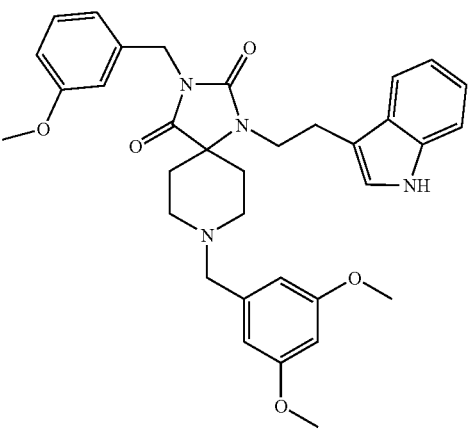 | 818547 (TFA salt) | M/Z (ES+) Calc.: 582.28 Found: 583.3 (M +H) Analytical HPLC: Method A1 Xterra MS C18 (4.6 × 100 mm) 5 um Retention time: 5.02 min |
| 22 | 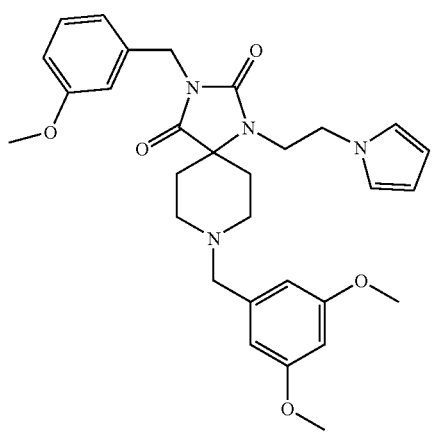 | 818543 (TFA salt) | M/Z (ES+) Calc.: 532.27 Found: 533.3 (M + H) Analytical HPLC: Method A1 Xterra MS C18 (4.6 × 100 mm) 5 um Retention time: 4.91 min |
| 23 | 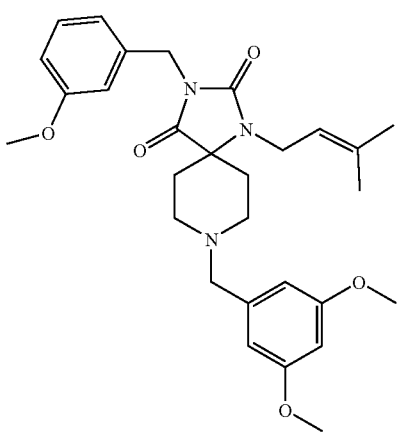 | 818550 (TFA salt) | M/Z (ES+) Calc.: 507.27 Found: 508.3 (M + H) Analytical HPLC: Method A1 Xterra MS C18 (4.6 × 100 mm) 5 um Retention time: 4.96 min |

TABLE 1-continued

¹H NMR Data for Exemplary Compounds of Formula I

| Example # | Structure | ER # | Analytical Data |
|---|---|---|---|
| 24 | 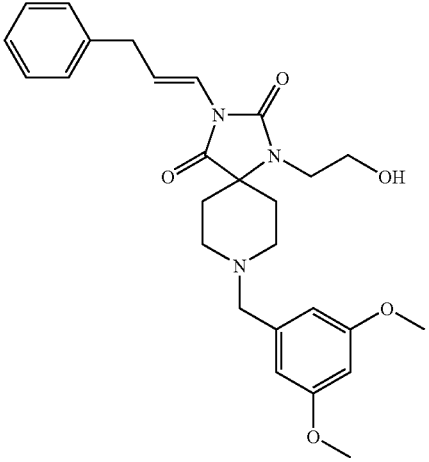 | 817198 (TFA salt) | M/Z (ES+) Calc.: 479.24 Found: 480.2 (M + H) Analytical HPLC: Method A1 Xterra MS C18 (4.6 × 100 mm) 5 um Retention time: 4.76 min |
| 25 | 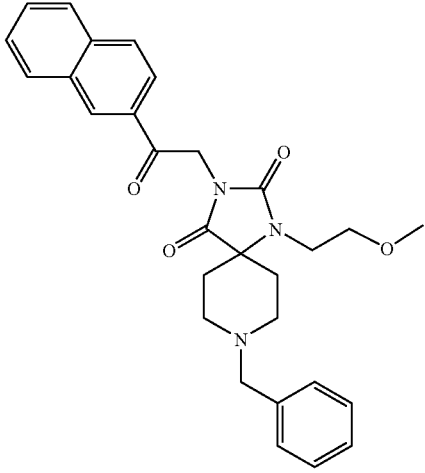 | 812556 (TFA salt) | M/Z (ES+) Calc.: 485.23 Found: 486.4 (M + H) Analytical HPLC: Method A2 Xterra MS C18 (4.6 × 100 mm) 5 um Retention time: 8.25 min |
| 26 | 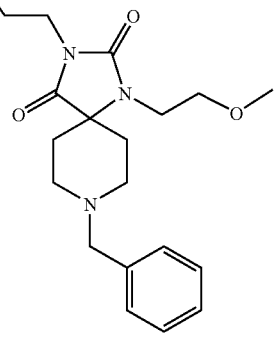 | 813273 (TFA salt) | M/Z (ES+) Calc.: 445.29 Found: 446.3 (M + 1) Analytical HPLC: Method A3 Xterra MS C18 (4.6 × 100 mm) 5 um Retention time: 5.66 min |

TABLE 1-continued

¹H NMR Data for Exemplary Compounds of Formula I

| Example # | Structure | ER # | Analytical Data |
|---|---|---|---|
| 27 | 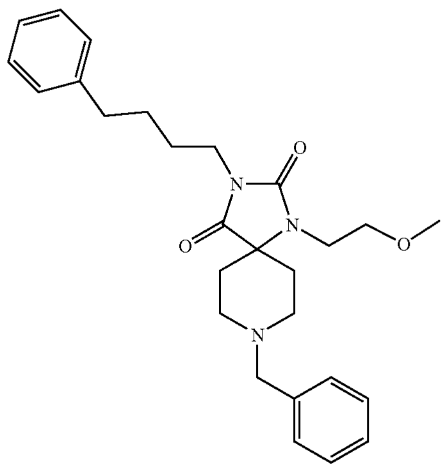 | 213280 (TFA salt) | M/Z (ES+) Calc.: 449.27 Found: 450.3 (M + 1) Analytical HPLC: Method A3 Xterra MS C18 (4.6 × 100 mm) 5 um Retention time: 6.09 min |
| 28 | 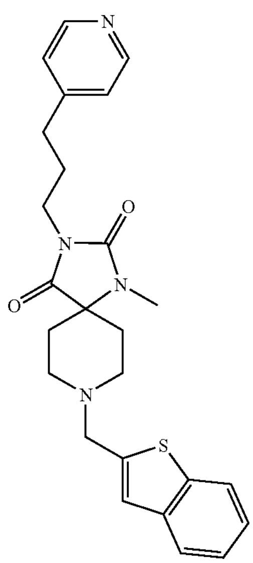 | 817165 (salt free) | (400 MHz, DMSO) δ 8.42-8.40 (m, 2H), 7.88-7.85 (m, 1H), 7.74-7.72 (m, 1H), 7.33-7.26 (m, 3H), 7.22-7.20 (m, 2H), 3.84 (s, 2H), 3.36 (t, J=7.0 Hz, 2H), 2.76 (s, 3H), 2.80-2.67 (m, 4H), 2.54 (t, J=7.6 Hz, 2H), 1.97-1.89 (m, 2H), 1.82-1.78 (m, 2H), 1.57-1.54 (m, 2H) |
| 29 | 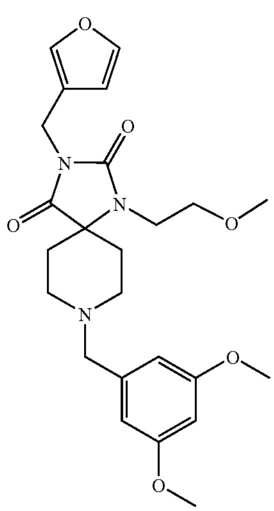 | 819697 (salt free) | (400 MHz, CDCl₃) δ 7.47-7.76 (m, 1H), 7.34 (t, 11.6 Hz, 1H), 6.51 (d, J=2.3 Hz, 2H), 6.43-6.42 (m, 1H), 6.37 (t, J=2.3 Hz, 1H), 4.49 (s, 2H), 3.80 (s, 6H), 3.58-3.54 (m, 2H), 3.52 (s, 2H), 3.44-3.40 (m, 2H), 3.34 (s, 3H), 2.80-2.73 (m, 4H), 2.06-1.98 (m, 2H), 1.62-1.65 (m, 2H) |

TABLE 1-continued

|1H NMR Data for Exemplary Compounds of Formula I|

| Example # | Structure | ER # | Analytical Data |
|---|---|---|---|
| 30 | 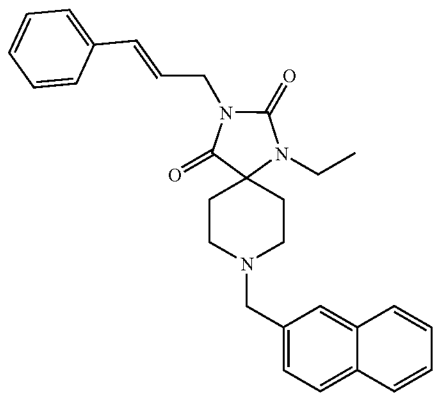 | 813512 (TFA salt) | M/Z (ES+)<br>Calc.: 453.24<br>Found: 454.3 (M + H)<br>Analytical HPLC:<br>Method A4<br>Xterra MS C18 (4.6 × 50 mm) 5 um<br>Retention time: 6.45 min |
| 31 | 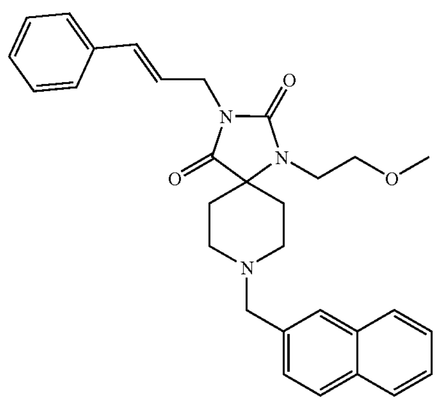 | 813491 (TFA salt) | M/Z (ES+): 484.6 (M + H)<br>Analytical HPLC:<br>Method A4<br>Xterra MS C18 (4.6 × 50 mm) 5 um<br>Retention time: 6.50 min |
| 32 | 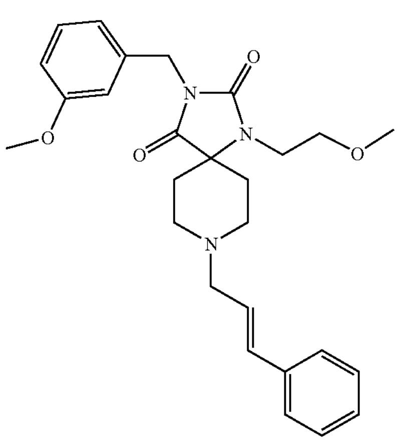 | 813111 (TFA salt) | M/Z (ES+)<br>Calc.: 463.25<br>Found: 464.3 (M + H)<br>Analytical HPLC:<br>Method A5<br>Xterra MS C18 (4.6 × 50 mm) 5 um<br>Retention time: 5.30 min |

TABLE 1-continued $^1$H NMR Data for Exemplary Compounds of Formula I

| Example # | Structure | ER # | Analytical Data |
|---|---|---|---|
| 33 | 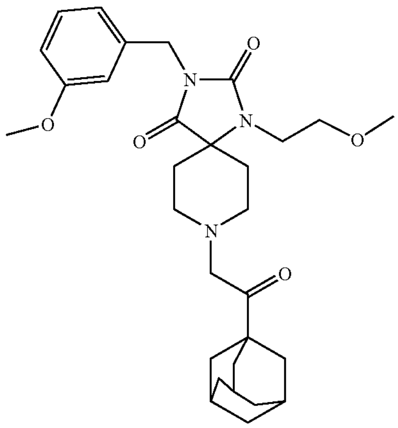 | 812515 (TFA salt) | M/Z (ES+) Calc.: 523.30 Found: 524.S (M + H) Analytical HPLC: Method A5 Xterra MS C18 (4.6 × 50 mm) 5 um Retention time: 5.82 min |
| 34 | 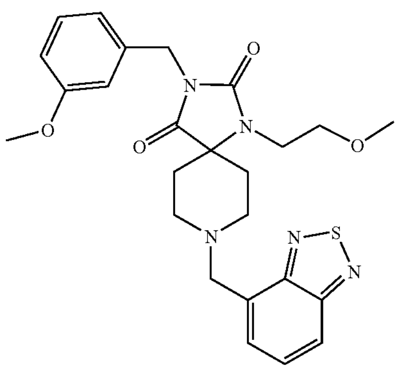 | 812430 (TFA salt) | M/Z (ES+) Calc.: 495.19 Found: 496.4 (M + H) Analytical HPLC: Method A5 Xterra MS C18 (4.6 × 50 mm) 5 um Retention time: 4.82 min |
| 35 | 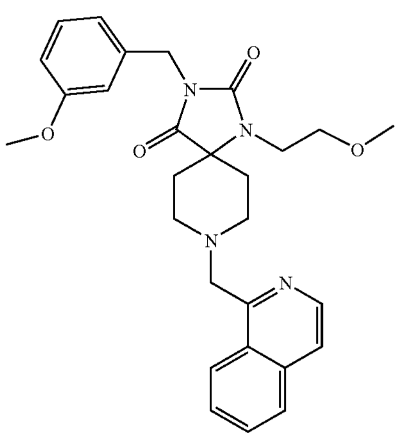 | 812428 (TFA salt) | M/Z (ES+) Calc.: 488.24 Found: 489.4 (M + H) Analytical HPLC: Method A5 Xterra MS C18 (4.6 × 50 mm) 5 um Retention time: 5.05 min |

TABLE 1-continued

¹H NMR Data for Exemplary Compounds of Formula I

| Example # | Structure | ER # | Analytical Data |
|---|---|---|---|
| 36 | 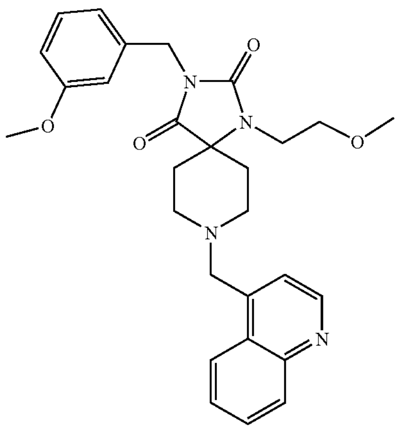 | 812282 (TFA salt) | M/Z (ES+) Calc.: 488.24 Found: 489.4 (M + H) Analytical HPLC: Method A5 Xterra MS C18 (4.6 × 50 mm) 5 um Retention time: 4.34 min |
| 37 | 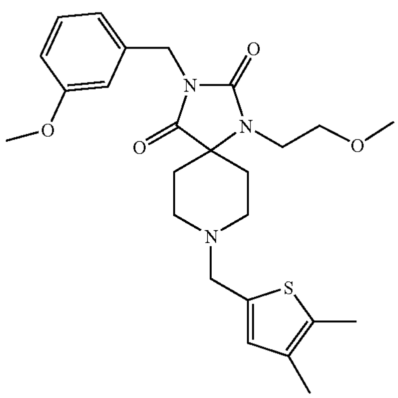 | 812274 (TFA salt) | M/Z (ES+) Calc.: 471.22 Found: 472.4 (M + H) Analytical HPLC: Method A4 Xterra MS C18 (4.6 × 50 mm) 5 um Retention time: 5.44 min |
| 38 | 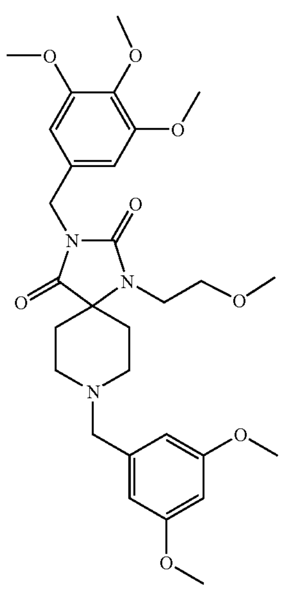 | 819695 (salt free) | NMR ¹H (400 MHz, CDCl$_3$) δ 6.61 (s, 2H), 6.50 (d, J=2.3 Hz, 2H), 6.35 (t, J=2.3 Hz, 1H), 4.55 (s, 2H), 3.83 (s, 6H), 3.81 (s, 3H), 3.78 (s, 6H), 3.57-3.54 (m, 2H), 3.51 (s, 2H), 3.44-3.41 (m, 2H), 3.33 (s, 3H), 2.80-2.73 (m, 4H), 2.08-1.99 (m, 2H), 1.62-1.58 (m, 2H) |

The analytical HPLC methods A1, A2, A3, A4, and A5 referenced in Table 1 are as follows:

| time (min) | % A | % B |
|---|---|---|
| Method A1: | | |
| Solvent A: 0.05% Trifluoroacetic acid in Water | | |
| Solvent B: Acetonitrile | | |
| Flow rate: 1.2 ml/min | | |
| Linear Gradient: | | |
| 0 | 80 | 20 |
| 2 | 80 | 20 |
| 5 | 5 | 95 |
| 7 | 5 | 95 |
| Method A2: | | |
| Solvent A: 0.05% Trifluoroacetic acid in Water | | |
| Solvent B: Methanol | | |
| Flow rate: 2.0 ml/min | | |
| Linear Gradient: | | |
| 0 | 90 | 10 |
| 0.5 | 90 | 10 |
| 6 | 5 | 95 |
| 7 | 5 | 95 |
| 7.01 | 90 | 10 |
| 9 | 90 | 10 |
| Method A3: | | |
| Solvent A: 0.05% Trifluoroacetic acid in Water | | |
| Solvent B: Methanol | | |
| Flow rate: 2.0 ml/min | | |
| Linear Gradient: | | |
| 0 | 90 | 10 |
| 0.5 | 90 | 10 |
| 5 | 5 | 95 |
| 7 | 5 | 95 |
| 7.01 | 90 | 10 |
| 9 | 90 | 10 |
| Method A4: | | |
| Solvent A: 0.05% Trifluoroacetic acid in Water | | |
| Solvent B: Methanol | | |
| Flow rate: 2.0 ml/min | | |
| Linear Gradient: | | |
| 0.00 | 90 | 10 |
| 0.50 | 90 | 10 |
| 5.00 | 10 | 90 |
| 7.00 | 10 | 90 |
| 7.01 | 90 | 10 |
| 9.00 | 90 | 10 |
| Method A5: | | |
| Solvent A: 0.05% Trifluoroacetic acid in Water | | |
| Solvent B: Methanol | | |
| Flow rate: 2.0 ml/min | | |
| Linear Gradient: | | |
| 0.00 | 70 | 30 |
| 0.50 | 70 | 30 |
| 6.00 | 10 | 90 |
| 7.00 | 10 | 90 |
| 7.01 | 70 | 30 |
| 9.00 | 70 | 30 |

F. Biological Examples

HEKT-bet-luc assay: This assay measures a T-bet dependent reporter (luciferase) activity in engineered HEK cells that express a human T-bet and a T-box responsive element driving luciferase reporter. HEKT-bet cells were plated at $2\times10^4$/well in 96-well plate and compound was added into cell culture for 24 hours. Luciferase activity was measured by adding 50 µl of Steady-Glo reagent (Promega) and samples were read in Victor V reader (PerkinElmer). The $IC_{50}$ values were calculated utilizing a maximum value corresponding to the amount of luciferase in the absence of a test compound and a minimum value corresponding to a test compound value obtained at maximum inhibition.

Determination of Normalized HEKT-bet IC50 values: Compounds were assayed in microtiter plates. Each plate included a reference compound which was ER-213038. The un-normalized $IC_{50}$ value for a particular compound was divided by the $IC_{50}$ value determined for the reference compound in the same microtiter plate to provide a relative potency value. The relative potency value was then multiplied by the established potency of the reference compound to provide the normalized HEKT-bet $IC_{50}$ value. In this assay, the established potency for ER-213038 was 0.190 µM. The $IC_{50}$ values provided herein were obtained using this normalization method.

HEKActin-luc assay: This assay measures actin promoter activity in engineered HEK cells that express an actin-luc reporter. HEKActin cells were plated at $1\times104$/well in 96-well plate and compound was added into cell culture for 24 hours. Luciferase activity was measured as described above. Some compounds of the present invention were tested in this assay.

JurkatIL4 assay: This assay measures IL4 promoter activity in Jurkat cells that are stably express IL4-luc. Luciferase activity was measured as described above after 24 hours stimulation of cells with PMA and ionomycin. Some compounds of the present invention were tested in this assay.

EL4T-bet assay: This assay measures a T-bet dependent endogenous IFNγ production in engineered EL4 cells that express a human T-bet. Cells were first incubated with compound or controls for 15 minutes. PMA was then added into culture medium. Supernatants were collected after 48 hours stimulation and IFNγ level was measure by ELISA (Endogen kit). Some compounds of the present invention were tested in this assay.

In vitro mouse Th differentiation assay. Naïve CD4 T cells were purified from TCR transgenic DO11.10 mice by magnetic cell sorting system (Miltenyi Biotec). Isolated cells were seeded at $1\times10^5$ CD4 T cells/$5\times10^5$ feeder cells/200 µl/well in 96 well flat bottom plates on day zero. Cells were cultured in Th0 (mIL2 10 ng/ml, OVA peptide 0.3 µg/ml), Th1 (mIL2 10 ng/ml, OVA peptide 0.3 µg/ml, mIL12 5 ng/ml and anti-IL4 Ab 10 µg/ml) and Th2 (mIL2 10 ng/ml, OVA peptide 0.3 µg/ml, mIL4 10 ng/ml and anti-IFNγ Ab 10 µg/ml) condition respectively with compounds. On day 3, cells were split equally into 3 cultures with a final culture volume of 200 µl incubated for 3 more days. The cell number was counted on day 6 and $1\times10^6$/ml cells were re-stimulated on anti-CD3 pre-coated plate (10 µg/ml) for 24 hours. Supernatants were collected for cytokine analysis by ELISA. Alamar blue was added to the remaining cell cultures for another 24 hrs to monitor T cell proliferation/toxicity. Some compounds of the present invention were tested in this assay.

B cell IgG2a/IgG1 secretion assay. Naive B cells were purified from BALB/c mice by magnetic cell sorting system (Miltenyi Biotec) and were seeded at $1\times10^5$ cells/well in a 96 well flat bottom plate on day 0. Cells were stimulated for 6 days with 25 µg/ml of LPS with 100 ng/ml of IFNγ for IgG2a production or 25 µg/ml of LPS with 10 ng/ml of IL4 for IgG1 production. Supernatants were collected on day 6 for ELISA analysis of IgG2a/IgG1 level. Alamar blue was added to the remaining cell cultures and cultured 4 more hours to monitor B cell proliferation/toxicity. Some compounds of the present invention were tested in this assay.

Exemplary compounds of the present invention were assayed according to the methods set forth above in the HEKT-bet-luc assay described above. Table 2 below sets forth examplary compounds of the present invention having an $IC_{50}$ of up to about 2.0 µM as determined by the HEKT-bet-luc assay described above at paragraph [0105].

TABLE 2

IC$_{50}$ Data of Exemplary Compounds

| Example # | ER # | IC$_{50}$ (μM) |
|---|---|---|
| 39 | ER-818561 | 0.025 |
| 40 | ER-813499 | 0.036 |
| 41 | ER-818558 | 0.045 |
| 42 | ER-813081 | 0.058 |
| 43 | ER-813508 | 0.059 |
| 44 | ER-813509 | 0.059 |
| 45 | ER-818528 | 0.062 |
| 46 | ER-813493 | 0.066 |
| 47 | ER-818560 | 0.078 |
| 48 | ER-813411 | 0.081 |
| 49 | ER-819711 | 0.083 |
| 50 | ER-817116 | 0.089 |
| 51 | ER-813410 | 0.102 |
| 52 | ER-818554 | 0.106 |
| 53 | ER-813511 | 0.110 |
| 54 | ER-812605 | 0.112 |
| 55 | ER-817118 | 0.112 |
| 56 | ER-819695 | 0.128 |
| 57 | ER-818550 | 0.150 |
| 58 | ER-813512 | 0.151 |
| 59 | ER-813491 | 0.163 |
| 60 | ER-813443 | 0.193 |
| 61 | ER-819680 | 0.232 |
| 62 | ER-817198 | 0.244 |

TABLE 2-continued

IC$_{50}$ Data of Exemplary Compounds

| Example # | ER # | IC$_{50}$ (μM) |
|---|---|---|
| 63 | ER-818543 | 0.264 |
| 64 | ER-812282 | 0.267 |
| 65 | ER-812428 | 0.284 |
| 66 | ER-813317 | 0.285 |
| 67 | ER-817088 | 0.346 |
| 68 | ER-818547 | 0.389 |
| 69 | ER-813280 | 0.603 |
| 70 | ER-812682 | 0.727 |
| 71 | ER-817079 | 0.835 |
| 72 | ER-812274 | 0.845 |
| 73 | ER-813273 | 0.914 |
| 74 | ER-819697 | 0.936 |
| 75 | ER-817165 | 1.055 |
| 76 | ER-813111 | 1.143 |
| 77 | ER-812430 | 1.238 |
| 78 | ER-813209 | 1.390 |
| 79 | ER-812556 | 1.460 |
| 80 | ER-812515 | 1.654 |

Table 3 below sets forth examplary compounds of the present invention having an IC$_{50}$ of 0.6 to 2.0 μM as determined by the HEKT-bet-luc assay described above at paragraph [0105].

TABLE 3

IC$_{50}$ Data of Exemplary Compounds

| Example # | Structure | ER # | IC$_{50}$ (μM) |
|---|---|---|---|
| 81 | 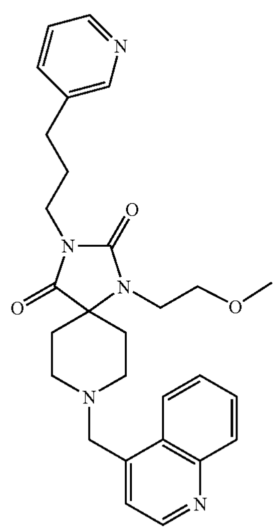 | ER-817148 | 0.650 |
| 82 | 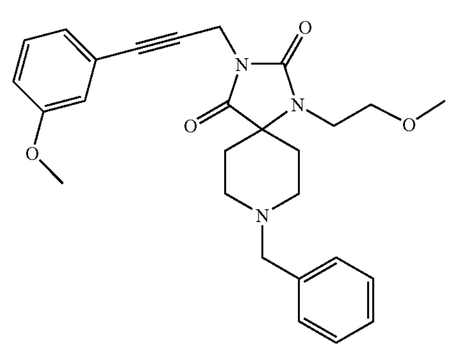 | ER-813445 | 0.650 |

TABLE 3-continued
IC$_{50}$ Data of Exemplary Compounds
| Example # | Structure | ER # | IC$_{50}$ (μM) |
|---|---|---|---|
| 83 | 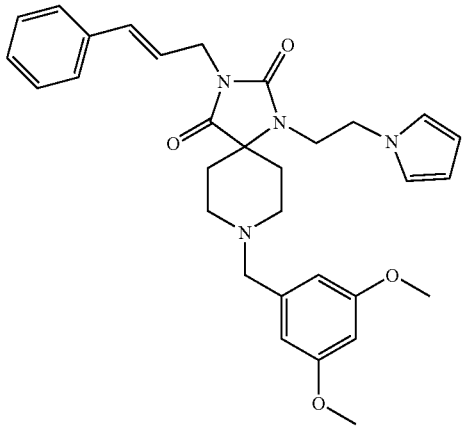 | ER-818523 | 0.667 |
| 84 | 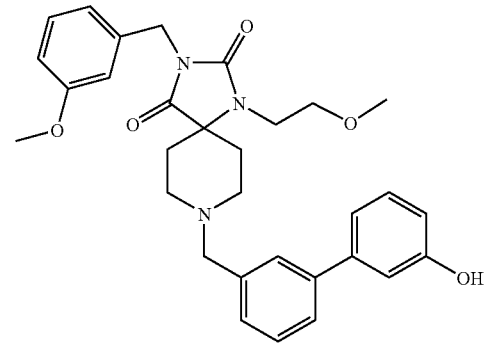 | ER-813125 | 0.681 |
| 85 | 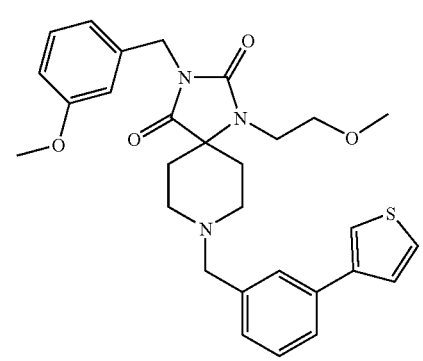 | ER-813137 | 0.750 |

TABLE 3-continued
IC$_{50}$ Data of Exemplary Compounds
| Example # | Structure | ER # | IC$_{50}$ (µM) |
|---|---|---|---|
| 86 | 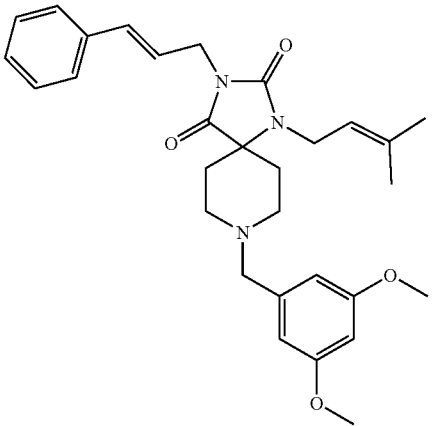 | ER-818530 | 0.757 |
| 87 | 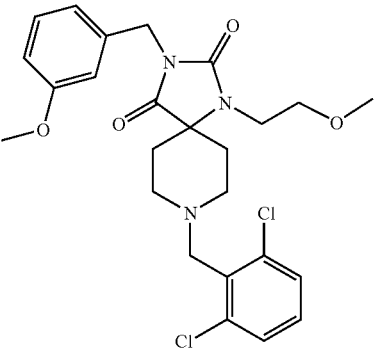 | ER-812465 | 0.782 |
| 88 | 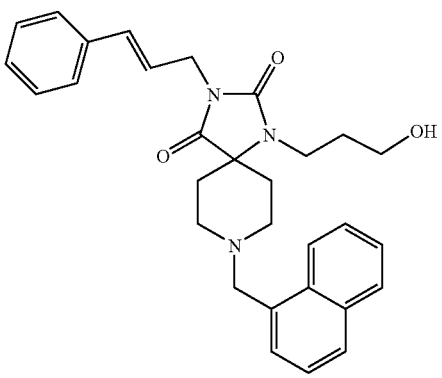 | ER-818519 | 0.798 |

TABLE 3-continued
IC₅₀ Data of Exemplary Compounds
| Example # | Structure | ER # | IC$_{50}$ (µM) |
|---|---|---|---|
| 89 | 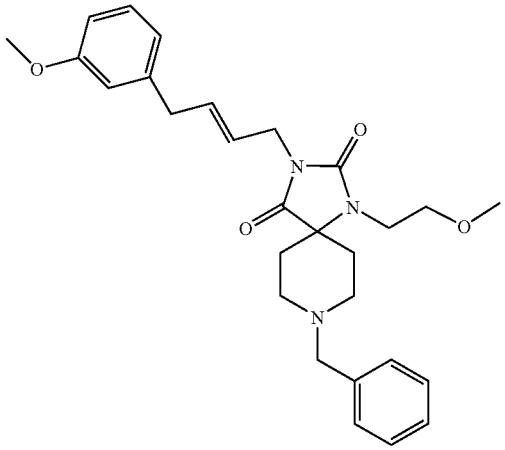 | ER-817079 | 0.835 |
| 90 | 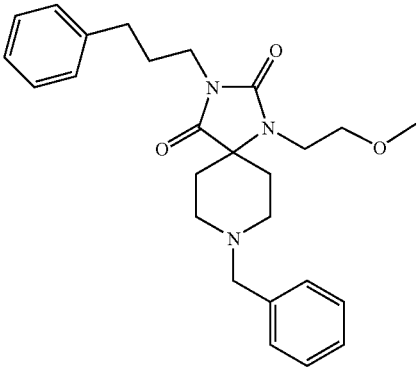 | ER-813046 | 0.838 |
| 91 | 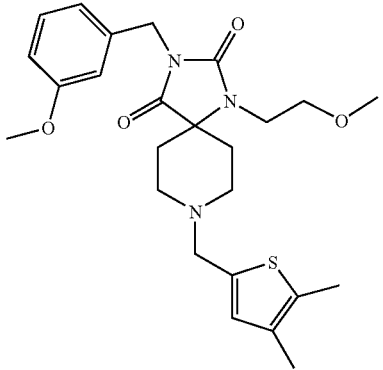 | ER-812274 | 0.845 |

TABLE 3-continued
IC₅₀ Data of Exemplary Compounds
| Example # | Structure | ER # | IC$_{50}$ (μM) |
|---|---|---|---|
| 92 | 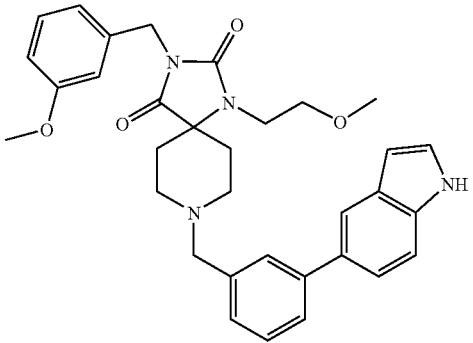 | ER-813140 | 0.868 |
| 93 | 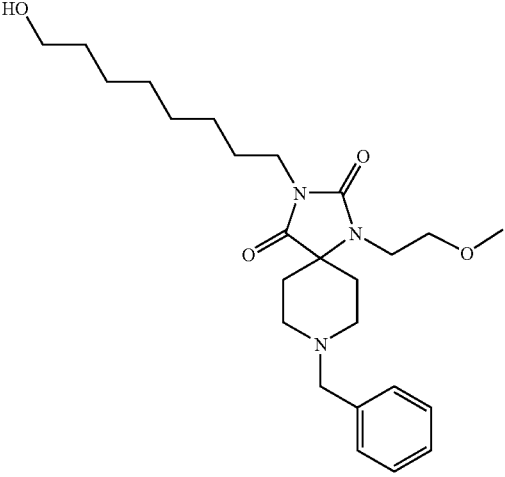 | ER-813273 | 0.914 |
| 94 | 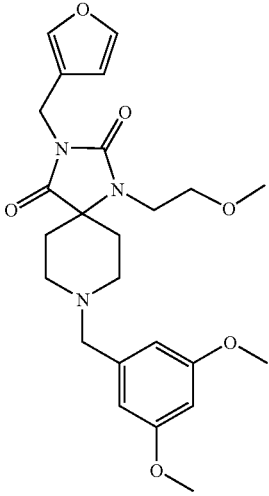 | ER-819697 | 0.936 |

TABLE 3-continued

IC$_{50}$ Data of Exemplary Compounds

| Example # | Structure | ER # | IC$_{50}$ (μM) |
|---|---|---|---|
| 95 | 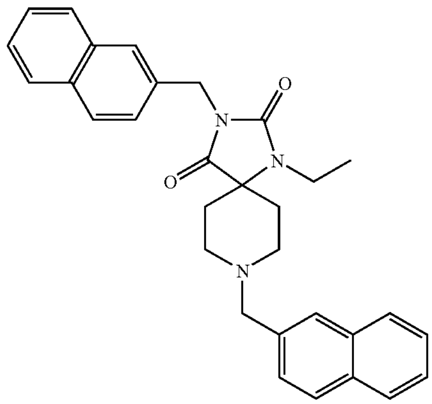 | ER-813541 | 0.970 |
| 96 | 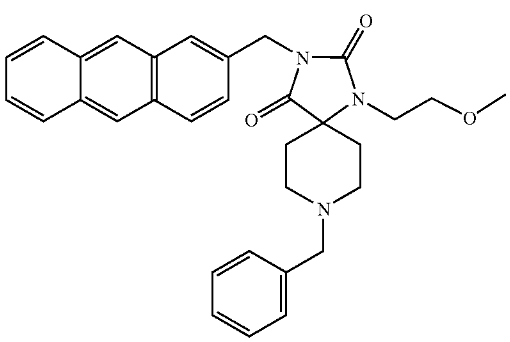 | ER-813365 | 1.034 |
| 97 | 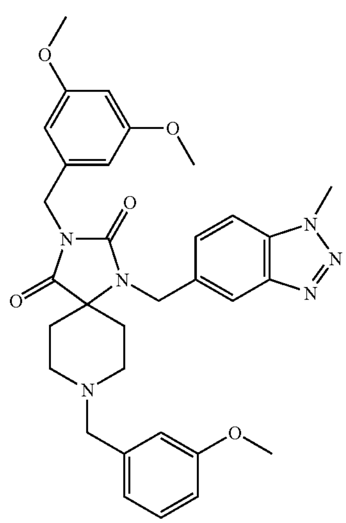 | ER-817131 | 1.077 |

TABLE 3-continued

IC$_{50}$ Data of Exemplary Compounds

| Example # | Structure | ER # | IC$_{50}$ (μM) |
|---|---|---|---|
| 98 | 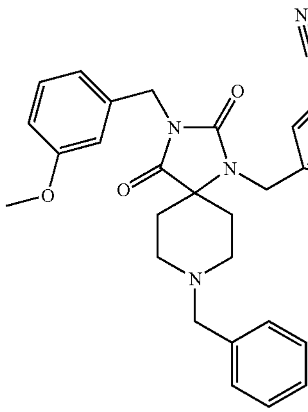 | ER-813169 | 1.099 |
| 99 | 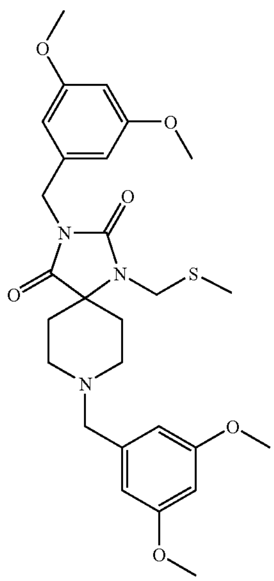 | ER-817115 | 1.150 |
| 100 | 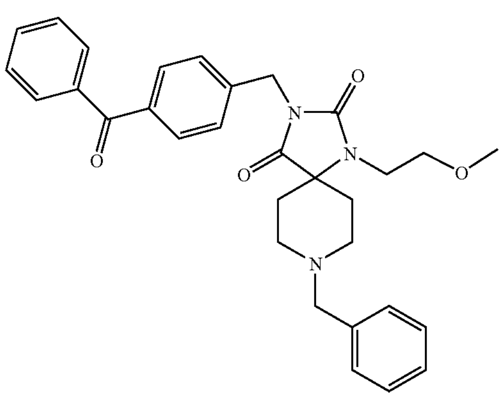 | ER-813271 | 1.238 |

TABLE 3-continued
IC$_{50}$ Data of Exemplary Compounds
| Example # | Structure | ER # | IC$_{50}$ (µM) |
|---|---|---|---|
| 101 | 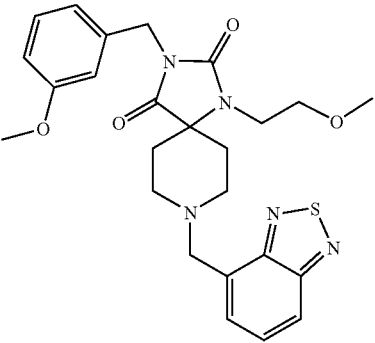 | ER-812430 | 1.238 |
| 102 | 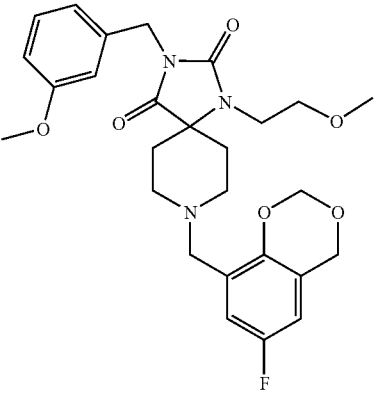 | ER-818583 | 1.315 |
| 103 | 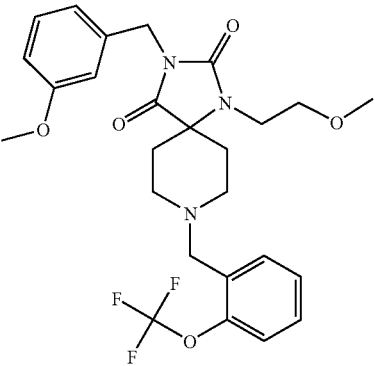 | ER-812330 | 1.345 |
| 104 | 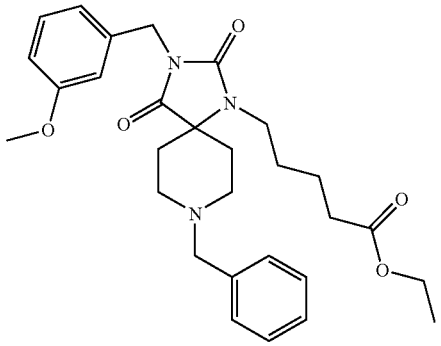 | ER-813209 | 1.390 |

TABLE 3-continued
IC₅₀ Data of Exemplary Compounds
| Example # | Structure | ER # | IC₅₀ (µM) |
|---|---|---|---|
| 105 | 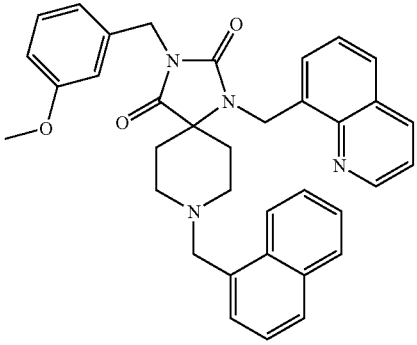 | ER-818563 | 1.394 |
| 106 | 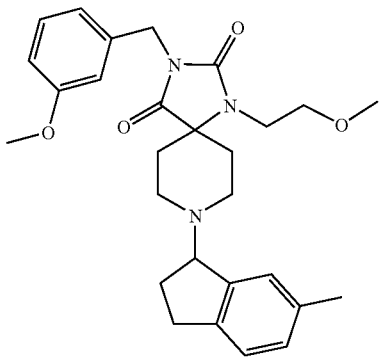 | ER-813380 | 1.423 |
| 107 | 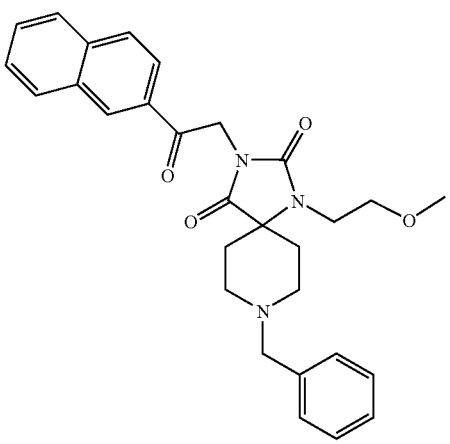 | ER-812556 | 1.460 |

TABLE 3-continued

IC$_{50}$ Data of Exemplary Compounds

| Example # | Structure | ER # | IC$_{50}$ (μM) |
| --- | --- | --- | --- |
| 108 | 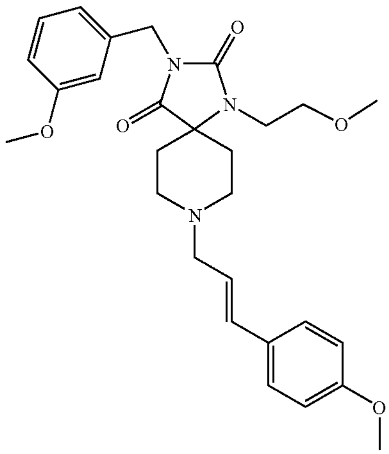 | ER-813112 | 1.475 |
| 109 | 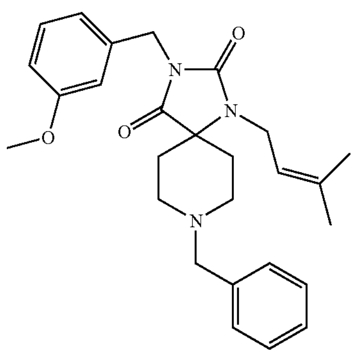 | ER-813146 | 1.519 |
| 110 | 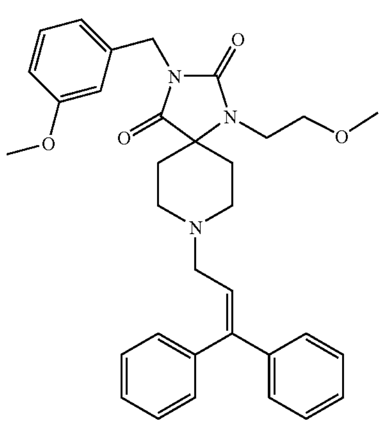 | ER-813107 | 1.544 |

TABLE 3-continued
IC$_{50}$ Data of Exemplary Compounds
| Example # | Structure | ER # | IC$_{50}$ (μM) |
|---|---|---|---|
| 111 | 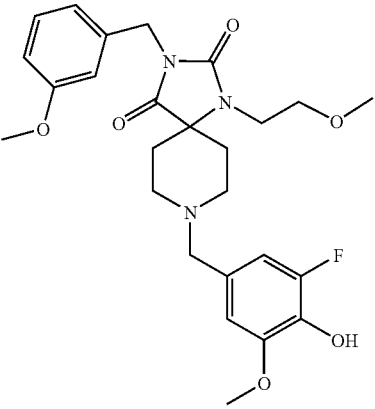 | ER-817181 | 1.551 |
| 112 | 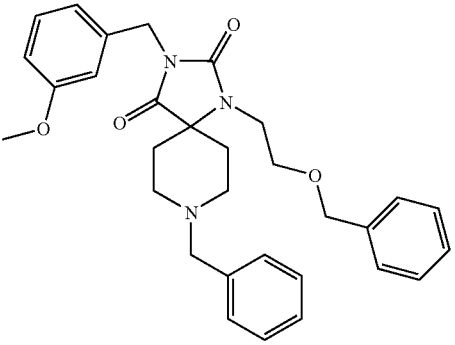 | ER-813153 | 1.566 |
| 113 | 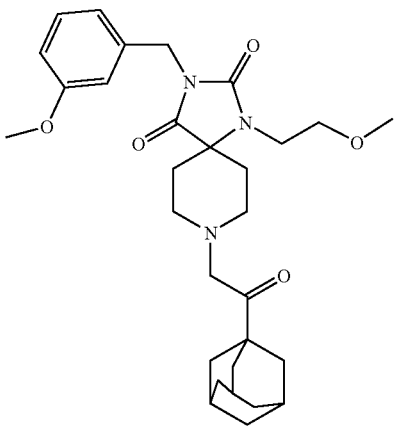 | ER-812515 | 1.654 |

TABLE 3-continued

IC₅₀ Data of Exemplary Compounds

| Example # | Structure | ER # | IC$_{50}$ (µM) |
|---|---|---|---|
| 114 | 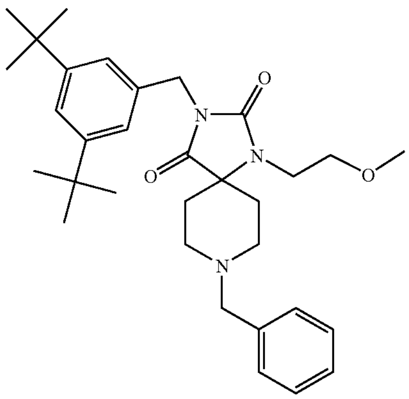 | ER-813353 | 1.743 |
| 115 | 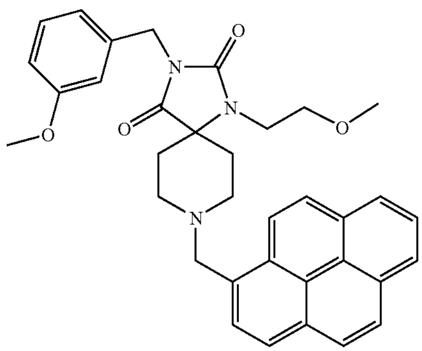 | ER-813109 | 1.813 |
| 116 | 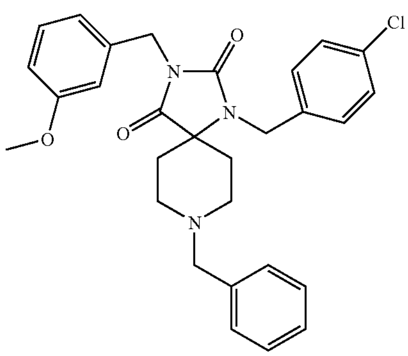 | ER-813198 | 1.833 |
| 117 | 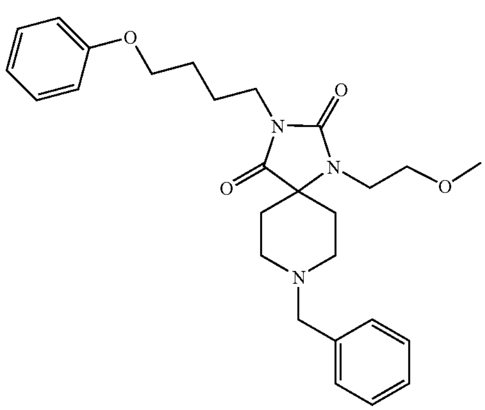 | ER-812544 | 1.837 |

TABLE 3-continued

IC₅₀ Data of Exemplary Compounds

| Example # | Structure | ER # | IC₅₀ (μM) |
|---|---|---|---|
| 118 | 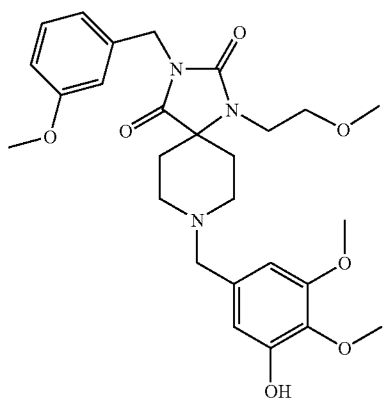 | ER-817176 | 1.876 |
| 119 | 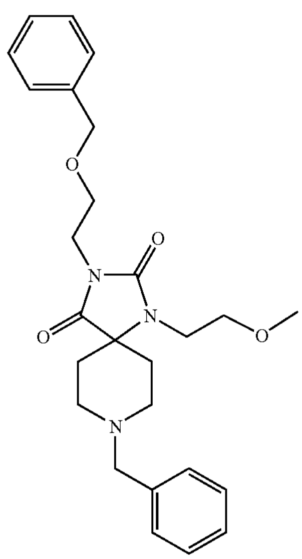 | ER-812546 | 1.926 |
| 120 | 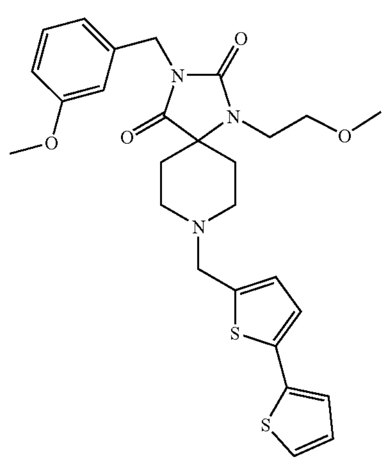 | ER-812275 | 1.992 |

Table 4 below sets forth examplary compounds of the present invention having an $IC_{50}$ of up to 0.6 μM as determined by the HEKT-bet-luc assay described above at paragraph [0105].

TABLE 4

$IC_{50}$ Data of Exemplary Compounds

| Example # | Structure | ER # | $IC_{50}$ (μM) |
|---|---|---|---|
| 121 | 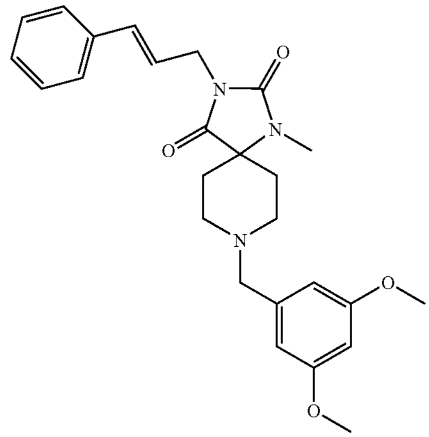 | ER-818561 | 0.025 |
| 122 | 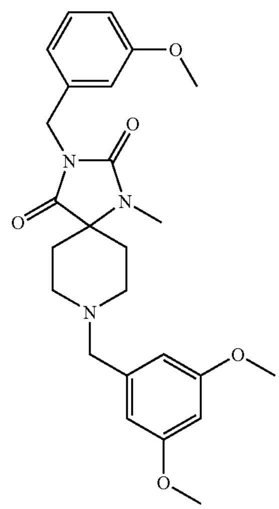 | ER-817135 | 0.037 |
| 123 | 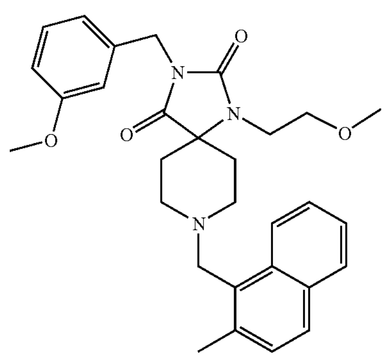 | ER-813077 | 0.060 |

TABLE 4-continued

IC₅₀ Data of Exemplary Compounds

| Example # | Structure | ER # | IC$_{50}$ (µM) |
|---|---|---|---|
| 124 | 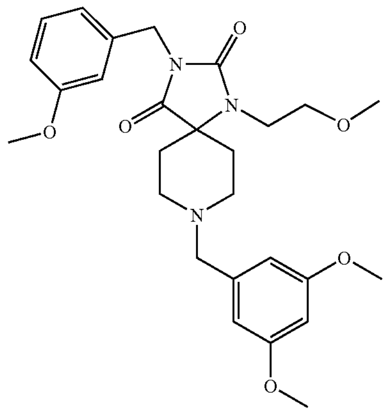 | ER-818574 | 0.064 |
| 125 | 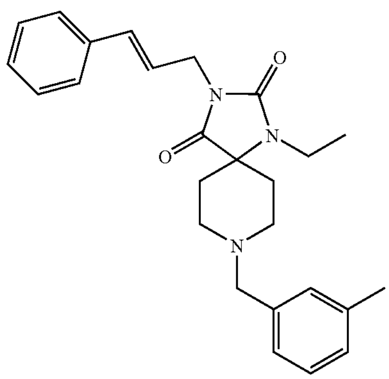 | ER-813510 | 0.068 |
| 126 | 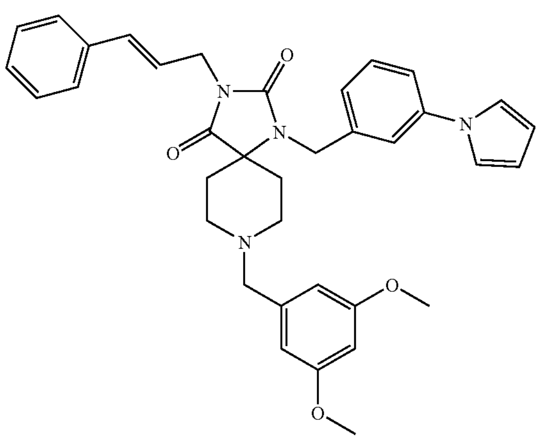 | ER-818559 | 0.073 |

TABLE 4-continued

IC$_{50}$ Data of Exemplary Compounds

| Example # | Structure | ER # | IC$_{50}$ (μM) |
|---|---|---|---|
| 127 | 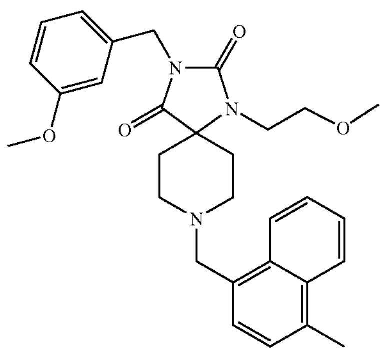 | ER-813078 | 0.082 |
| 128 | 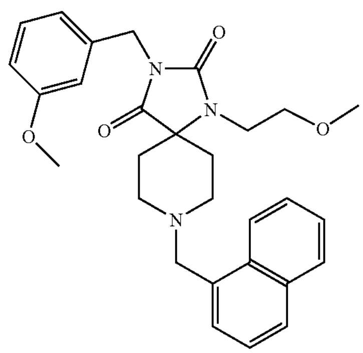 | ER-813521 | 0.086 |
| 129 | 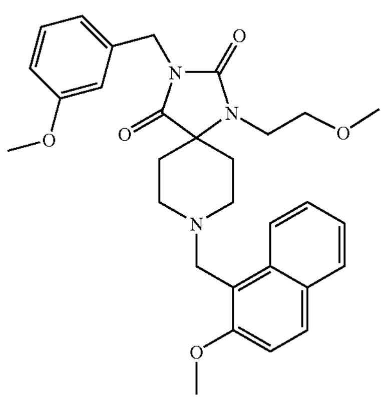 | ER-813080 | 0.094 |
| 130 | 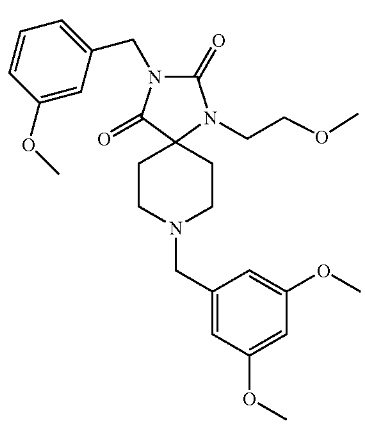 | ER-513519 | 0.098 |

TABLE 4-continued

IC$_{50}$ Data of Exemplary Compounds

| Example # | Structure | ER # | IC$_{50}$ (μM) |
|---|---|---|---|
| 131 | 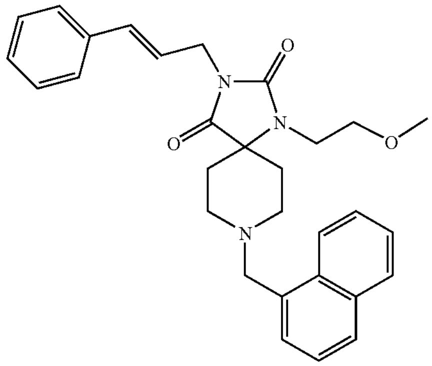 | ER-813492 | 0.100 |
| 132 | 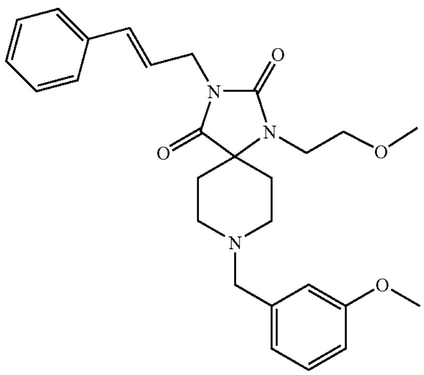 | ER-813452 | 0.101 |
| 133 | 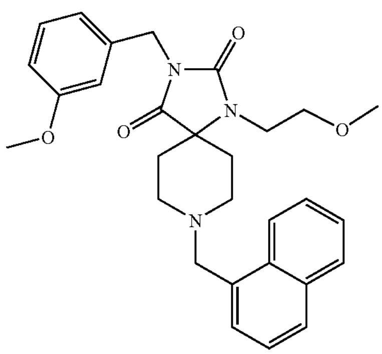 | ER-818568 | 0.119 |
| 134 | 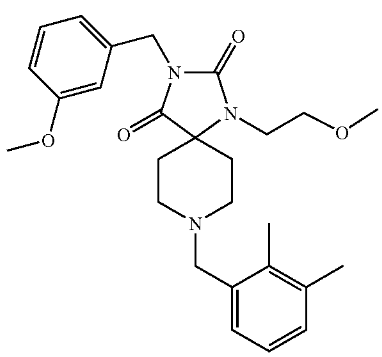 | ER-813091 | 0.120 |

TABLE 4-continued
IC$_{50}$ Data of Exemplary Compounds
| Example # | Structure | ER # | IC$_{50}$ (µM) |
| --- | --- | --- | --- |
| 135 | 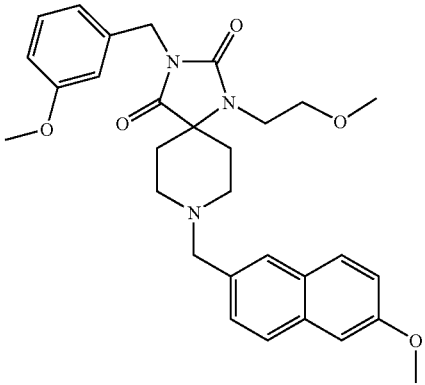 | ER-813075 | 0.123 |
| 136 | 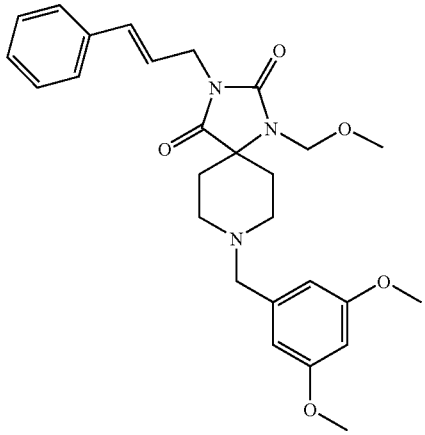 | ER-818562 | 0.124 |
| 137 | 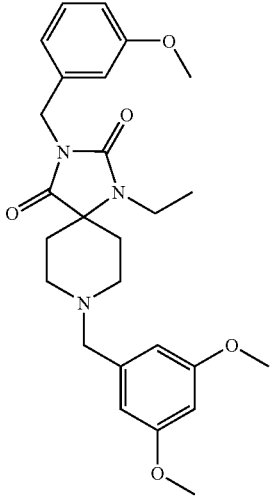 | ER-817137 | 0.124 |

TABLE 4-continued
IC$_{50}$ Data of Exemplary Compounds
| Example # | Structure | ER # | IC$_{50}$ (μM) |
|---|---|---|---|
| 138 | 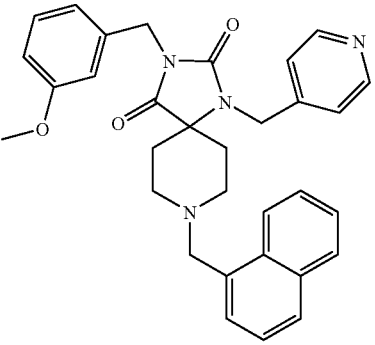 | ER-818535 | 0.125 |
| 139 | 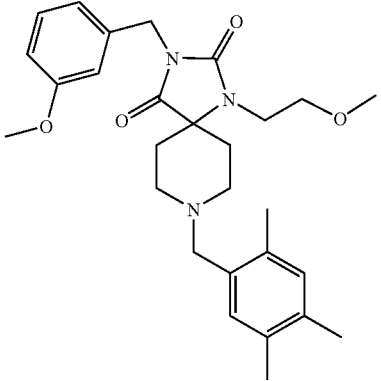 | ER-813096 | 0.125 |
| 140 | 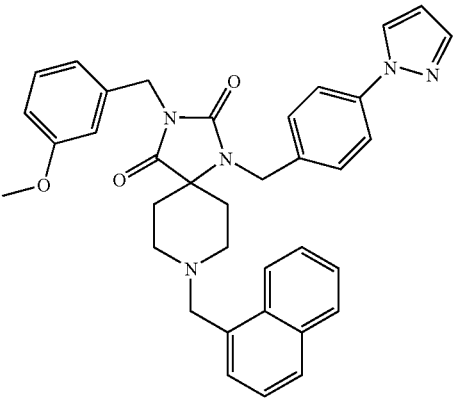 | ER-818564 | 0.127 |
| 141 | 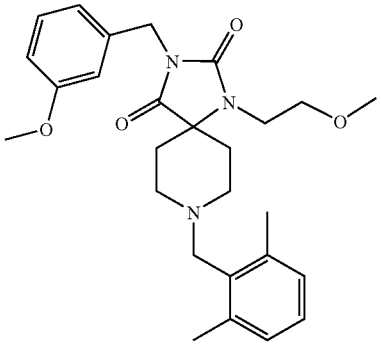 | ER-813092 | 0.130 |

TABLE 4-continued
IC50 Data of Exemplary Compounds
| Example # | Structure | ER # | IC50 (μM) |
|---|---|---|---|
| 142 | 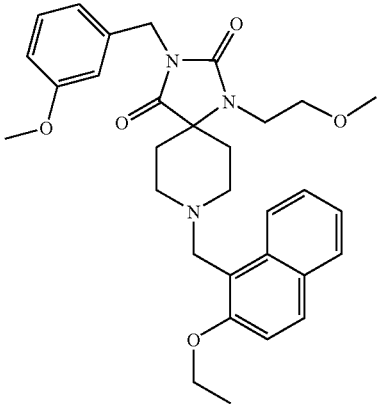 | ER-813082 | 0.130 |
| 143 | 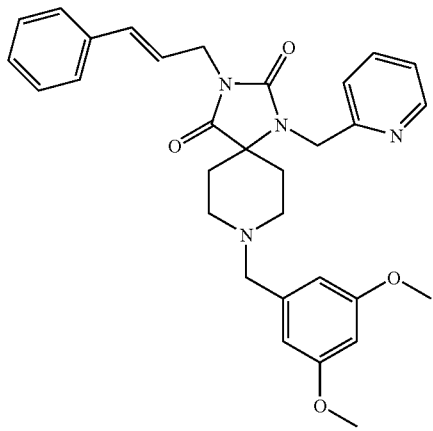 | ER-818524 | 0.134 |
| 144 | 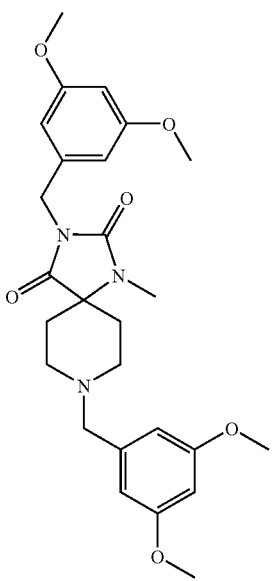 | ER-817119 | 0.134 |

TABLE 4-continued
IC$_{50}$ Data of Exemplary Compounds
| Example # | Structure | ER # | IC$_{50}$ (µM) |
|---|---|---|---|
| 145 | 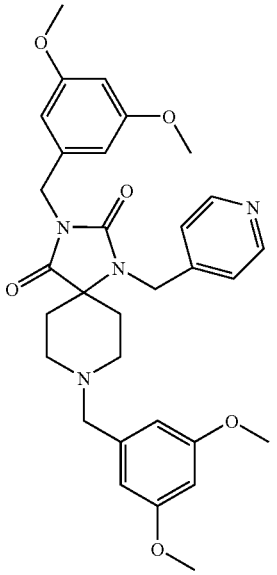 | ER-817117 | 0.139 |
| 146 | 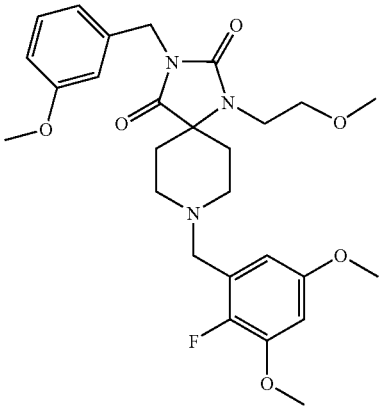 | ER-820087 | 0.142 |
| 147 | 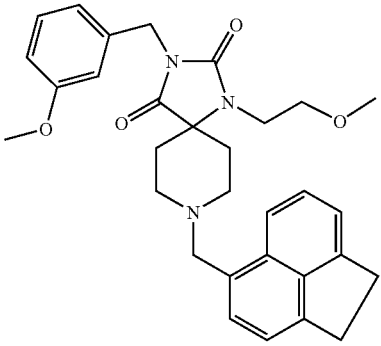 | ER-813079 | 0.142 |

TABLE 4-continued

IC$_{50}$ Data of Exemplary Compounds

| Example # | Structure | ER # | IC$_{50}$ (μM) |
|---|---|---|---|
| 148 | 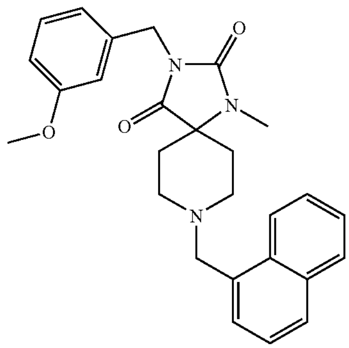 | ER-818567 | 0.143 |
| 149 | 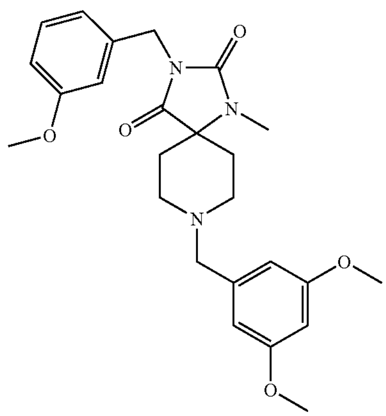 | ER-818573 | 0.145 |
| 150 | 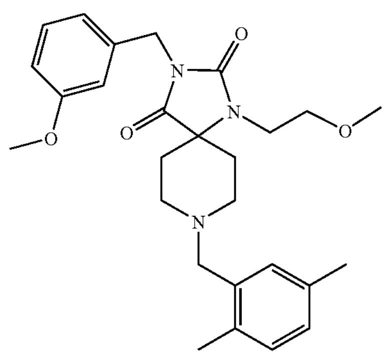 | ER-813089 | 0.147 |
| 151 | 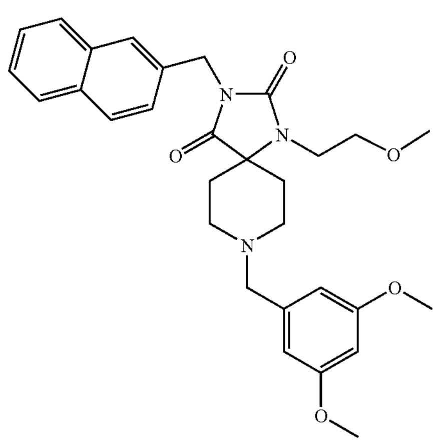 | ER-813529 | 0.148 |

TABLE 4-continued

IC₅₀ Data of Exemplary Compounds

| Example # | Structure | ER # | IC$_{50}$ (µM) |
|---|---|---|---|
| 152 | 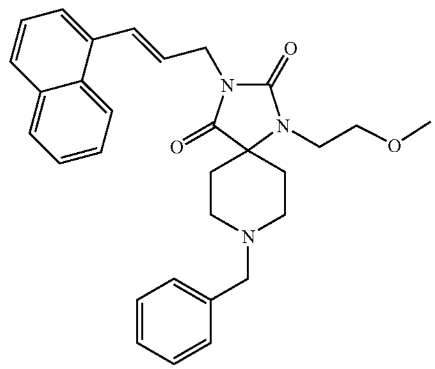 | ER-813414 | 0.149 |
| 153 | 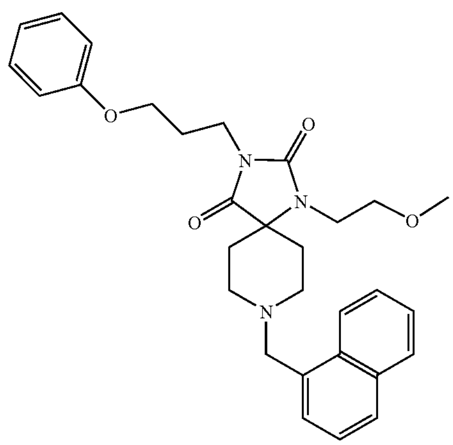 | ER-813516 | 0.151 |
| 154 | 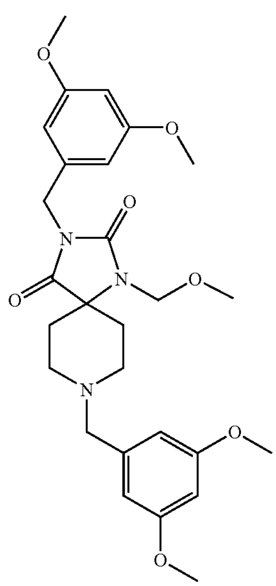 | ER-817114 | 0.153 |

TABLE 4-continued

IC$_{50}$ Data of Exemplary Compounds

| Example # | Structure | ER # | IC$_{50}$ (µM) |
|---|---|---|---|
| 155 | 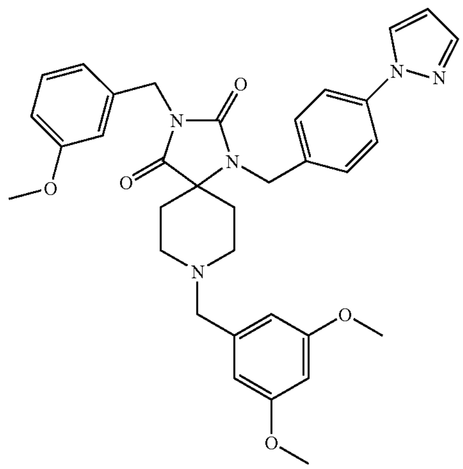 | ER-818570 | 0.159 |
| 156 | 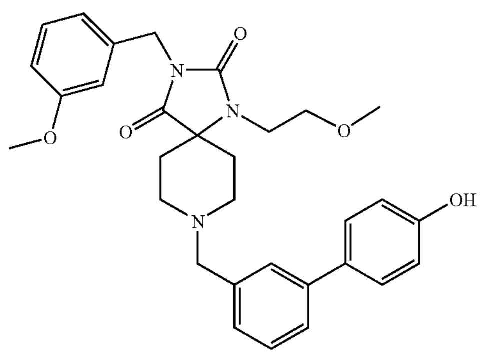 | ER-813126 | 0.159 |
| 157 | 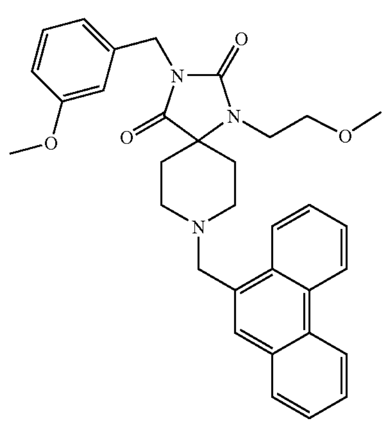 | ER-813083 | 0.161 |

TABLE 4-continued

IC$_{50}$ Data of Exemplary Compounds

| Example # | Structure | ER # | IC$_{50}$ (μM) |
|---|---|---|---|
| 158 | 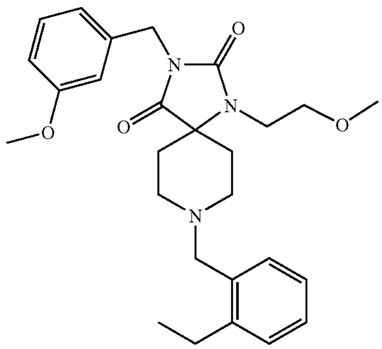 | ER-813094 | 0.164 |
| 159 | 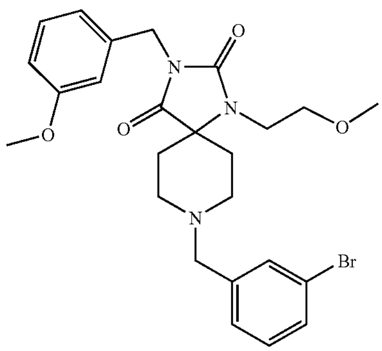 | ER-812619 | 0.166 |
| 160 | 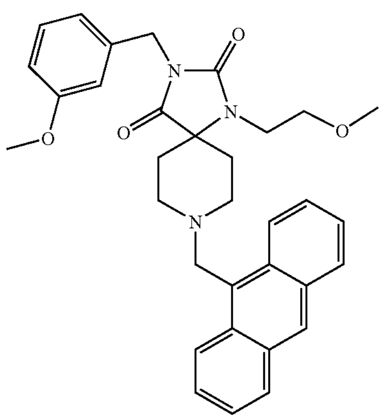 | ER-813084 | 0.168 |
| 161 | 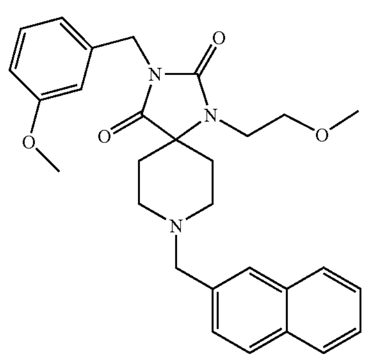 | ER-813522 | 0.169 |

TABLE 4-continued

IC$_{50}$ Data of Exemplary Compounds

| Example # | Structure | ER # | IC$_{50}$ (µM) |
|---|---|---|---|
| 162 | 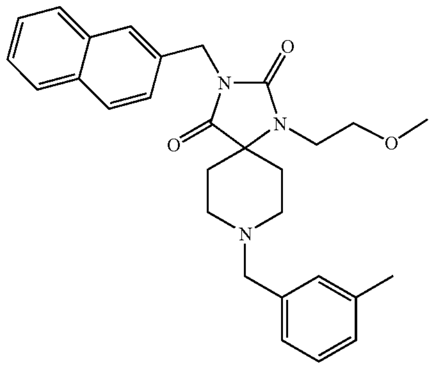 | ER-813530 | 0.172 |
| 163 | 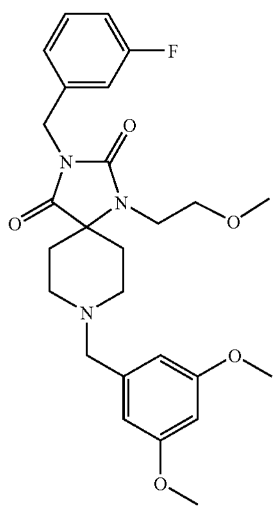 | ER-819670 | 0.182 |
| 164 | 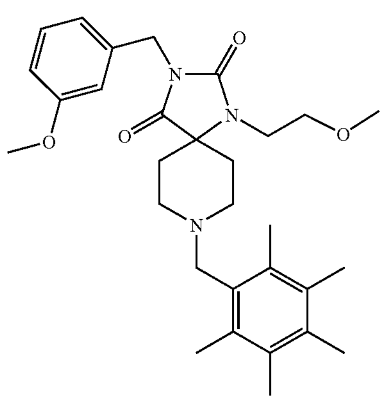 | ER-813216 | 0.182 |

TABLE 4-continued

IC₅₀ Data of Exemplary Compounds

| Example # | Structure | ER # | IC$_{50}$ (μM) |
|---|---|---|---|
| 165 | 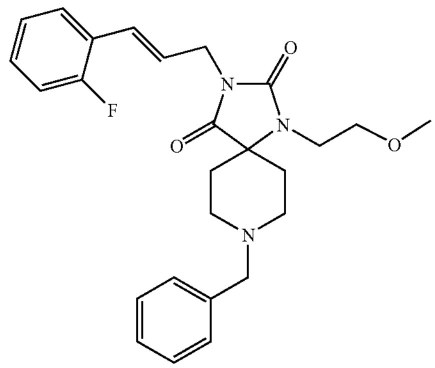 | ER-813408 | 0.183 |
| 166 | 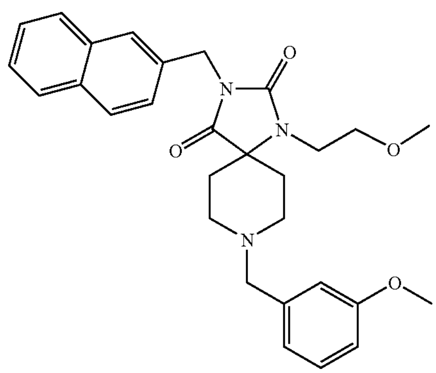 | ER-813528 | 0.184 |
| 167 | 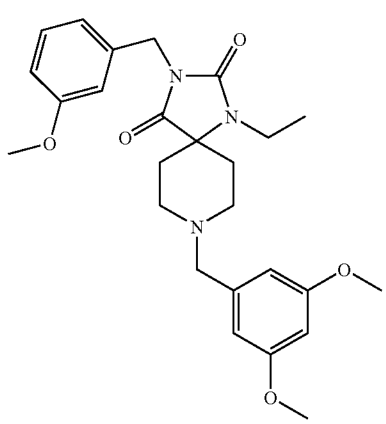 | ER-813543 | 0.187 |

TABLE 4-continued

IC$_{50}$ Data of Exemplary Compounds

| Example # | Structure | ER # | IC$_{50}$ (μM) |
|---|---|---|---|
| 168 | 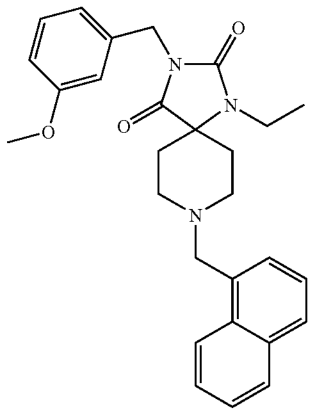 | ER-517010 | 0.190 |
| 169 | 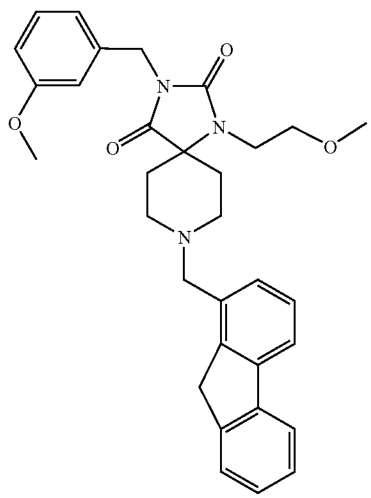 | ER-813073 | 0.190 |
| 170 | 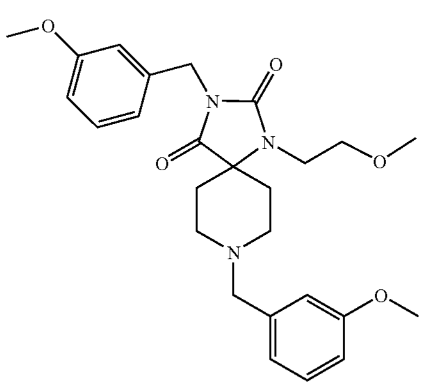 | ER-213038 | 0.190 |

TABLE 4-continued

IC$_{50}$ Data of Exemplary Compounds

| Example # | Structure | ER # | IC$_{50}$ (µM) |
|---|---|---|---|
| 171 | 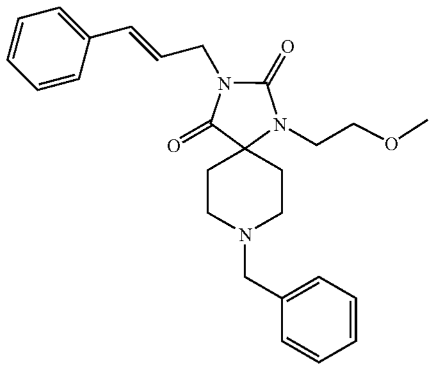 | ER-813369 | 0.191 |
| 172 | 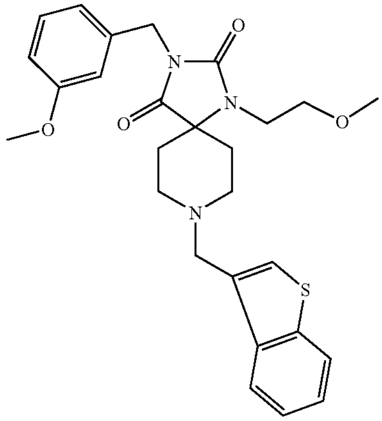 | ER-812276 | 0.193 |
| 173 | 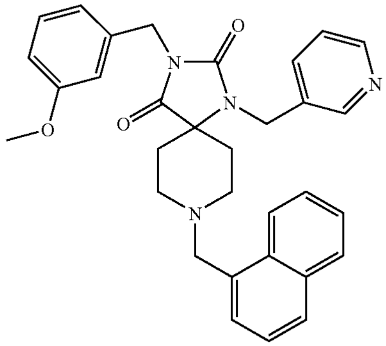 | ER-818536 | 0.196 |
| 174 | 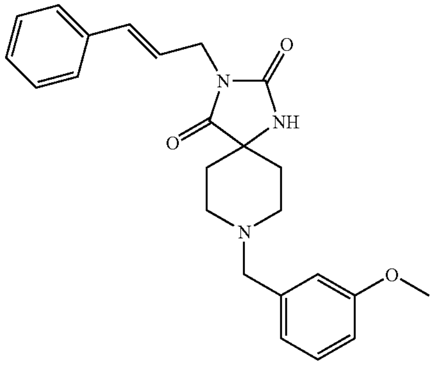 | ER-813453 | 0.198 |

TABLE 4-continued

IC$_{50}$ Data of Exemplary Compounds

| Example # | Structure | ER # | IC$_{50}$ (μM) |
|---|---|---|---|
| 175 | 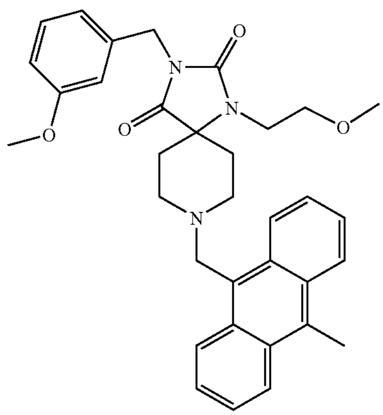 | ER-813087 | 0.200 |
| 176 | 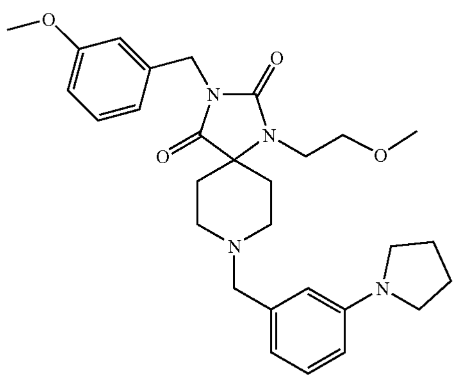 | ER-817052 | 0.203 |
| 177 | 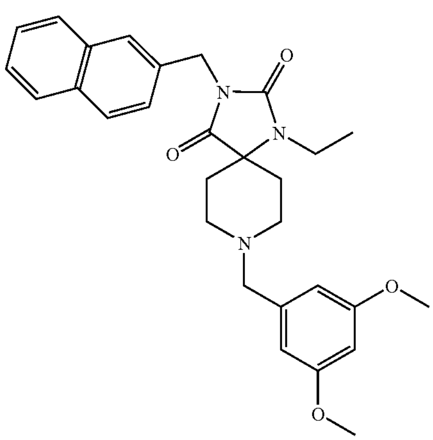 | ER-813538 | 0.205 |

TABLE 4-continued

IC$_{50}$ Data of Exemplary Compounds

| Example # | Structure | ER # | IC$_{50}$ (µM) |
|---|---|---|---|
| 178 | 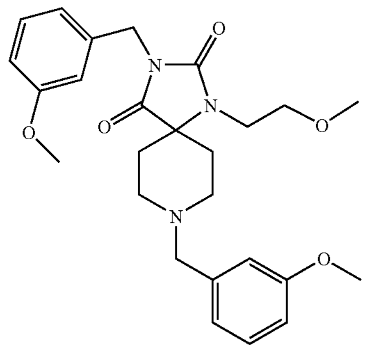 | ER-813518 | 0.205 |
| 179 | 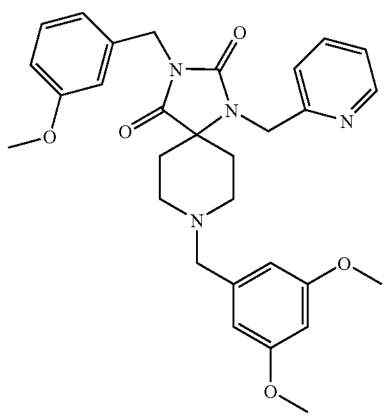 | ER-818544 | 0.215 |
| 180 | 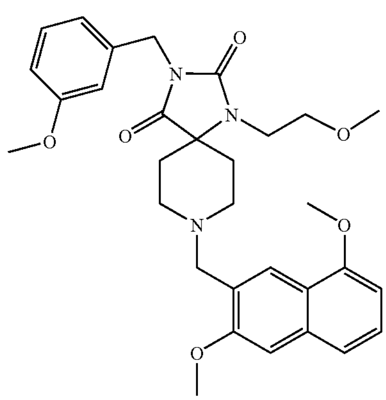 | ER-813076 | 0.223 |

TABLE 4-continued
IC₅₀ Data of Exemplary Compounds
| Example # | Structure | ER # | IC₅₀ (μM) |
|---|---|---|---|
| 181 | 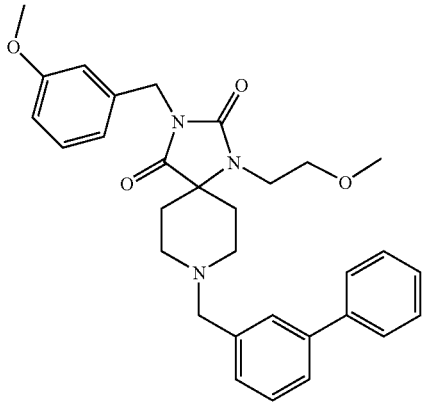 | ER-817034 | 0.225 |
| 182 | 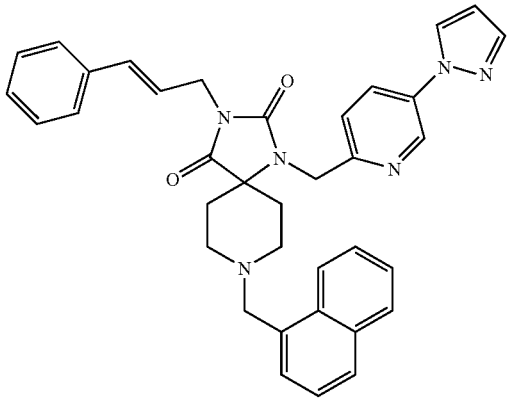 | ER-818552 | 0.226 |
| 183 | 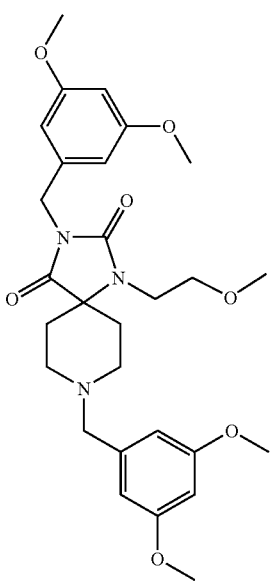 | ER-817110 | 0.230 |

TABLE 4-continued

IC$_{50}$ Data of Exemplary Compounds

| Example # | Structure | ER # | IC$_{50}$ (µM) |
|---|---|---|---|
| 184 | 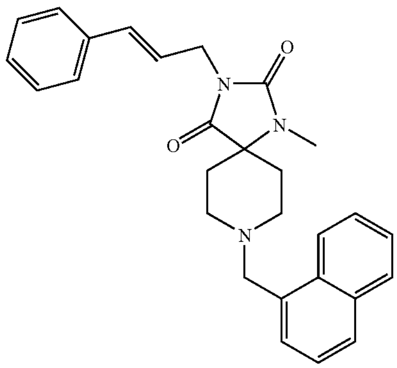 | ER-818555 | 0.235 |
| 185 | 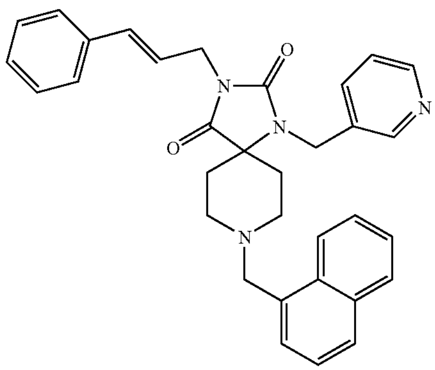 | ER-818516 | 0.235 |
| 186 | 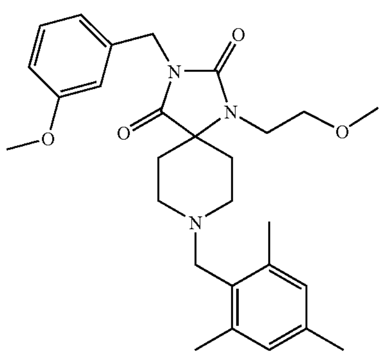 | ER-813214 | 0.236 |
| 187 | 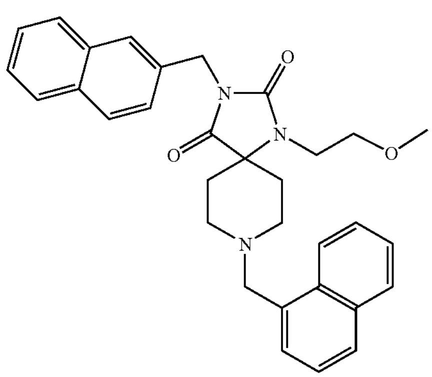 | ER-813531 | 0.243 |

TABLE 4-continued

IC$_{50}$ Data of Exemplary Compounds

| Example # | Structure | ER # | IC$_{50}$ (µM) |
|---|---|---|---|
| 188 | 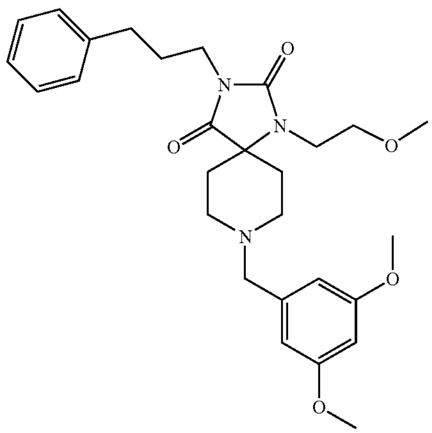 | ER-813495 | 0.246 |
| 189 | 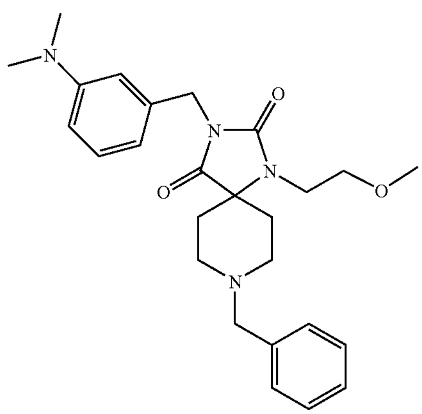 | ER-817032 | 0.247 |
| 190 | 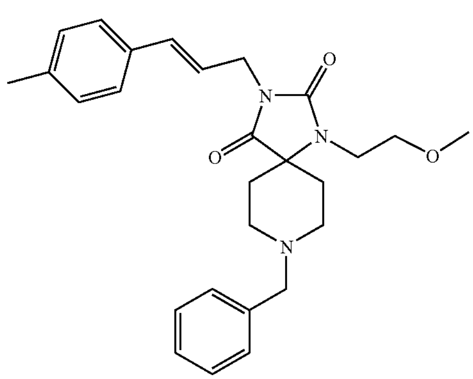 | ER-813407 | 0.251 |

TABLE 4-continued

IC$_{50}$ Data of Exemplary Compounds

| Example # | Structure | ER # | IC$_{50}$ (μM) |
|---|---|---|---|
| 191 | 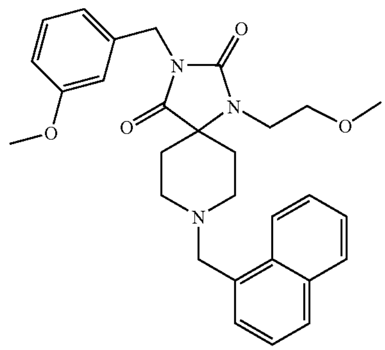 | ER-812461 | 0.253 |
| 192 | 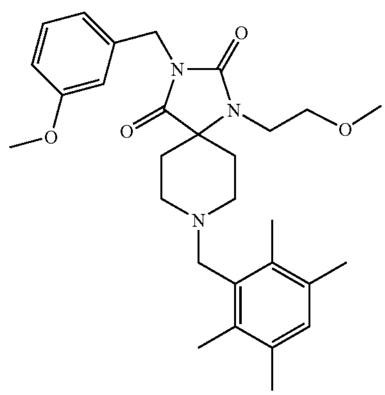 | ER-813215 | 0.260 |
| 193 | 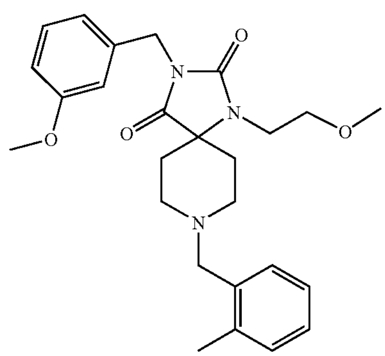 | ER-812287 | 0.261 |
| 194 | 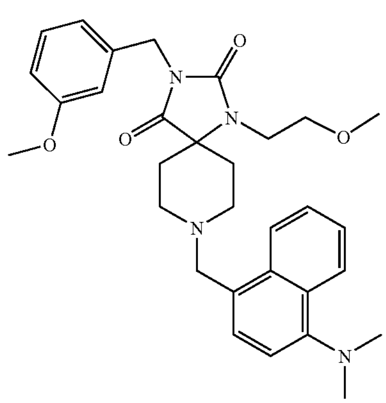 | ER-813103 | 0.262 |

TABLE 4-continued

IC$_{50}$ Data of Exemplary Compounds

| Example # | Structure | ER # | IC$_{50}$ (μM) |
|---|---|---|---|
| 195 | 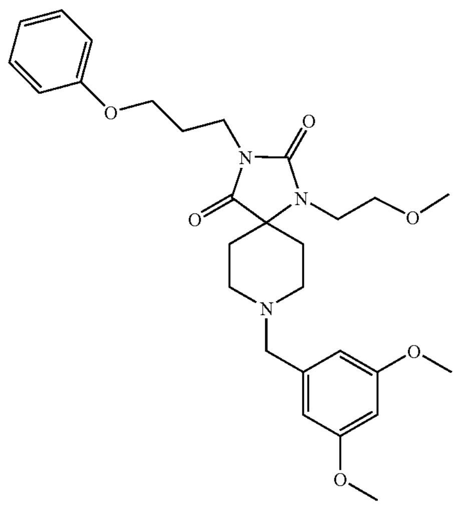 | ER-813514 | 0.264 |
| 196 | 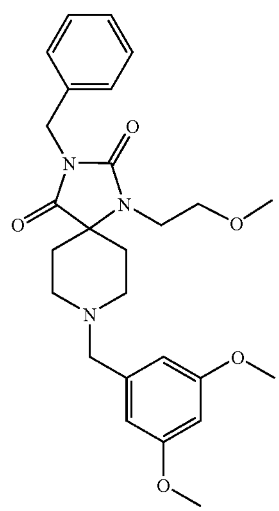 | ER-819675 | 0.268 |
| 197 | 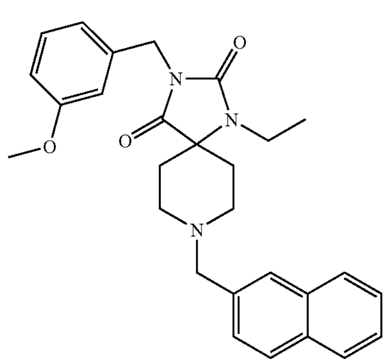 | ER-817011 | 0.270 |

TABLE 4-continued

IC$_{50}$ Data of Exemplary Compounds

| Example # | Structure | ER # | IC$_{50}$ (μM) |
|---|---|---|---|
| 198 | 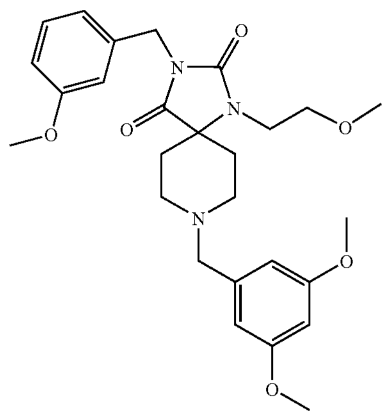 | ER-812321 | 0.270 |
| 199 | 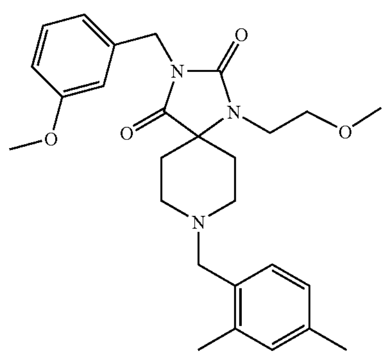 | ER-813213 | 0.279 |
| 200 | 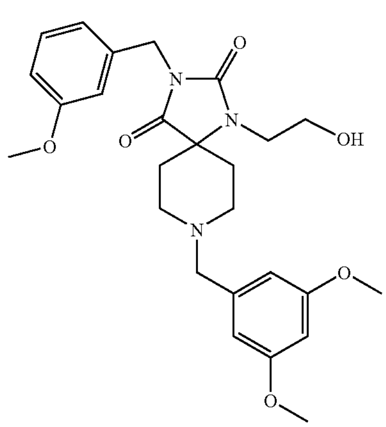 | ER-818548 | 0.285 |

TABLE 4-continued
IC$_{50}$ Data of Exemplary Compounds
| Example # | Structure | ER # | IC$_{50}$ (μM) |
|---|---|---|---|
| 201 | 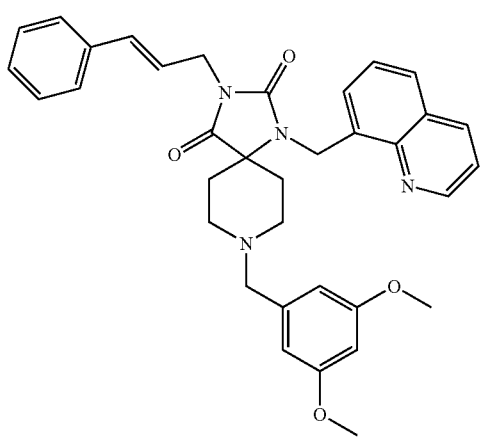 | ER-818557 | 0.288 |
| 202 | 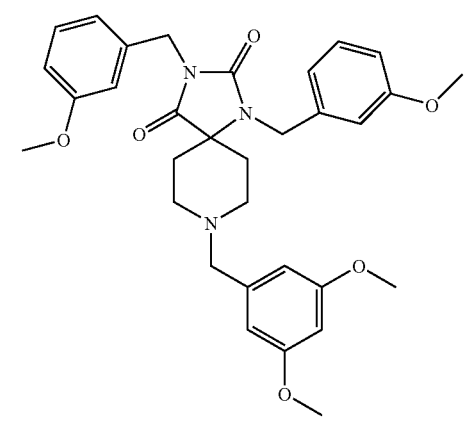 | ER-818542 | 0.290 |
| 203 | 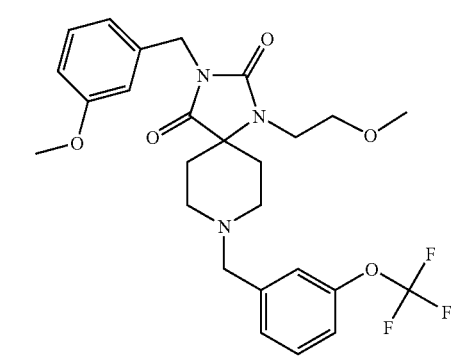 | ER-812609 | 0.291 |

TABLE 4-continued

IC$_{50}$ Data of Exemplary Compounds

| Example # | Structure | ER # | IC$_{50}$ (µM) |
|---|---|---|---|
| 204 | 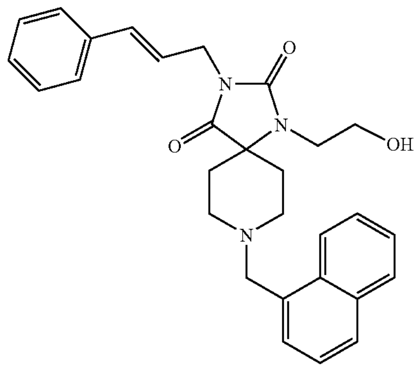 | ER-818518 | 0.298 |
| 205 | 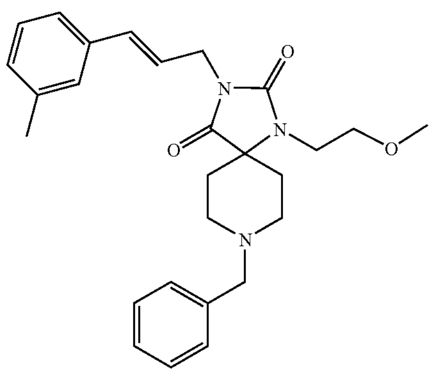 | ER-813406 | 0.298 |
| 206 | 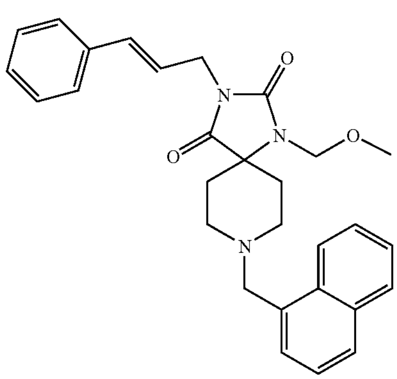 | ER-818556 | 0.311 |

TABLE 4-continued
IC$_{50}$ Data of Exemplary Compounds
| Example # | Structure | ER # | IC$_{50}$ (μM) |
|---|---|---|---|
| 207 | 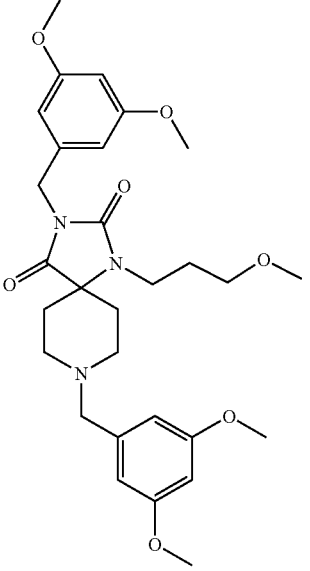 | ER-817111 | 0.317 |
| 208 | 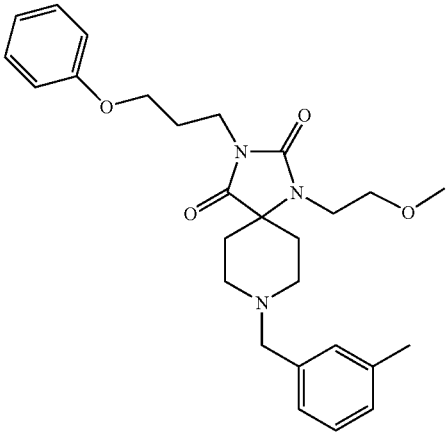 | ER-813515 | 0.317 |
| 209 | 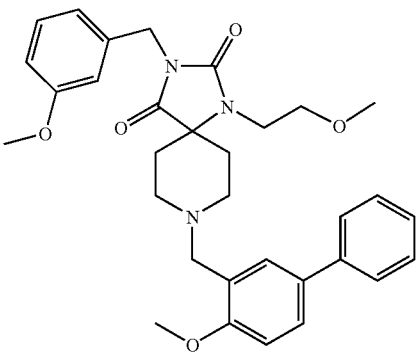 | ER-817209 | 0.325 |

TABLE 4-continued

IC$_{50}$ Data of Exemplary Compounds

| Example # | Structure | ER # | IC$_{50}$ (µM) |
|---|---|---|---|
| 210 | 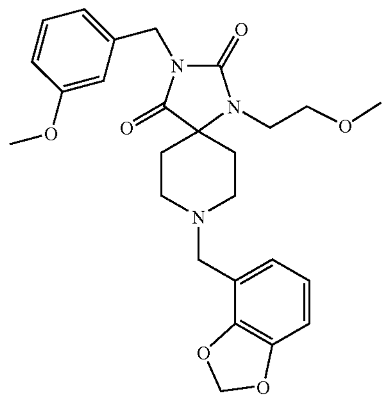 | ER-812324 | 0.333 |
| 211 | 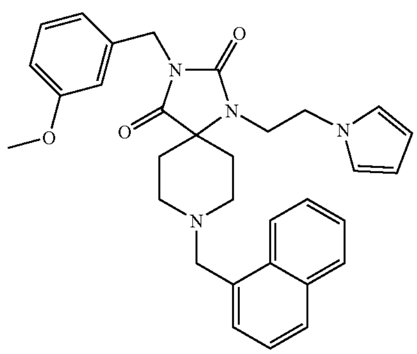 | ER-818533 | 0.334 |
| 212 | 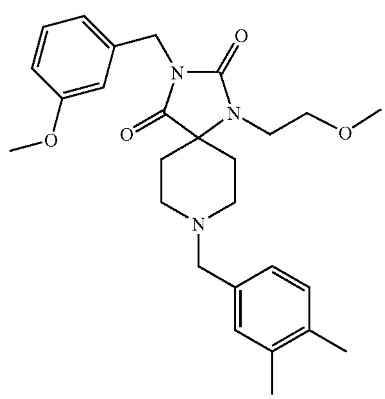 | ER-813212 | 0.336 |
| 213 | 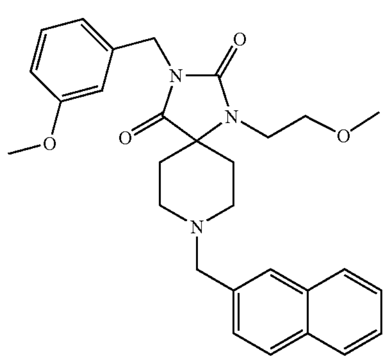 | ER-812280 | 0.337 |

TABLE 4-continued

IC$_{50}$ Data of Exemplary Compounds

| Example # | Structure | ER # | IC$_{50}$ (µM) |
|---|---|---|---|
| 214 | 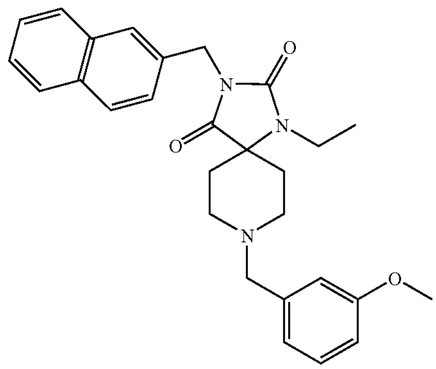 | ER-813537 | 0.344 |
| 215 | 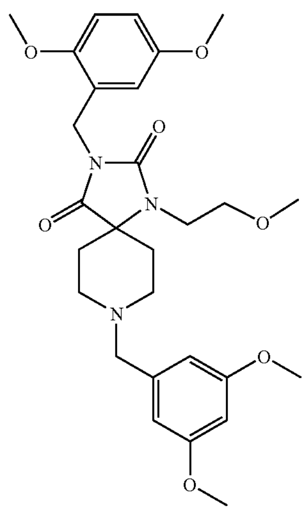 | ER-819696 | 0.348 |
| 216 | 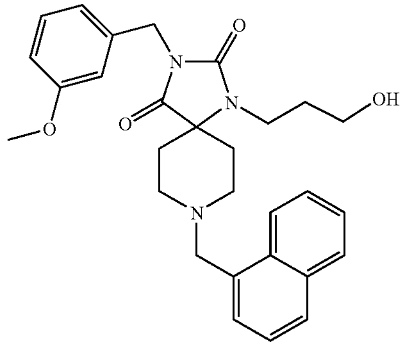 | ER-818539 | 0.349 |

TABLE 4-continued

IC$_{50}$ Data of Exemplary Compounds

| Example # | Structure | ER # | IC$_{50}$ (μM) |
|---|---|---|---|
| 217 | 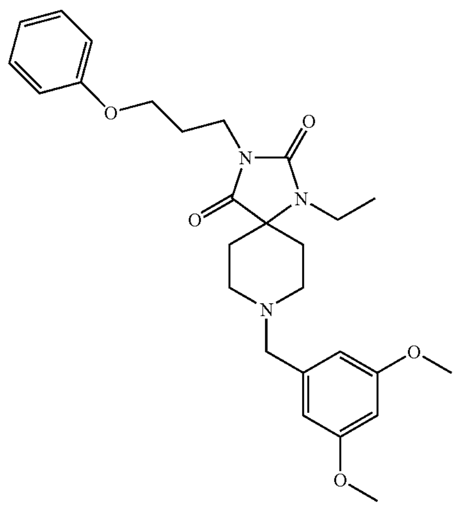 | ER-813533 | 0.350 |
| 218 | 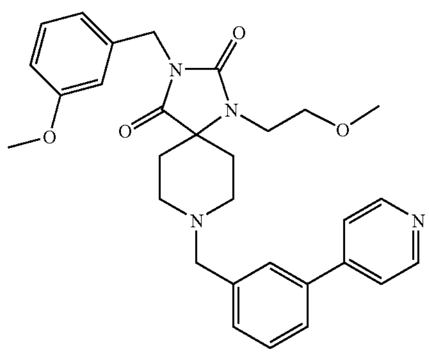 | ER-813128 | 0.351 |
| 219 | 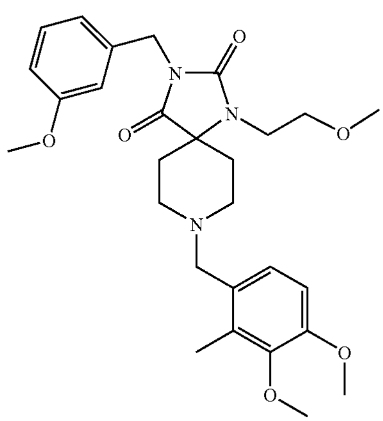 | ER-817207 | 0.362 |

TABLE 4-continued

IC₅₀ Data of Exemplary Compounds

| Example # | Structure | ER # | IC$_{50}$ (μM) |
|---|---|---|---|
| 220 | 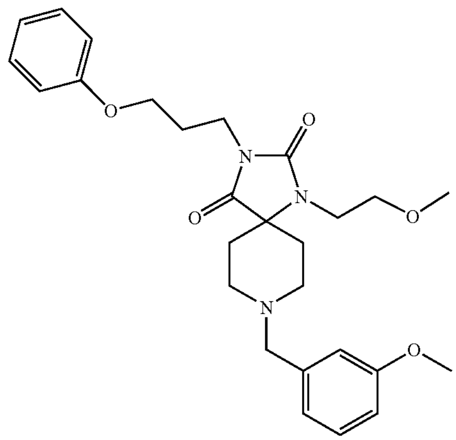 | ER-813513 | 0.362 |
| 221 | 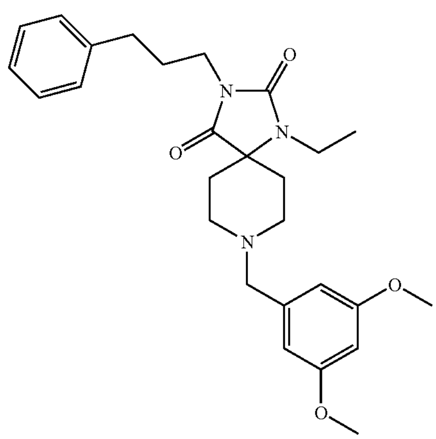 | ER-813524 | 0.365 |
| 222 | 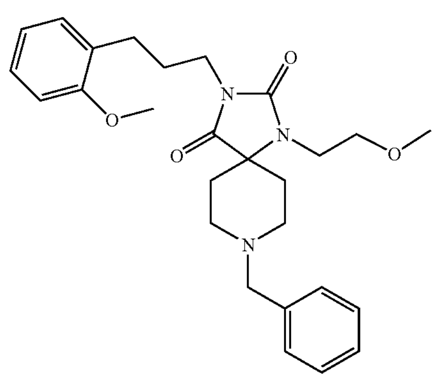 | ER-813420 | 0.366 |

TABLE 4-continued
IC$_{50}$ Data of Exemplary Compounds
| Example # | Structure | ER # | IC$_{50}$ (μM) |
|---|---|---|---|
| 223 | 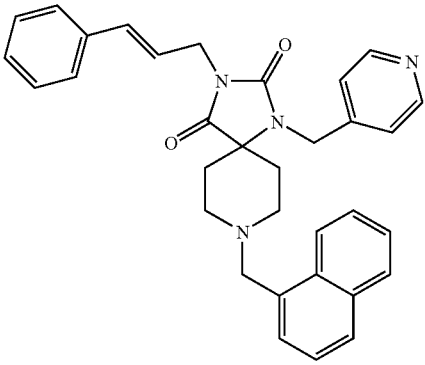 | ER-818515 | 0.371 |
| 224 | 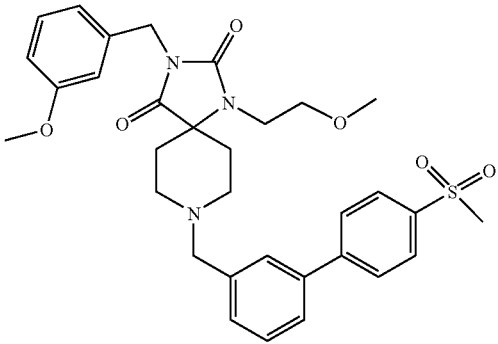 | ER-813123 | 0.371 |
| 225 | 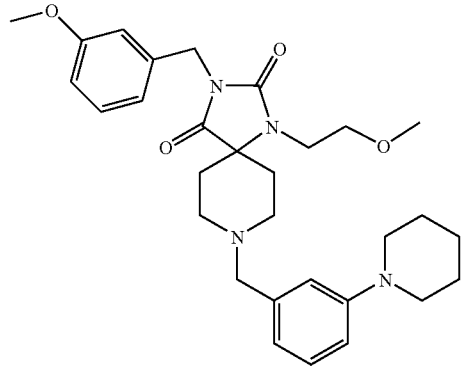 | ER-817053 | 0.373 |
| 226 | 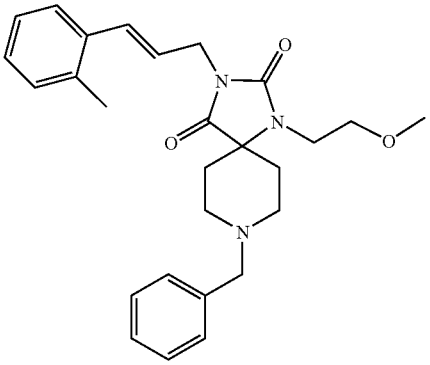 | ER-813405 | 0.373 |

TABLE 4-continued

IC$_{50}$ Data of Exemplary Compounds

| Example # | Structure | ER # | IC$_{50}$ (μM) |
|---|---|---|---|
| 227 | 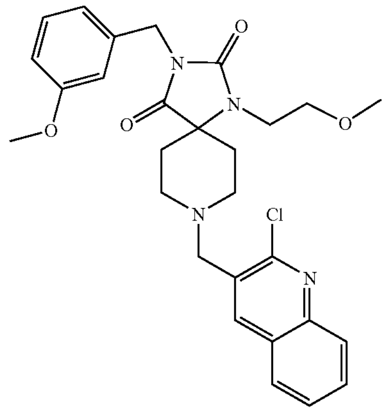 | ER-813102 | 0.373 |
| 228 | 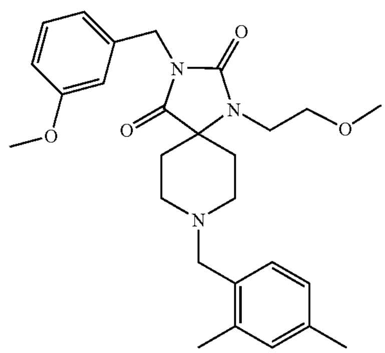 | ER-813088 | 0.374 |
| 229 | 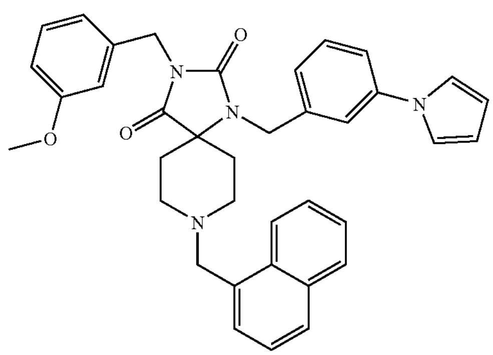 | ER-818565 | 0.377 |
| 230 | 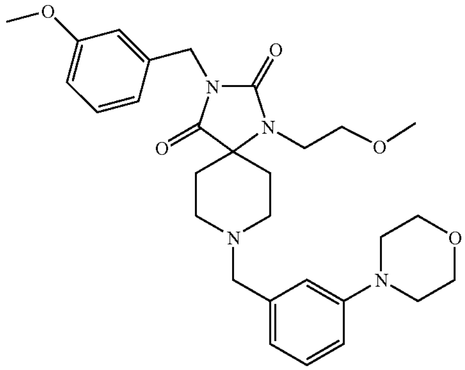 | ER-817054 | 0.379 |

TABLE 4-continued
IC₅₀ Data of Exemplary Compounds
| Example # | Structure | ER # | IC₅₀ (μM) |
|---|---|---|---|
| 231 | 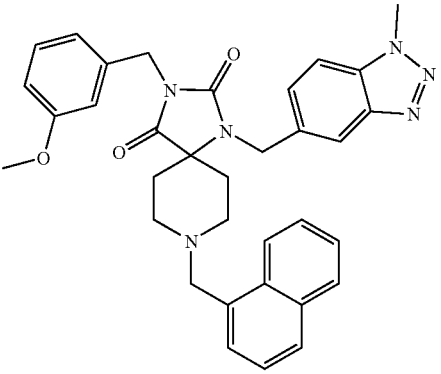 | ER-818566 | 0.385 |
| 232 | 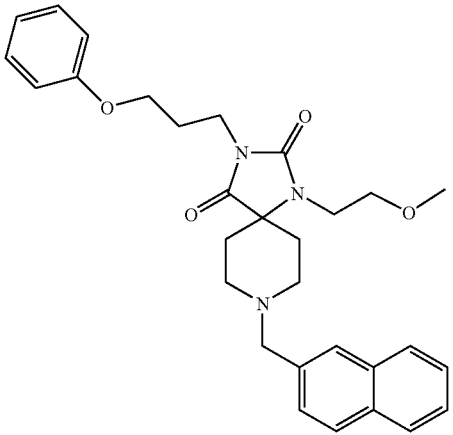 | ER-813517 | 0.385 |
| 233 | 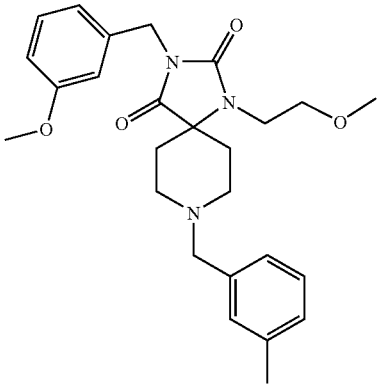 | ER-812310 | 0.386 |

TABLE 4-continued

IC$_{50}$ Data of Exemplary Compounds

| Example # | Structure | ER # | IC$_{50}$ (μM) |
|---|---|---|---|
| 234 | 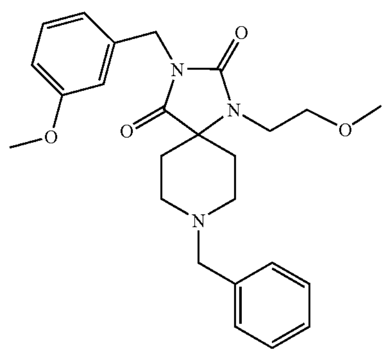 | ER-812630 | 0.387 |
| 235 | 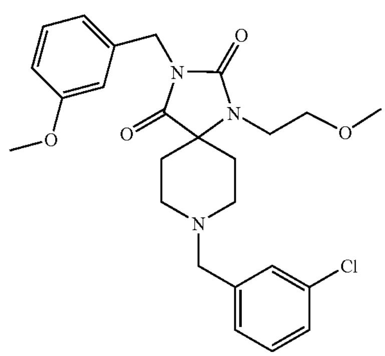 | ER-812599 | 0.390 |
| 236 | 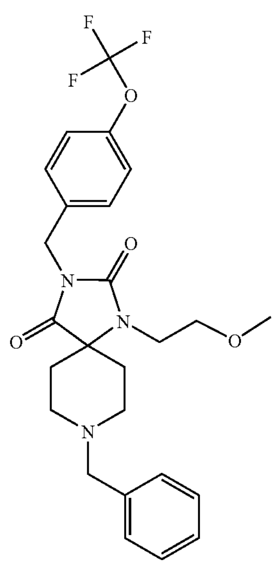 | ER-813277 | 0.395 |

TABLE 4-continued

IC$_{50}$ Data of Exemplary Compounds

| Example # | Structure | ER # | IC$_{50}$ (μM) |
|---|---|---|---|
| 237 | 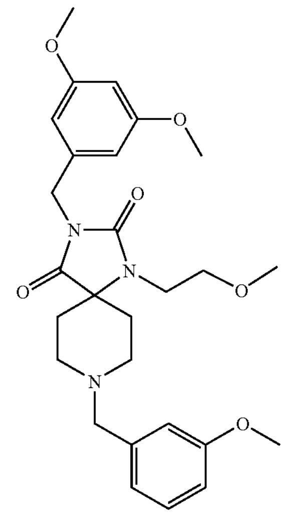 | ER-817127 | 0.414 |
| 238 | 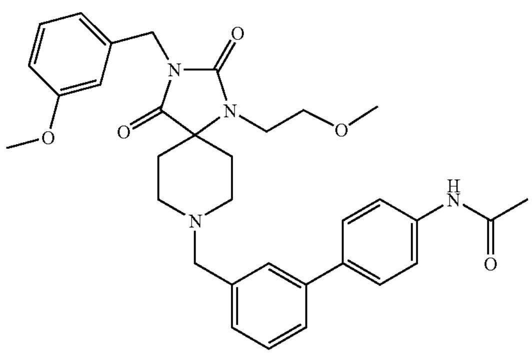 | ER-813129 | 0.414 |
| 239 | 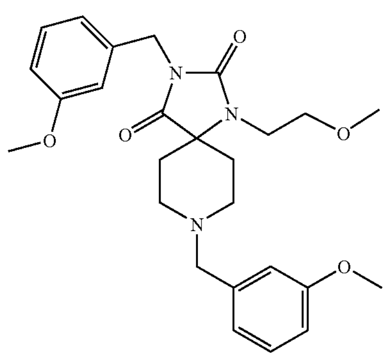 | ER-812598 | 0.417 |

TABLE 4-continued

IC$_{50}$ Data of Exemplary Compounds

| Example # | Structure | ER # | IC$_{50}$ (μM) |
|---|---|---|---|
| 240 | 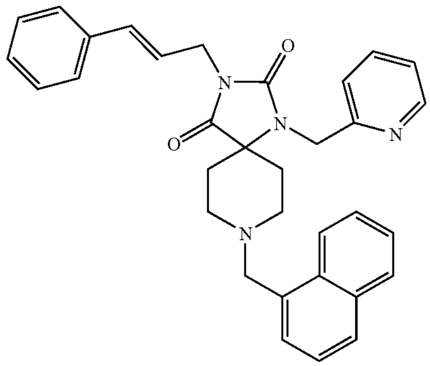 | ER-818514 | 0.420 |
| 241 | 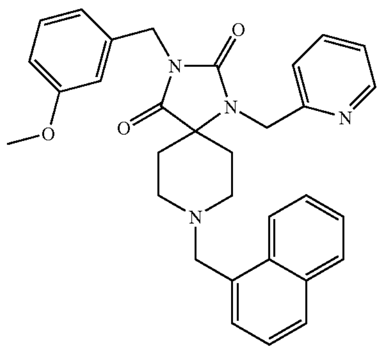 | ER-818534 | 0.424 |
| 242 | 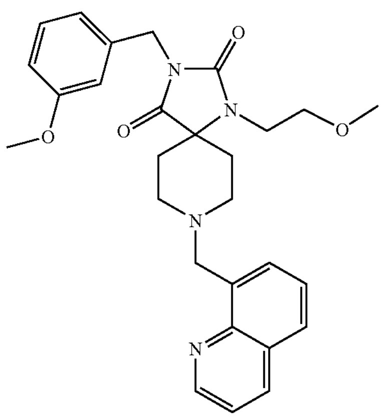 | ER-812427 | 0.424 |
| 243 | 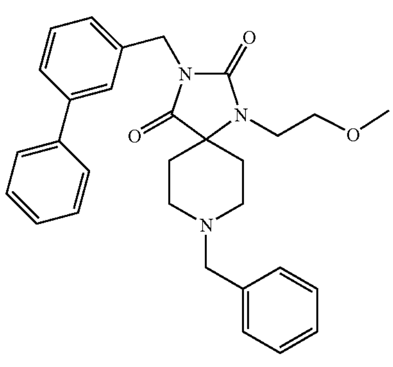 | ER-817035 | 0.431 |

TABLE 4-continued

IC$_{50}$ Data of Exemplary Compounds

| Example # | Structure | ER # | IC$_{50}$ (μM) |
|---|---|---|---|
| 244 | 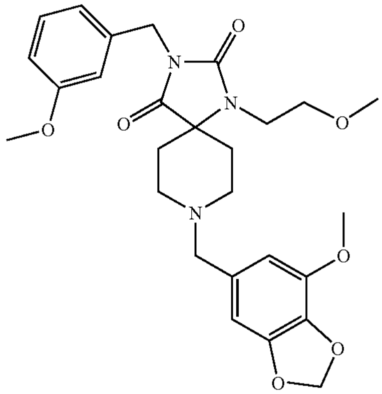 | ER-817186 | 0.432 |
| 245 | 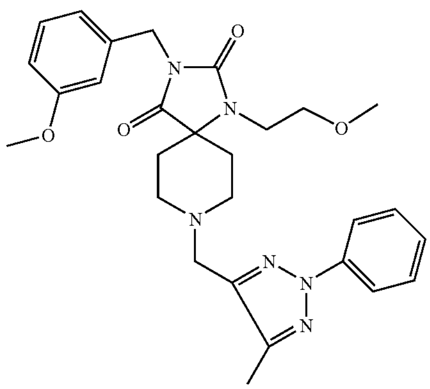 | ER-812436 | 0.432 |
| 246 | 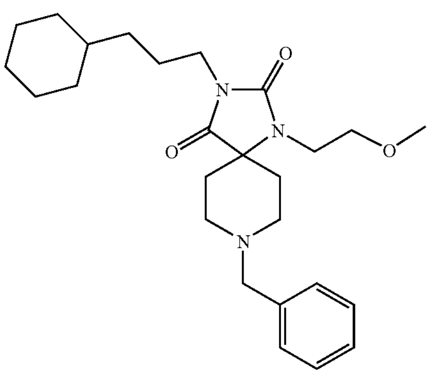 | ER-813426 | 0.435 |
| 247 | 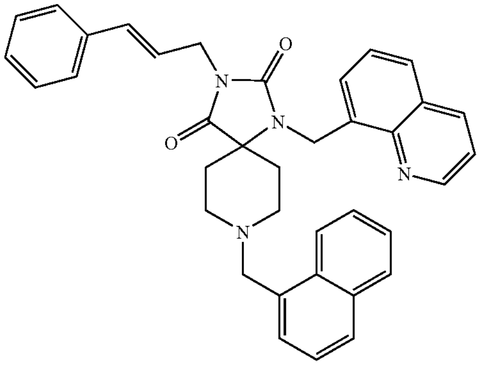 | ER-818551 | 0.436 |

TABLE 4-continued

IC$_{50}$ Data of Exemplary Compounds

| Example # | Structure | ER # | IC$_{50}$ (µM) |
|---|---|---|---|
| 248 | 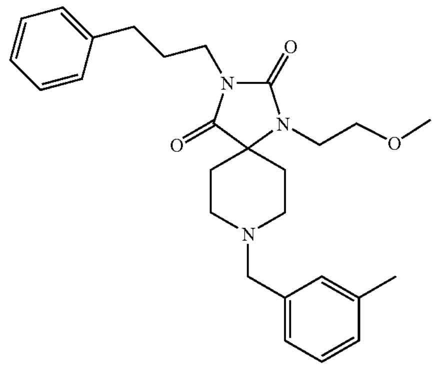 | ER-813488 | 0.438 |
| 249 | 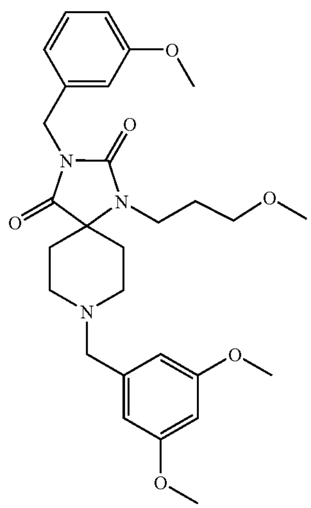 | ER-817136 | 0.441 |
| 250 | 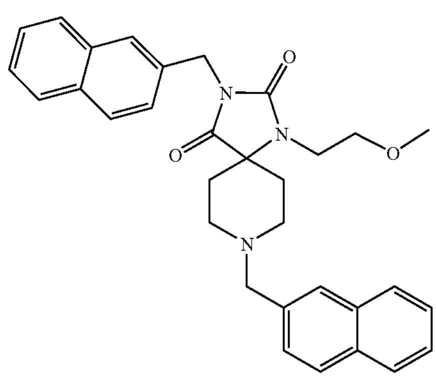 | ER-813532 | 0.442 |

TABLE 4-continued

IC$_{50}$ Data of Exemplary Compounds

| Example # | Structure | ER # | IC$_{50}$ (μM) |
|---|---|---|---|
| 251 | 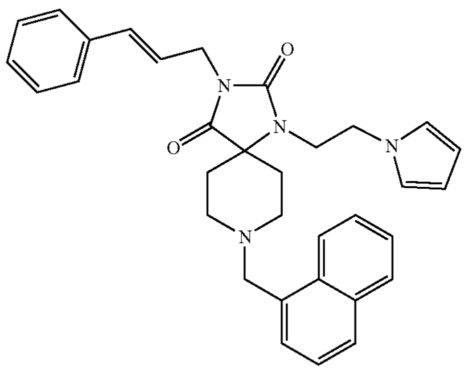 | ER-818513 | 0.447 |
| 252 | 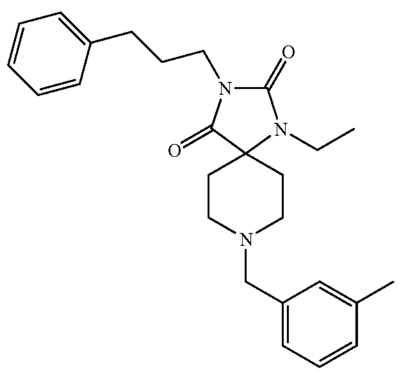 | ER-813525 | 0.448 |
| 253 | 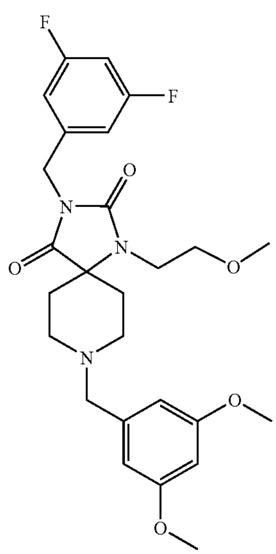 | ER-819694 | 0.450 |

TABLE 4-continued

IC₅₀ Data of Exemplary Compounds

| Example # | Structure | ER # | IC$_{50}$ (μM) |
|---|---|---|---|
| 254 | 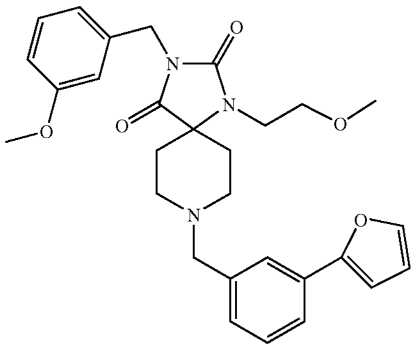 | ER-813134 | 0.451 |
| 255 | 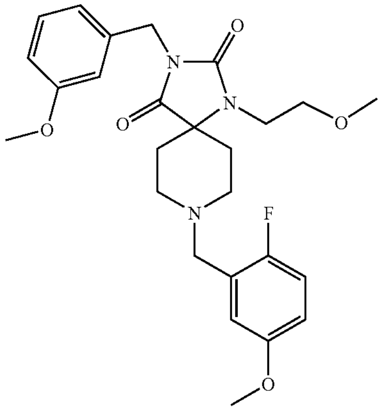 | ER-812332 | 0.452 |
| 256 | 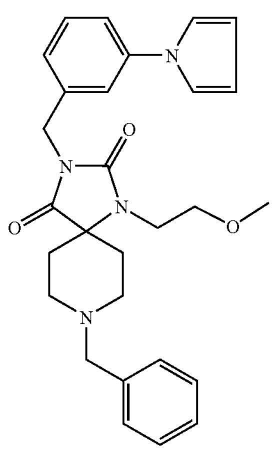 | ER-813068 | 0.469 |

TABLE 4-continued
IC$_{50}$ Data of Exemplary Compounds
| Example # | Structure | ER # | IC$_{50}$ (μM) |
|---|---|---|---|
| 257 | 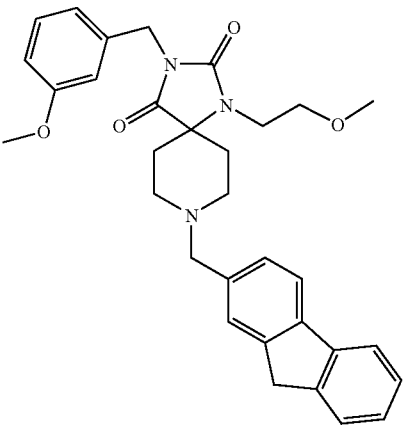 | ER-812286 | 0.479 |
| 258 | 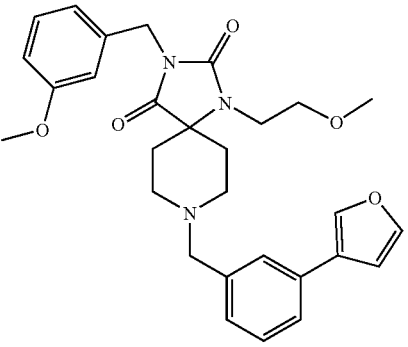 | ER-813135 | 0.481 |
| 259 | 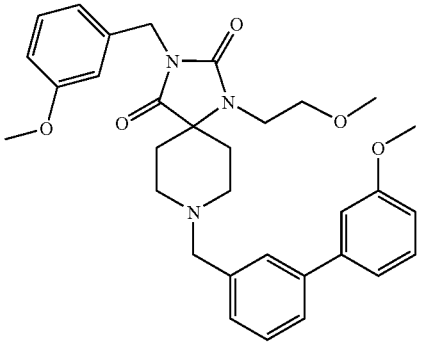 | ER-813118 | 0.484 |

TABLE 4-continued
IC$_{50}$ Data of Exemplary Compounds
| Example # | Structure | ER # | IC$_{50}$ (μM) |
|---|---|---|---|
| 260 | 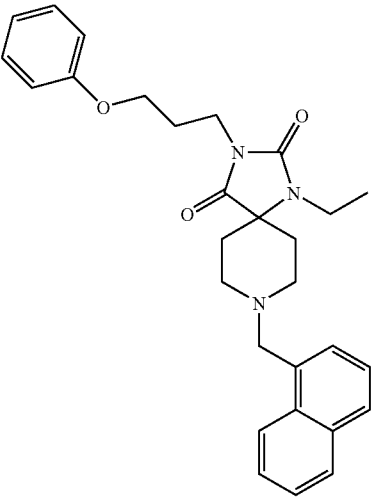 | ER-813535 | 0.486 |
| 261 | 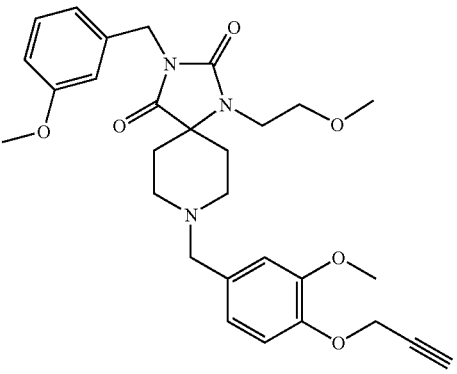 | ER-817208 | 0.490 |
| 262 | 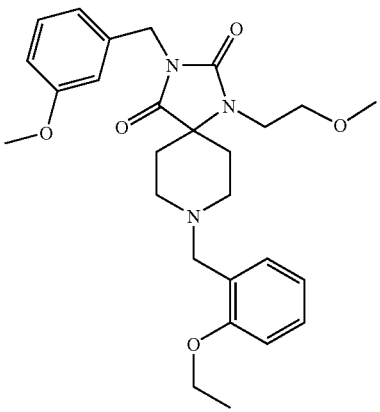 | ER-813085 | 0.495 |

TABLE 4-continued

IC$_{50}$ Data of Exemplary Compounds

| Example # | Structure | ER # | IC$_{50}$ (µM) |
|---|---|---|---|
| 263 | 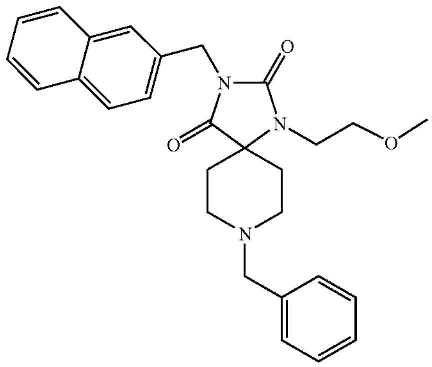 | ER-812628 | 0.498 |
| 264 | 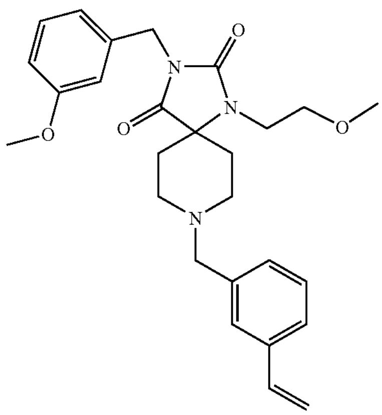 | ER-813110 | 0.500 |
| 265 | 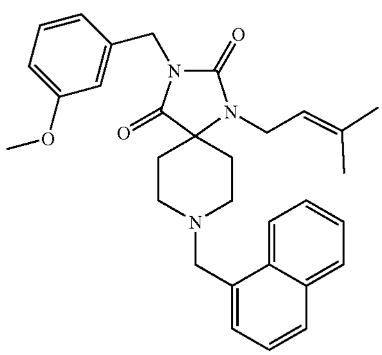 | ER-818540 | 0.501 |
| 266 | 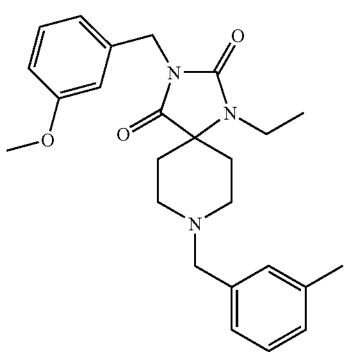 | ER-813544 | 0.510 |

TABLE 4-continued

IC$_{50}$ Data of Exemplary Compounds

| Example # | Structure | ER # | IC$_{50}$ (µM) |
|---|---|---|---|
| 267 | 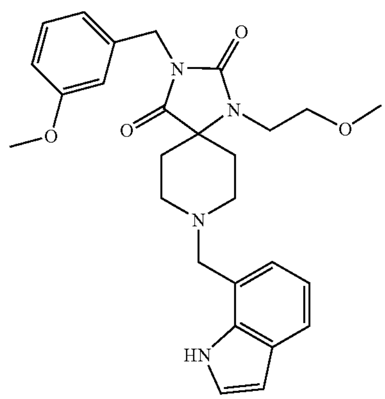 | ER-812265 | 0.510 |
| 268 | 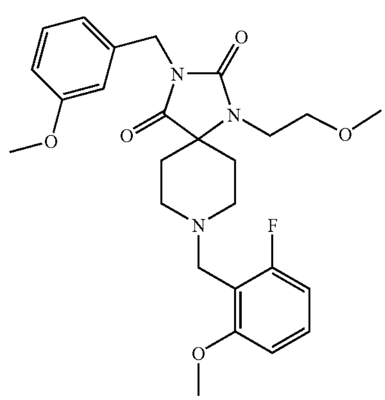 | ER-817194 | 0.511 |
| 269 | 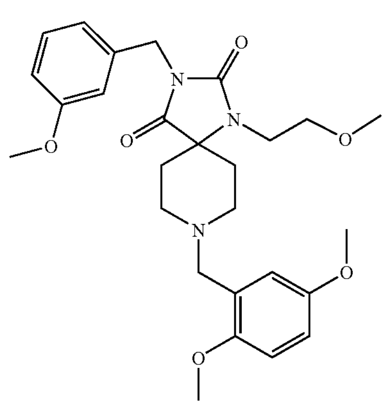 | ER-812320 | 0.513 |

TABLE 4-continued
IC$_{50}$ Data of Exemplary Compounds
| Example # | Structure | ER # | IC$_{50}$ (μM) |
|---|---|---|---|
| 270 | 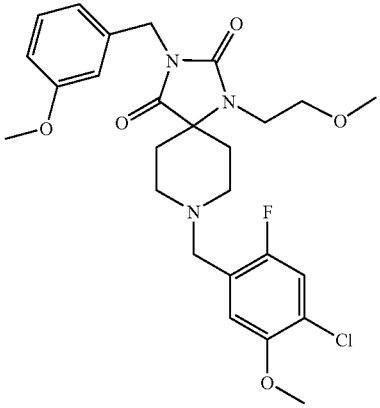 | ER-818591 | 0.518 |
| 271 | 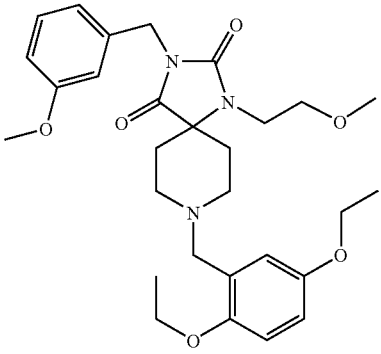 | ER-813100 | 0.522 |
| 272 | 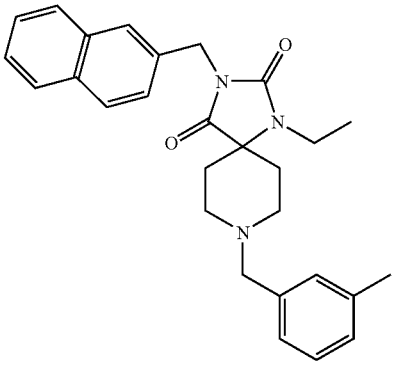 | ER-813539 | 0.525 |
| 273 | 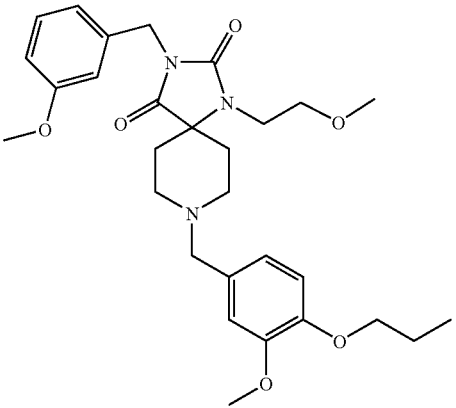 | ER-818592 | 0.528 |

TABLE 4-continued

IC$_{50}$ Data of Exemplary Compounds

| Example # | Structure | ER # | IC$_{50}$ (μM) |
|---|---|---|---|
| 274 | 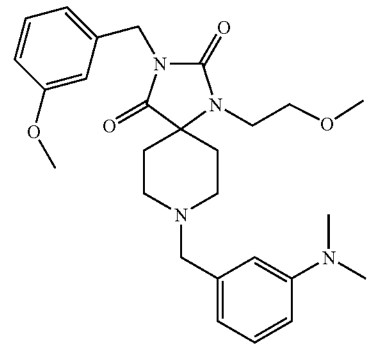 | ER-813141 | 0.528 |
| 275 | 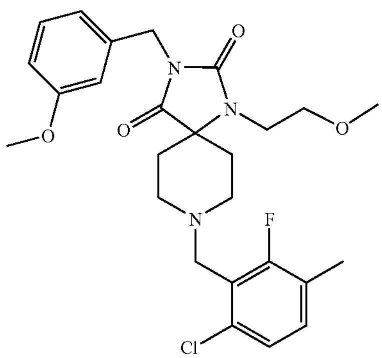 | ER-812378 | 0.532 |
| 276 | 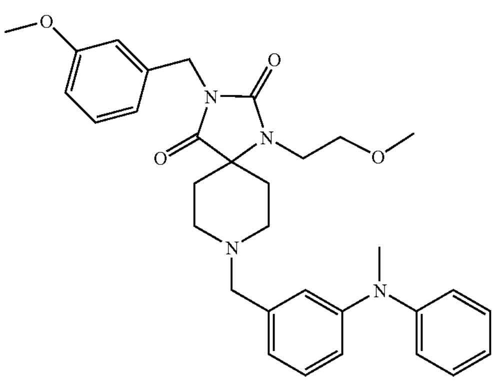 | ER-817055 | 0.538 |
| 277 | 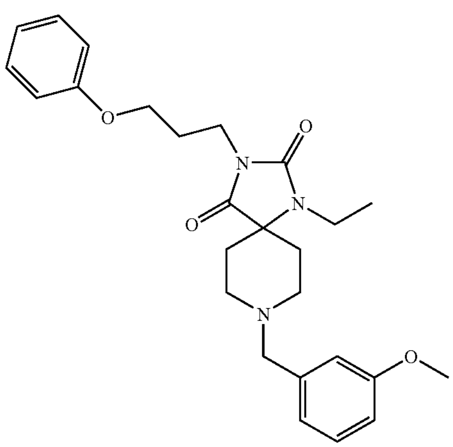 | ER-813520 | 0.540 |

TABLE 4-continued
IC$_{50}$ Data of Exemplary Compounds
| Example # | Structure | ER # | IC$_{50}$ (μM) |
|---|---|---|---|
| 278 | 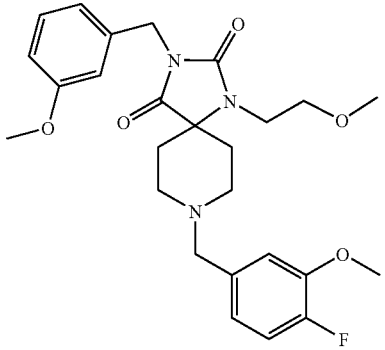 | ER-812333 | 0.542 |
| 279 | 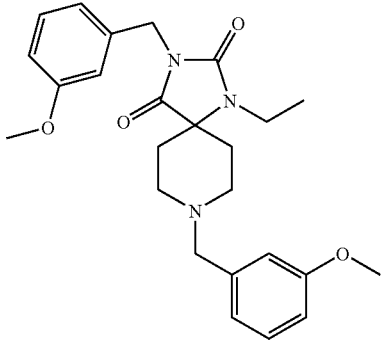 | ER-813542 | 0.546 |
| 280 | 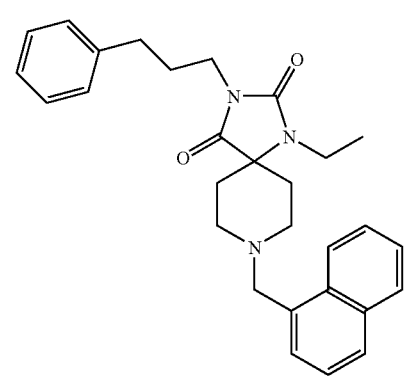 | ER-813526 | 0.546 |

TABLE 4-continued
IC$_{50}$ Data of Exemplary Compounds
| Example # | Structure | ER # | IC$_{50}$ (µM) |
|---|---|---|---|
| 281 | 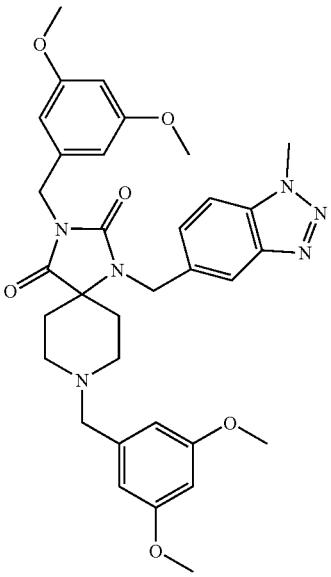 | ER-817122 | 0.548 |
| 282 | 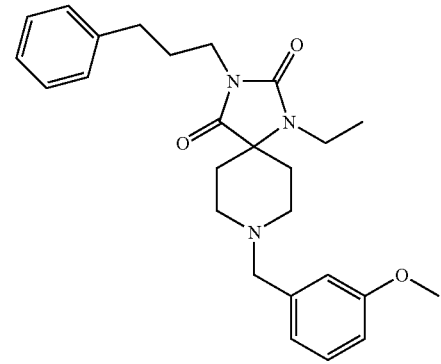 | ER-813523 | 0.549 |
| 283 | 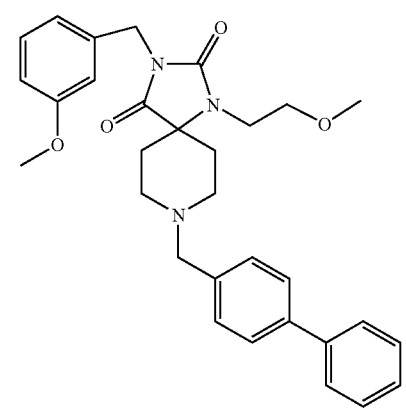 | ER-812590 | 0.550 |

TABLE 4-continued
IC$_{50}$ Data of Exemplary Compounds
| Example # | Structure | ER # | IC$_{50}$ (μM) |
|---|---|---|---|
| 284 | 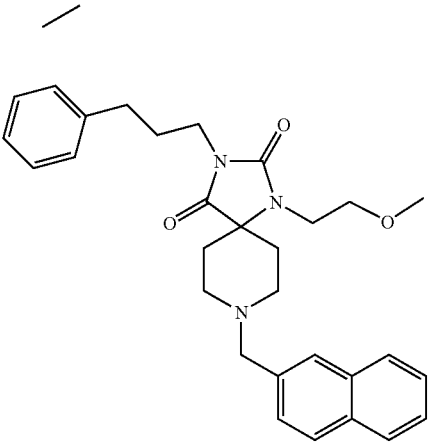 | ER-813490 | 0.551 |
| 285 | 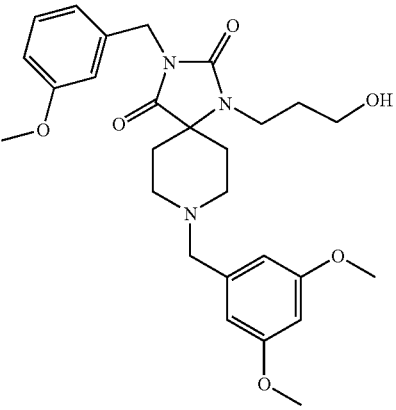 | ER-818549 | 0.553 |
| 286 | 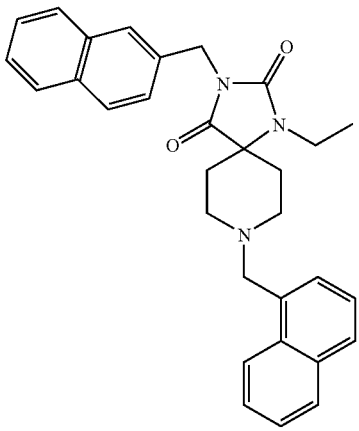 | ER-813540 | 0.560 |

TABLE 4-continued

IC$_{50}$ Data of Exemplary Compounds

| Example # | Structure | ER # | IC$_{50}$ (μM) |
|---|---|---|---|
| 287 | 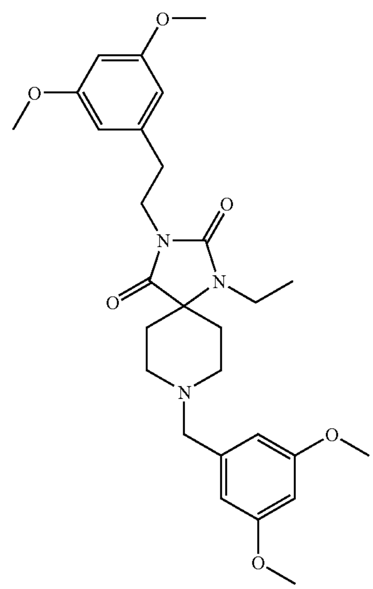 | ER-819683 | 0.561 |
| 288 | 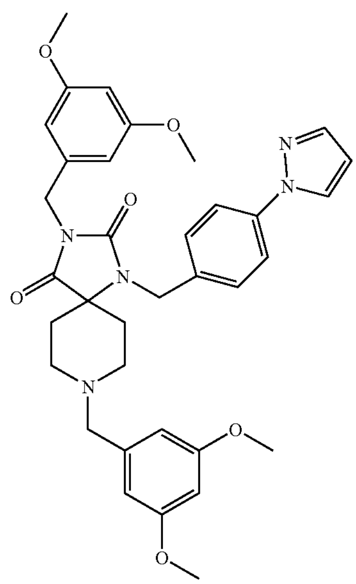 | ER-817123 | 0.567 |
| 289 | 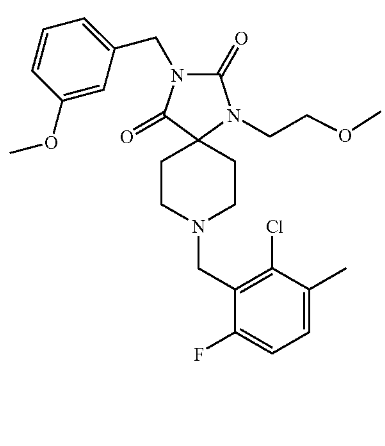 | ER-812373 | 0.567 |

TABLE 4-continued
IC$_{50}$ Data of Exemplary Compounds
| Example # | Structure | ER # | IC$_{50}$ (µM) |
|---|---|---|---|
| 290 | 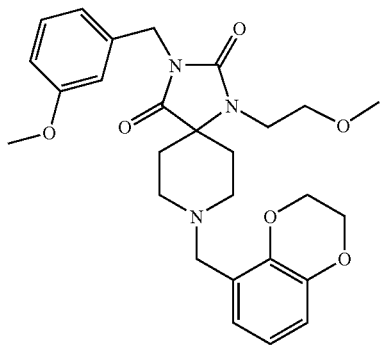 | ER-818585 | 0.568 |
| 291 | 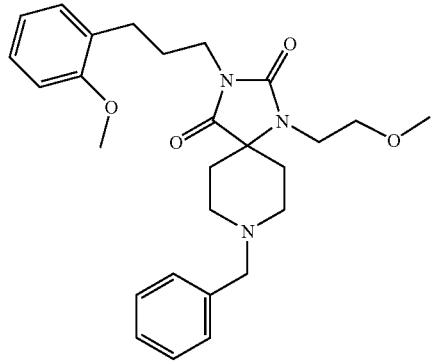 | ER-813368 | 0.572 |
| 292 | 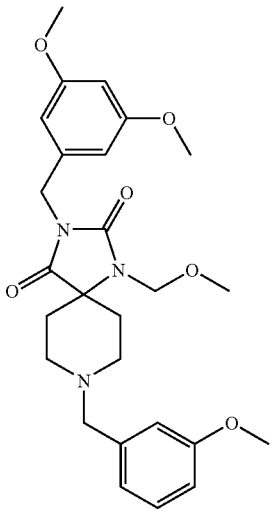 | ER-817125 | 0.576 |

TABLE 4-continued
IC₅₀ Data of Exemplary Compounds
| Example # | Structure | ER # | IC₅₀ (μM) |
|---|---|---|---|
| 293 | 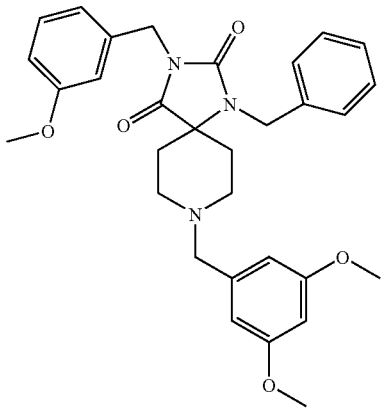 | ER-818541 | 0.579 |
| 294 | 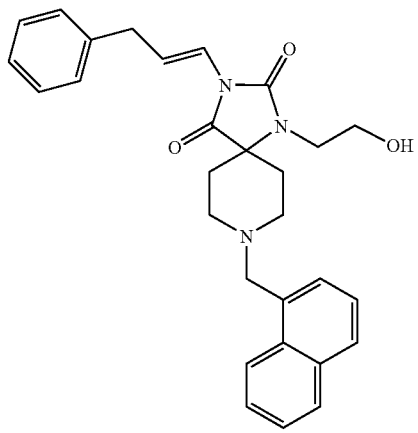 | ER-817196 | 0.579 |
| 295 | 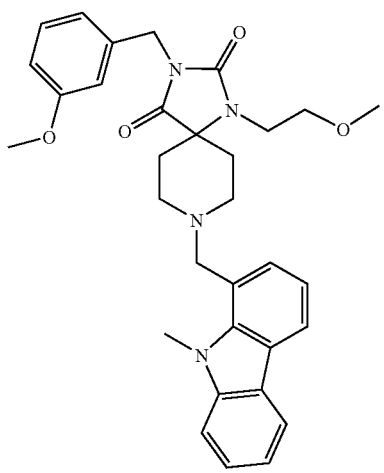 | ER-817175 | 0.580 |

TABLE 4-continued

IC$_{50}$ Data of Exemplary Compounds

| Example # | Structure | ER # | IC$_{50}$ (μM) |
|---|---|---|---|
| 296 | 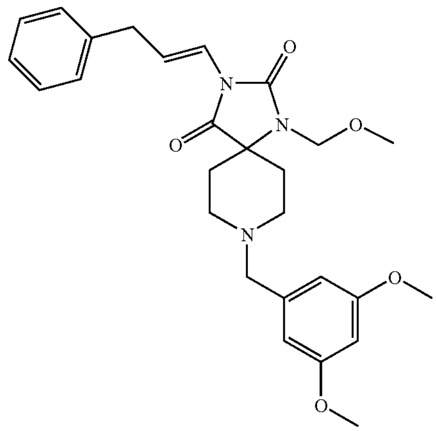 | ER-817200 | 0.586 |
| 297 | 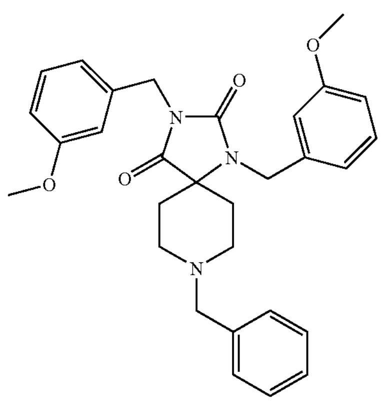 | ER-813165 | 0.586 |
| 298 | 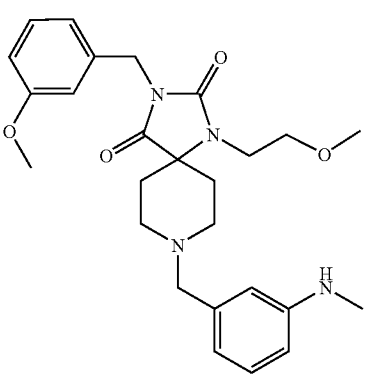 | ER-813143 | 0.589 |

TABLE 4-continued

IC$_{50}$ Data of Exemplary Compounds

| Example # | Structure | ER # | IC$_{50}$ (μM) |
|---|---|---|---|
| 299 | 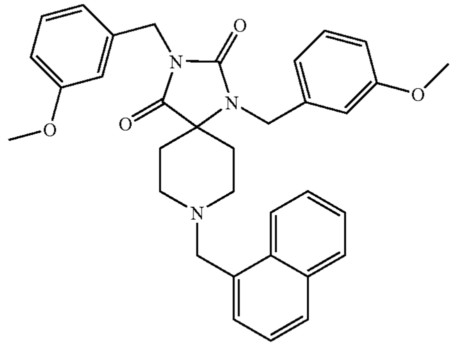 | ER-818532 | 0.596 |
| 300 | 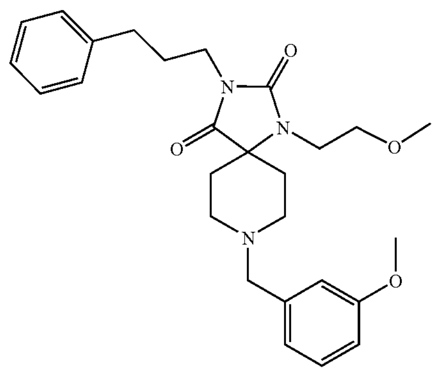 | ER-813487 | 0.598 |
| 301 | 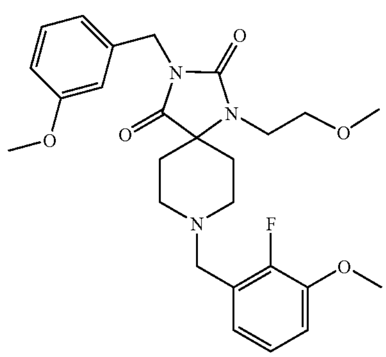 | ER-817189 | 0.599 |

In vivo Assay Compounds of the present invention are assayed in vivo using methods known to one of ordinary skill in the art. In particular, the present compounds are assayed using the collagen induced arthritis ("CIA") model using methods well established in the art. In addition, the present compounds are assayed using the experimental autoimmune encephalomyelitis ("EAE") assay which is an established model regarding multiple sclerosis. This assay may be performed in a manner substantially similar to that described by Hart, et al, "Modelling of multiple sclerosis: lessons learned in a non-human primate." *Lancet. Neurology* Vol. 3, issue 10 (2004) pp 588-597.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than limited by the specific embodiment that have been represented by way of example.

We claim:
1. A compound of formula I:

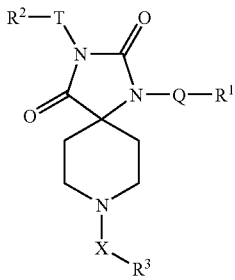

wherein:
Q is methylene or ethylene;
R¹ is C$_{1-6}$ alkoxy, C$_{1-8}$ hydroxyalkyl, (C$_{1-3}$ alkoxy)C$_{1-3}$ alkyl, C$_{1-3}$ alkylthio, C$_{2-5}$ alkenyl, phenyl, indolyl, quinolyl, pyrazolyl, pyrrolyl, pyridinyl, furyl, N-methylbenzotriazolyl, hydroxyethyl, propenyl, (ethoxycarbonyl)propyl, or tetrahydropyranyloxybutyl,
  wherein R¹ has
    (a) 0-3 substituents independently selected from cyano, methyl, methoxy, pyrazolyl, furyl, hydroxyethyl, acetamido, pyrrolyl, and propenyl, and
    (b) 0-1 substituents selected from benzotriazolyl, N-methyl-benzotriazolyl, and benzo[d][1,3]dioxolyl,
T is C═O, —CH$_2$—, —CH$_2$—CH$_2$—, —CH═CH— (cis or trans), propenylene, —CH═CH—CH$_2$— (cis or trans), —CH$_2$—CH═CH— (cis or trans), ethynylene, or vinylene;
R² is selected from phenyl, phenoxy, benzyloxy, naphthyl, furyl, isoquinolinyl, quinolyl, indolyl, pyrazolyl, thiazolyl, anthryl, and benzothienyl,
  wherein R² is substituted with 0 to 2 substituents,
    (a) wherein between 0 and 2 substituents are independently selected from methyl, methoxy, trifluoromethoxy, hydroxyl, hydroxymethyl, fluoro, chloro, bromo, dimethylamino, t-butyl, and isobutoxy; and
    (b) between 0 and 1 substituents are selected from phenyl, pyridyl, pyrazolyl, furyl, benzoyl, pyrrolyl, pyridinyl, naphthyl, phenoxy, benzo[d][1,3]dioxolyl, cyclohexyl, cyclopentyl, cyclobutyl, and cyclopropyl;
X is methylene, ethylene, or propenylene; and
R³ is selected from phenyl, biphenylyl, thiophenyl, bithiophenylyl, diphenylmethanyl, triazolyl, thienyl, benzofuryl, phenanthryl, anthryl, fluorenyl, acenaphthyl, pyrenyl, indanyl, adamantyl, carbazolyl, N-methylcarbazolyl, indolyl, pyrrolidinyl, quinolyl, pyrrolyl, naphthyl, methylnaphthyl, methoxynaphthyl, dimethylthienyl, benzothiadiazolyl, benzimidazolyl, benzothienyl, benzodioxanyl, benzodioxepinyl, benzodioxocinyl, and benzo[d][1,3]dioxolyl,
  wherein R³ is substituted with 0 to 4 substituents independently selected from methyl, trifluoromethyl, methoxy, trifluoromethoxy, chloro, fluoro, bromo, ethenyl, ethoxy, ethyl, isopropyl, t-butyl, propyloxy, amino, dimethylamino, methylamino, allyloxy, (methyl)(phenyl) amino, methanesulfonyl, t-butoxycarbonylmethylamino, t-butoxycarbonyl, boronic acid moiety, and methylcarbonylamin;
and wherein either R¹ is C$_{1-6}$ alkoxy or X is propenylene;
or a pharmaceutically acceptable salt thereof.

2. The compound of claim 1, wherein R¹ is hydroxymethyl, methoxy, methoxymethyl, methylthio, phenyl, indolyl, pyrazolyl, pyrrolyl, pyridinyl, furyl, N-methylbenzotriazolyl, or hydroxyethyl; and wherein R¹ has 0 to 2 substituents.

3. The compound of claim 1, wherein R² is selected from phenyl, naphthyl, furyl, isoquinolinyl, quinolyl, indolyl, pyrazolyl, thiazolyl, and benzothienyl, wherein R² is substituted with 0 to 2 groups, wherein between 0 and 2 substituents are independently selected from methyl, methoxy, trifluoromethoxy, hydroxyl, fluoro, and hydroxymethyl.

4. The compound of claim 1, wherein X is methylene.

5. The compound of claim 1, wherein T is —CH$_2$—, —CH═CH— (cis or trans), —CH═CH—CH$_2$— (cis or trans), —CH$_2$—CH═CH— (cis or trans), ethynylene, or vinylene.

6. The compound of claim 4, wherein T is methylene, —CH═CH—CH$_2$-(trans), or —CH$_2$—CH═CH— (trans).

7. The compound of claim 1, wherein Q is methylene.

8. The compound of claim 1, wherein Q is ethylene.

9. The compound of claim 1, wherein:
R³ is selected from the group consisting of phenyl, biphenylyl, thiophenyl, bithiophenylyl, triazolyl, thienyl, benzofuryl, phenanthryl, indolyl, pyrrolidinyl, quinolyl, pyrrolyl, naphthyl, methylnaphthyl, methoxynaphthyl, dimethylthienyl, benzothiadiazolyl, benzimidazolyl, benzothiophenyl, benzodioxanyl, benzodioxepinyl, benzodioxocinyl, and benzo[d][1,3]dioxolyl;
wherein R$_3$ is substituted with between 0 and 3 substituents independently selected from methyl, trifluoromethyl, methoxy, trifluoromethoxy, chloro, fluoro, bromo, ethenyl, ethoxy, ethyl, isopropyl, t-butyl, propyloxy, amino, dimethylamino, methylamino, allyloxy, (methyl)(phenyl)amino, methanesulfonyl, t-butoxycarbonylmethylamino, t-butoxycarbonyl, boronic acid moiety, and methylcarbonylamino.

10. The compound of claim 7, wherein R³ is phenyl, naphthyl, anthryl, biphenylyl, fluorenyl, or acenapthyl with between 0 and 3 substituents independently selected from fluoro, bromo methyl, methoxy, and hydroxymethyl.

11. The compound of claim 1, wherein R¹ is methoxymethyl or hydroxymethyl.

12. The compound of claim 1, wherein R¹ is C$_{1-4}$ hydroxyalkyl, (C$_{1-3}$ alkoxy)C$_{1-3}$ alkyl, C$_{1-3}$ alkylthio, C$_{2-5}$ alkenyl, hydroxyethyl, propenyl, or (ethoxycarbonyl)propyl; wherein R¹ has 0-3 substituents independently selected from cyano, methyl, methoxy, hydroxyethyl, acetamido, and propenyl.

13. The compound of claim 1, wherein R² is a phenyl group with between 0 and 3 substituents independently selected from methoxy, trifluoromethoxy, fluoro, and methyl.

14. The compound of claim 1, wherein:
R¹ is hydroxymethyl, methoxy, methoxymethyl, methylthio, phenyl, pyrazolyl, pyrrolyl, pyridinyl, furyl, or N-methylbenzotriazolyl; or R¹ is phenyl independently substituted with methyl, methoxy, pyrazolyl, furyl, benzotriazolyl, N-methyl-benzotriazolyl, or pyrrolyl;
T is —CH$_2$—, —CH$_2$—CH$_2$—, —CH═CH—CH$_2$— (trans), ethynylene, or allyl;
R² is selected from phenyl, naphthyl, furyl, quinolyl, indolyl, pyrazolyl, thiazolyl, and benzothienyl, wherein R² is substituted with 0-2 groups, wherein between 0 and 2 substituents are independently selected from methyl, methoxy, trifluoromethoxy, hydroxyl, and hydroxymethyl; and R[3] is selected from phenyl, naphthyl, thienyl, benzofuryl, indolyl, isoquinolinyl, quinolyl, pyridinyl, pyrrolyl, benzothiadiazolyl, and benzimidazolyl, wherein R[3] is substituted with between 0 and 2 substituents-independently selected from methyl, trifluoromethyl, methoxy, trifluoromethoxy, chloro, fluoro, bromo, ethenyl, ethoxy, ethyl, dimethylamino, and methylamino.

15. The compound of claim 1, wherein:

R[1] is hydroxymethyl, methoxy, methoxymethyl, methylthio, phenyl, pyrazolyl, pyrrolyl, pyridinyl, furyl, C$_{1-8}$ hydroxyalkyl, or N-methylbenzotriazolyl;

or R[1] is substituted with 0 to I substituents selected from methyl, methoxy, pyrazolyl, furyl, pyridinyl, benzotriazolyl, N-methyl-benzotriazolyl, and pyrrolyl;

T is —CH$_2$—, —CH$_2$—CH$_2$—, —CH═CH—CH$_2$— (trans), ethynylene, or allyl;

R[2] is selected from phenyl, naphthyl, furyl, quinolyl, indolyl, pyrazolyl, benzo[d][1,3]dioxolyl, thiazolyl, and benzothienyl, wherein R[7] is substituted with 0-3 groups, wherein between 0 and 3 substituents are independently selected from methyl, methoxy, trifluoromethoxy, hydroxyl, and hydroxymethyl;

X is methylene;

R[3] is selected from phenyl, naphthyl, thienyl, benzofuryl, indolyl, pyrrolidinyl, isoquinolyl, quinolyl, pyrrolyl, benzothiadiazolyl, benzimidazolyl, and benzothiophenyl;

wherein R[7] is substituted with between 0 and 2 substituents independently selected from methyl, trifluoromethyl, methoxy, trifluoromethoxy, chloro, fluoro, bromo, ethenyl, ethoxy, ethyl, dimethylamino, and methylamino.

16. A compound selected from the group consisting of:

| ER # | Structure |
|---|---|
| ER 818561 | 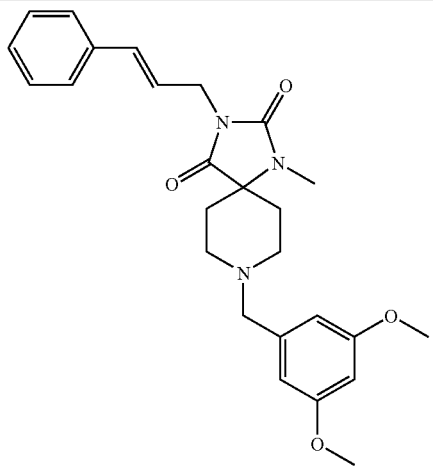 |
| ER 817135 | 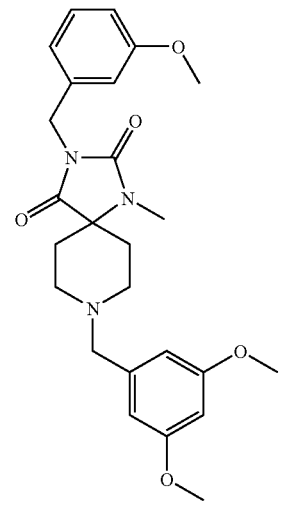 |
| ER 813508 | 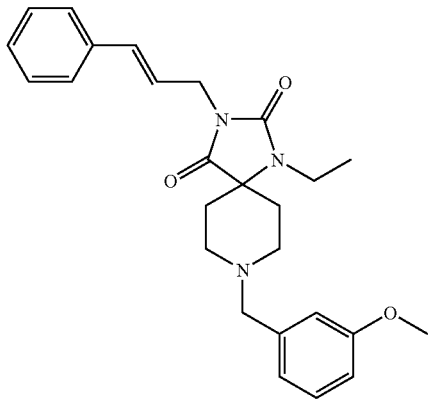 |
| ER 813509 | 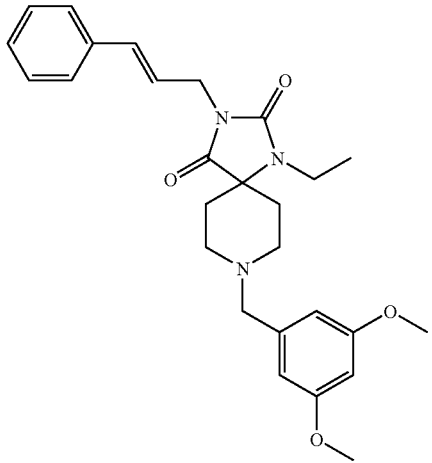 |

-continued
| ER # | Structure |
|---|---|
| ER 813493 | 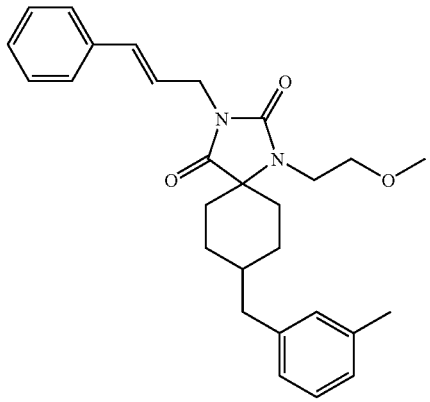 |
| ER 813510 | 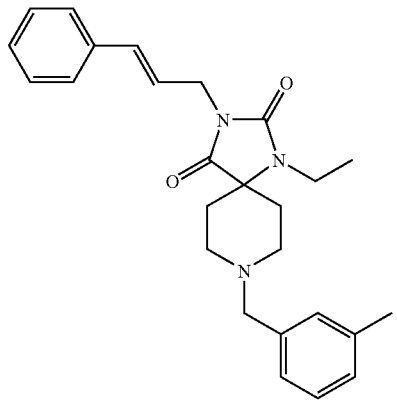 |
| ER 813511 | 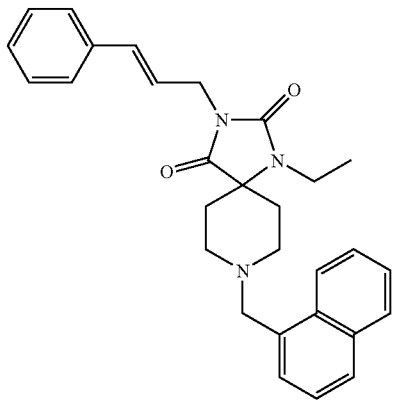 |
-continued
| ER # | Structure |
|---|---|
| ER 817118 | 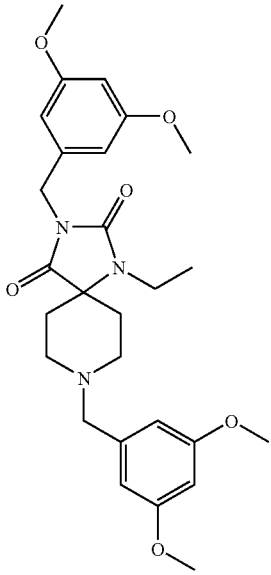 |
| ER 817137 | 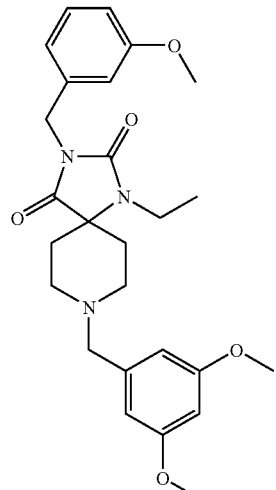 |
| ER 817119 | 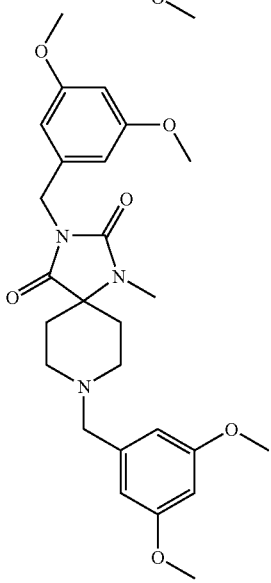 |

-continued
| ER # | Structure |
|---|---|
| ER 818573 | 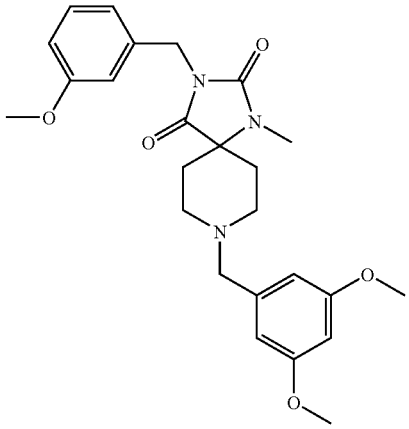 |
| ER 818567 | 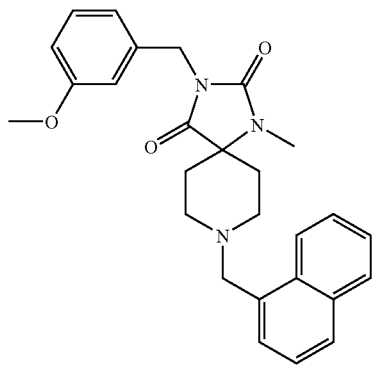 |
| ER 818550 | 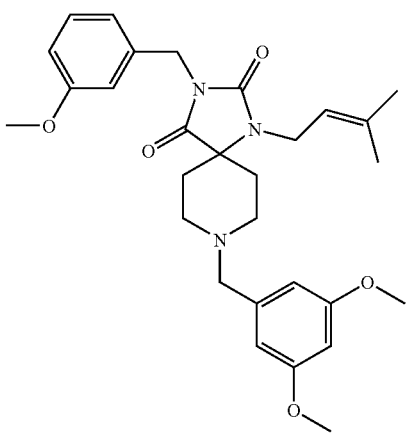 |
-continued
| ER # | Structure |
|---|---|
| ER 813512 | 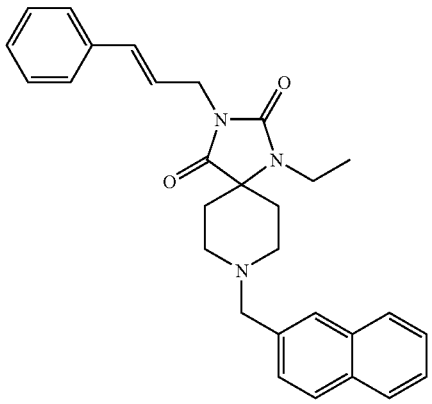 |
and pharmaceutically acceptable salts thereof.
17. A compound selected from the group consisting of:
| ER # | Structure |
|---|---|
| ER 813081 | 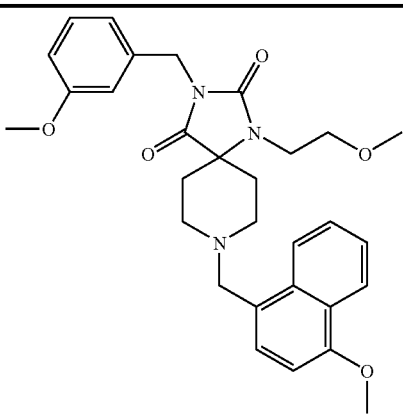 |
| ER 813077 | 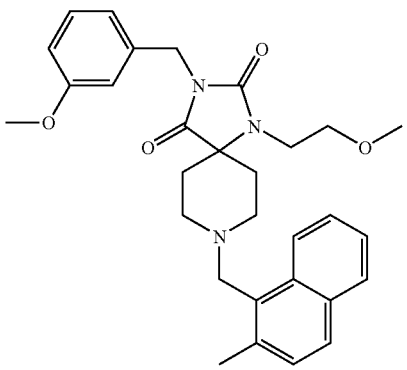 |

201
-continued
| ER # | Structure |
|---|---|
| ER 818528 | 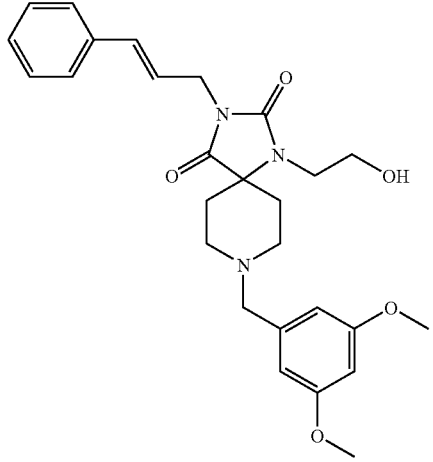 |
| ER 818574 | 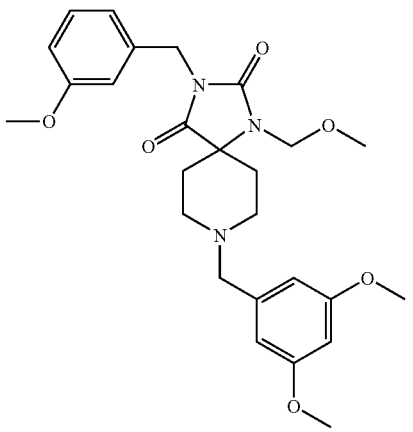 |
| ER 813411 | 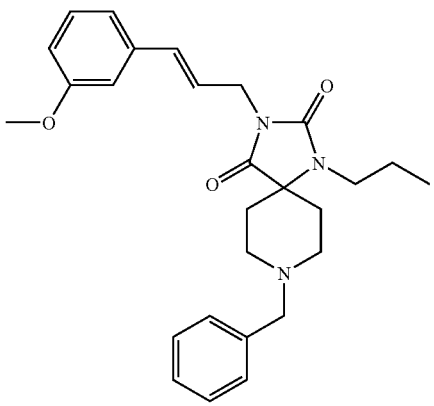 |
202
-continued
| ER # | Structure |
|---|---|
| ER 813078 | 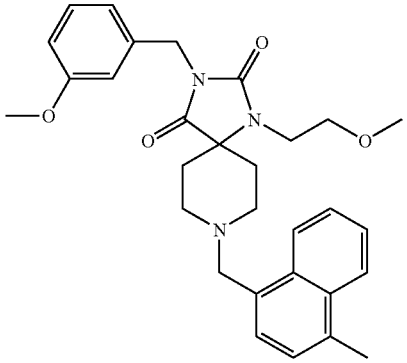 |
| ER 813521 | 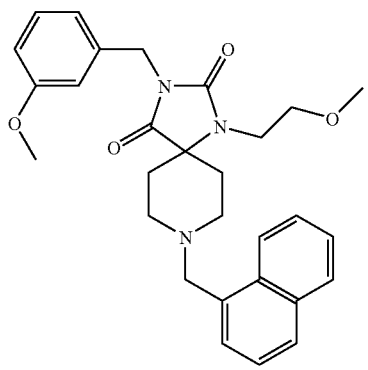 |
| ER 817116 | 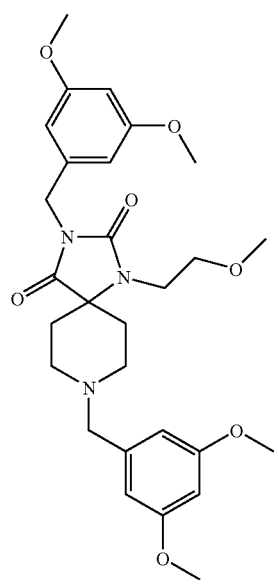 |

| ER # | Structure |
|---|---|
| ER 813080 | 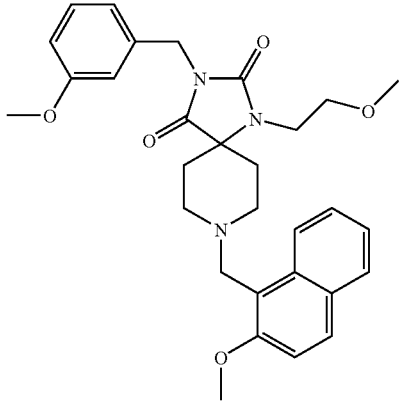 |
| ER 813519 | 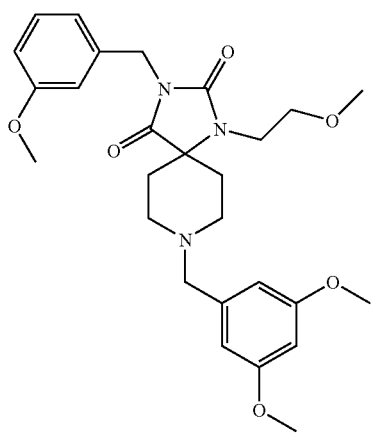 |
| ER 813492 | 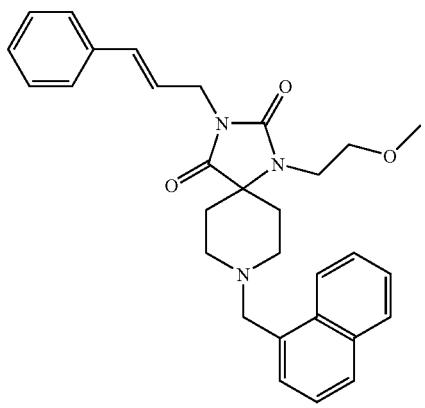 |
| ER # | Structure |
|---|---|
| ER 813452 | 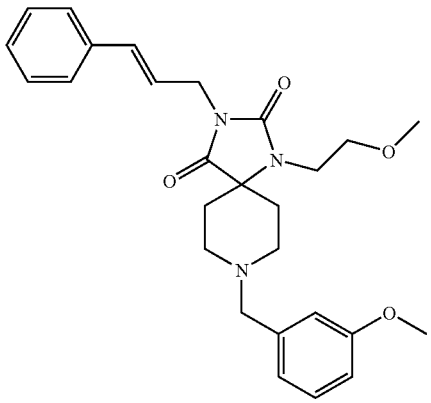 |
| ER 813410 | 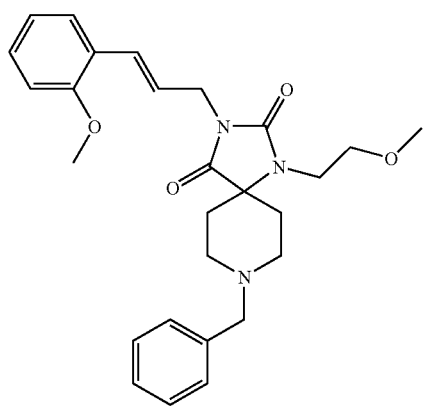 |
| ER 812605 | 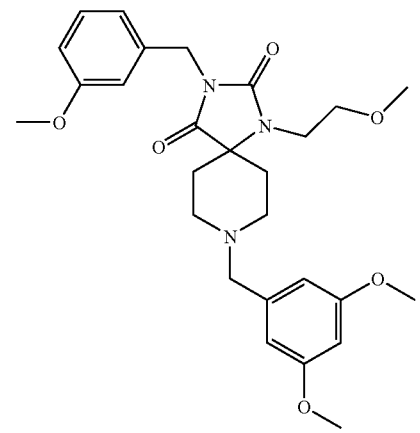 |
and pharmaceutically acceptable salts thereof.

18. A compound selected from the group consisting of:

| ER # | Structure |
|---|---|
| ER 818568 | 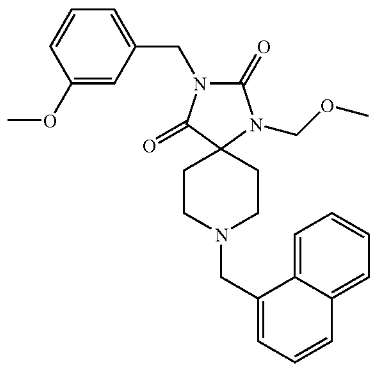 |
| ER 813091 | 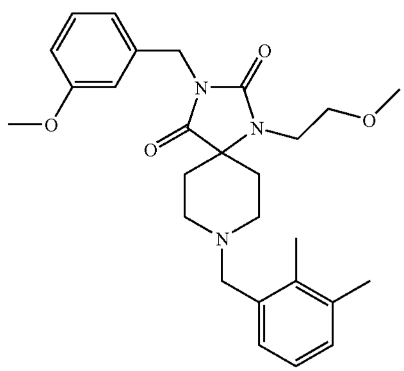 |
| ER 813075 | 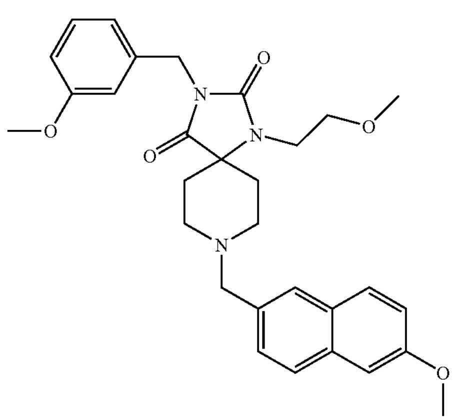 |

-continued

| ER # | Structure |
|---|---|
| ER 818562 | 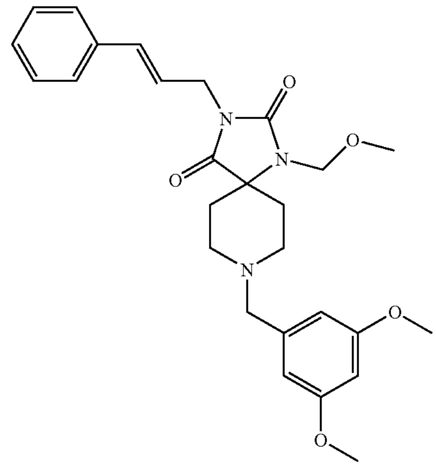 |
| ER 813096 | 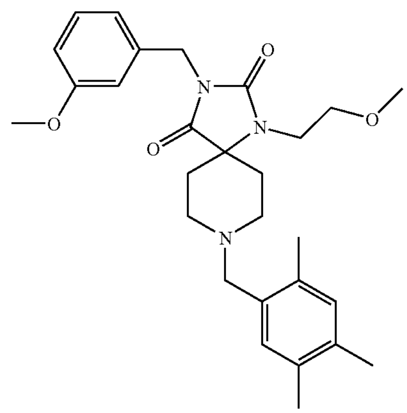 |
| ER 819695 | 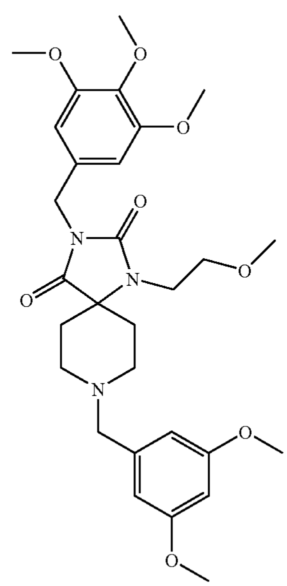 |

-continued
| ER # | Structure |
|---|---|
| ER 813092 | 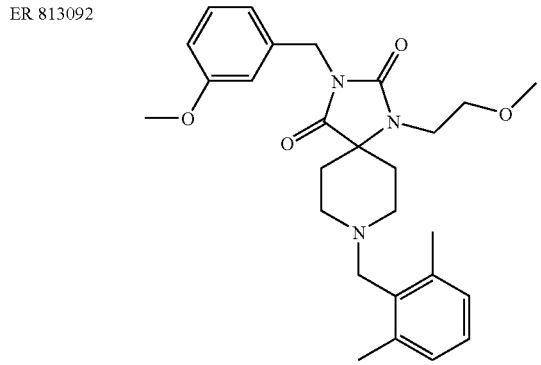 |
| ER 813082 | 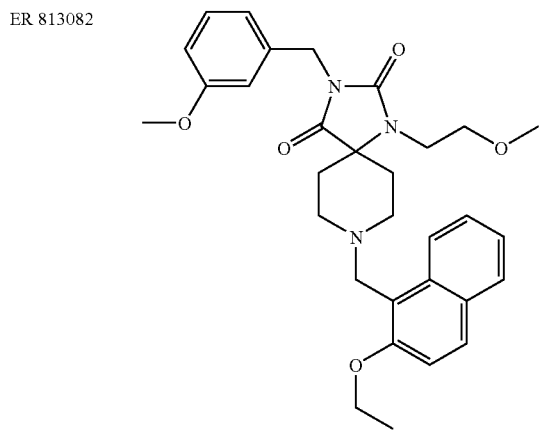 |
| ER 820087 | 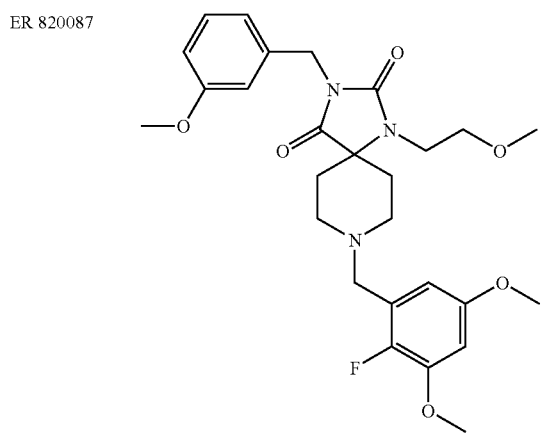 |
| ER 813079 | 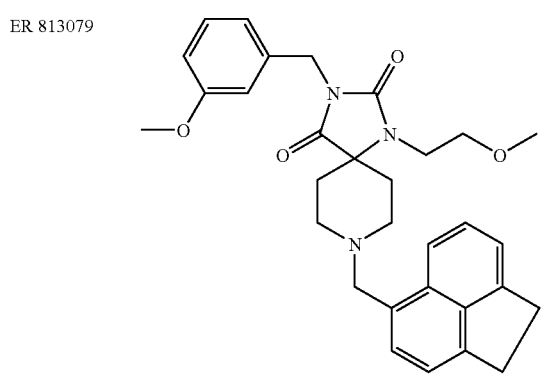 |
-continued
| ER # | Structure |
|---|---|
| ER 813089 | 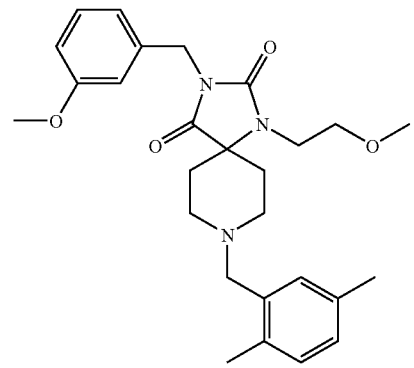 |
| ER 813529 | 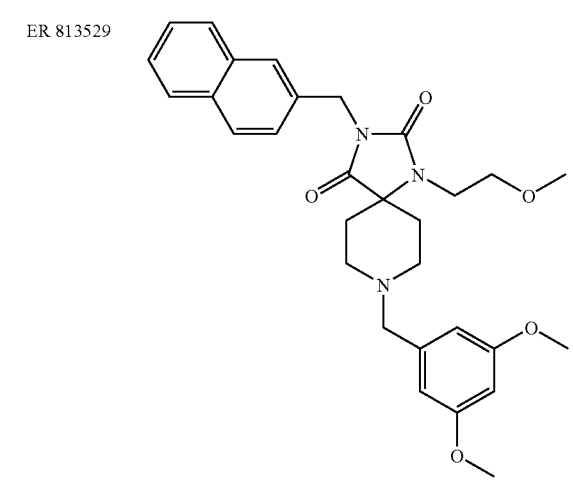 |
| ER 813414 | 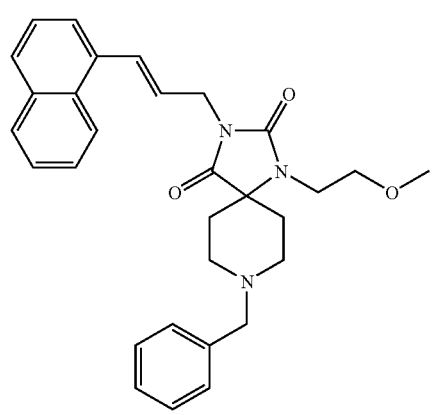 |

-continued
| ER # | Structure |
|---|---|
| ER 813516 | 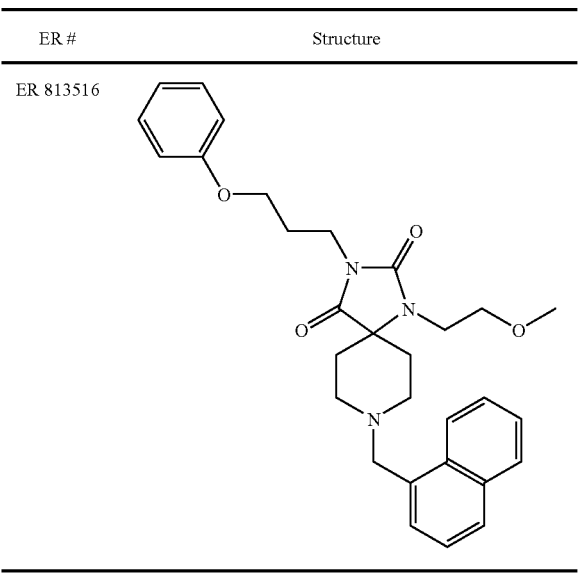 |
and pharmaceutically acceptable salts thereof.
19. A compound selected from the group consisting of:
| ER # | Structure |
|---|---|
| ER 818558 | 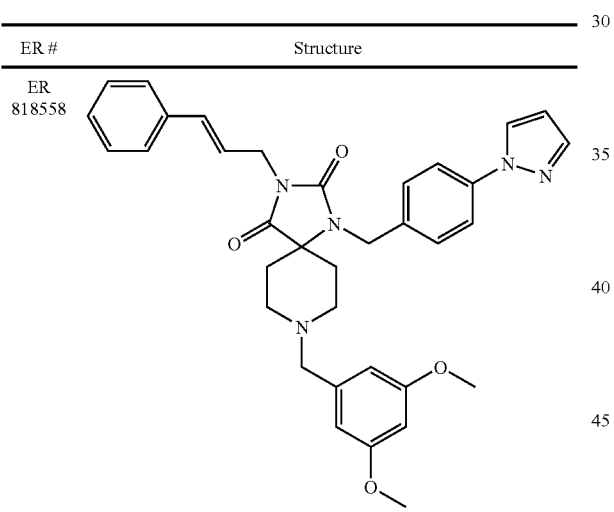 |
| ER 818559 | 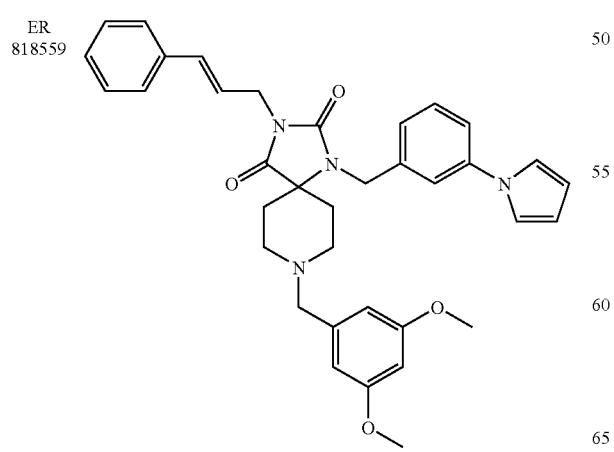 |
-continued
| ER # | Structure |
|---|---|
| ER 818560 | 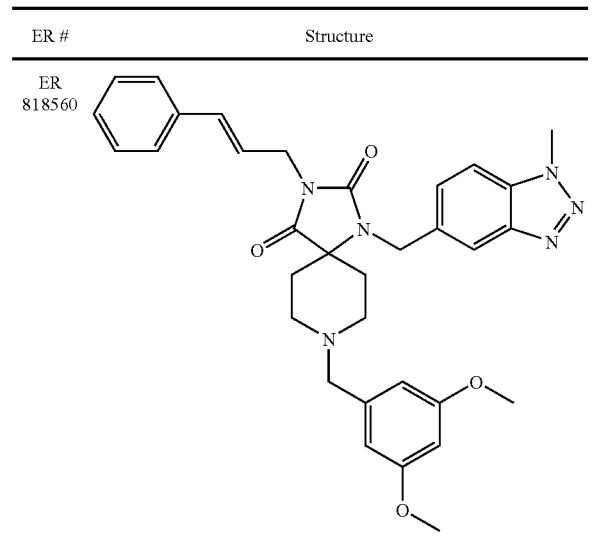 |
| ER 818554 | 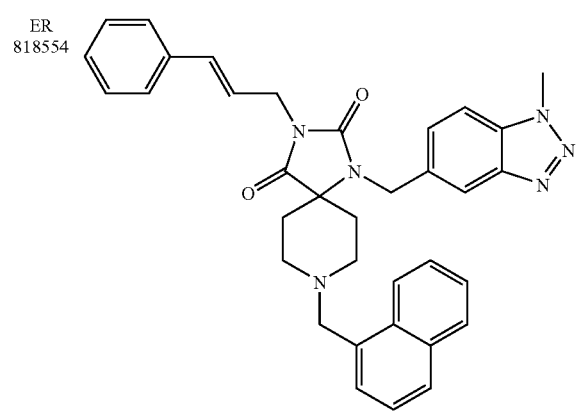 |
| ER 818535 | 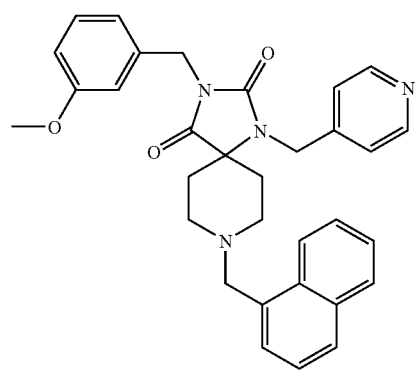 |

-continued

| ER # | Structure |
|---|---|
| ER 818564 | |
| ER 818524 | |
| ER 817117 | | and pharmaceutically acceptable salts thereof.

20. A compound of formula II:

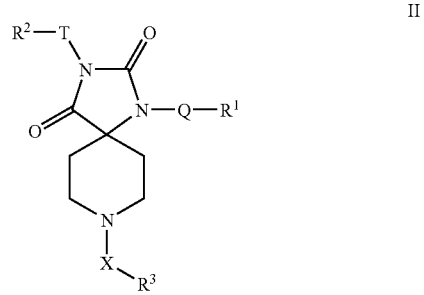

II wherein:
Q is a straight or branched, saturated or unsaturated $C_{1-6}$ alkylene chain;
$R^1$ is an substituted phenyl ring or an optionally substituted 6-membered heteroaryl ring having 1-2 nitrogens;
T is a straight or branched, saturated or unsaturated $C_{1-6}$ alkylene chain;
$R^2$ is an optionally substituted phenyl or naphthyl ring, or an optionally substituted 5-membered heteroaryl ring having 1-3 heteroatoms independently selected from nitrogen, oxygen, and sulfur;
X is methylene, ethylene, or propenylene; and
$R^3$ is phenyl or naphthyl; wherein $R^3$ is optionally substituted with pyrrolidinyl, morpholinyl, piperidinyl, furyl, thienyl, phenyl, —N(Me)phenyl, dimethylamino, methoxy, ethoxy, methyl, t-butyl, pyridyl, -methylamino, —C(=O)OMe, C(=O)OCH$_2$phenyl, amino, hydroxyl, hydroxyethoxy, trifluoromethoxy, trifluoromethyl, or —SO$_2$phenyl;
or a pharmaceutically acceptable salt, thereof.

21. A compound of formula III:

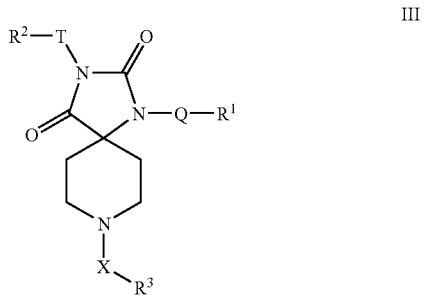

III wherein:
Q is —CH$_2$O—, (CH$_2$)$_2$O—, —(CH$_2$)$_3$O—, (CH$_2$)$_4$O—, —(CH$_2$)$_6$O—, —CH$_2$OCH$_2$—, —(CH$_2$)$_2$OCH$_2$—, —(CH$_2$)$_3$OCH$_2$—, —(CH$_2$)$_4$OCH$_2$—, —(CH$_2$)$_6$OCH$_2$—, —(CH$_2$)$_2$S—, —CH$_2$—, —(CH$_2$)$_2$—, —(CH$_2$)$_3$—, —(CH$_2$)$_4$—, —CH$_2$CH=CH—, —CH$_2$C(=CH$_2$)CH$_2$—, —CH$_2$CH$_2$CH=CH—, —CH$_2$CH(CH$_3$)CH$_2$—, —CH$_2$C(=O)OCH$_2$—, CH$_2$CH=C(CH$_3$)CH$_2$CH$_2$CH=C(CH$_3$)—, —CH$_2$C≡CCH$_2$CH$_2$—, —CH$_2$C(=O)CH$_2$—, (CH$_2$)$_4$C(=O)OCH$_2$CH$_2$—, —(CH$_2$)$_5$C(=O)OCH$_2$CH$_2$—, —(CH$_2$)$_6$C(=O)OCH$_2$CH$_2$—CH$_2$C(=O)N(Et)CH$_2$CH$_2$—, or —CH$_2$CH$_2$N(CH$_3$)CH$_2$—;
$R^1$ is CN, pyridyl, thiazolyl, tetrahydrofuranyl, tetrahydro-2H-pyranyl, phenyl, isoxazolyl, pyrrolyl, benztriazolyl, cyclohexyl, cyclopropyl, or thienyl;

T is —CH₂O—, —(CH₂)₂O—, —(CH₂)₃O—, —(CH₂)₄O—, —(CH₂)₆O—, —CH₂OCH₂—, —(CH₂)₂OCH₂—, —(CH₂)₃OCH₂—, —(CH₂)₄OCH₂—, —(CH₂)₆OCH₂—, —(CH₂)₂S—, —CH₂—, —(CH₂)₂—, —(CH₂)₃—, —(CH₂)₄—, —CH₂CH=CH—, —CH₂CH=CHCH₂—, —CH₂C(=CH₂)CH₂—, —CH₂CH₂CH=CH—, —CH₂CH(CH₃)CH₂—, —CH₂C(=O)OCH₂—, —CH₂CH=C(CH₃)CH₂CH₂CH=C(CH₃)—, —CH₂C≡C— or —CH₂C≡CCH₂—;

R² is optionally substituted phenyl, naphthyl, quinolinyl, phthalimidyl, isoquinolinyl, indolyl, thienyl, furyl, isoxazolyl, or thiazolyl;

X is —CH₂—, —CH₂CH₂—, or —CH₂CH=CH—; and

R³ is phenyl or naphthyl; wherein R³ is optionally substituted with pyrrolidinyl, morpholinyl, piperidinyl, furyl, thienyl, phenyl, —N(Me)phenyl, dimethylamino, methoxy, ethoxy, methyl, t-butyl, pyridyl, methylamino, —C(=O)OMe, —C(=O)OCH₂phenyl, amino, hydroxyl, hydroxyethoxy, trifluoromethoxy, trifluoromethyl, or —SO₂phenyl;

or a pharmaceutically acceptable salt, thereof.

22. A compound of formula IV:

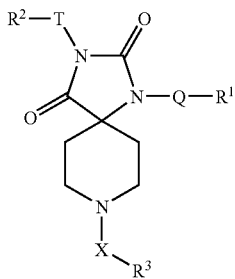

IV wherein:

Q is —CH₂O—, —(CH₂)₂O—, —(CH₂)₃O—, —(CH₂)₄O—, —(CH₂)₆O—, —CH₂OCH₂—, —(CH₂)₂OCH₂—, —(CH₂)₃OCH₂—, —(CH₂)₄OCH₂—, —(CH₂)₆OCH₂—, or

R¹ is hydrogen;

T is —CH₂—, —(CH₂)₂—, —(CH₂)₃—, —(CH₂)₄—, —CH₂CH=CH—, —CH₂CH=CHCH₂—, —CH₂C(=CH₂)CH₂—, —CH₂CH₂CH=CH—, —CH₂CH(CH₃)CH₂—, —CH₂C(=O)OCH₂—, —CH₂CH=C(CH₃)CH₂CH₂CH=C(CH₃)—, —CH₂C≡C— or CH₂C≡CCH₂—;

R² is optionally substituted phenyl or naphthyl;

X is —CH₂—; and

R³ is a phenyl or naphthyl ring; wherein R³ is optionally substituted with pyrrolidinyl, morpholinyl, piperidinyl, furyl, thienyl, phenyl, —N(Me)phenyl, dimethylamino, methoxy, ethoxy, methyl, t-butyl, pyridyl, —NHMe, —C(=O)OMe, —C(=O)OCH₂phenyl, amino, hydroxyl, hydroxyethoxy, trifluoromethoxy, trifluoromethyl, or —SO₂phenyl;

or a pharmaceutically acceptable salt thereof.

23. A pharmaceutical composition comprising a compound of claim 1, 14, 15, 16, 17, 18, or 19.

24. A method for treating rheumatoid arthritis in a patient, comprising the step of administering to a patient in need of treatment a pharmaceutical composition comprising a compound of claim 1.

25. A method for treating multiple sclerosis in a patient, comprising the step of administering to a patient in need of treatment a pharmaceutical composition comprising a compound of claim 1.

26. A method for treating an autoimmune disease, comprising the step of administering to a patient in need of treatment a pharmaceutical composition comprising a compound of claim 1.

27. The method of claim 26, wherein said autoimmune disease is selected from the group consisting of Crohn's disease, rheumatoid arthritis, multiple sclerosis, systemic lupus erythematosus, type I diabetes mellitus, HTLV-1-associated myelopathy/tropical spastic paraparesis, artherosclerosis, Hodgkin's Lymphoma, B-cell lymphoblastic leukemia/lymphoblastic lymphoma, chronic lymphocytic leukemia, marginal zone lymphoma, and hairy cell leukemia, Behcet's disease, Coeliac disease, and T-cell-mediated liver inflammation.

28. The method of claim 26, wherein said autoimmune disease is inflammatory bowel disease.

29. The compound of claim 1, wherein R¹ is C₁₋₆ alkoxy.

30. The compound of claim 1, wherein X is propenylene.

* * * * *

UNITED STATES PATENT AND TRADEMARK OFFICE
CERTIFICATE OF CORRECTION

| | | |
|---|---|---|
| PATENT NO. | : 7,666,875 B2 | Page 1 of 1 |
| APPLICATION NO. | : 11/441950 | |
| DATED | : February 23, 2010 | |
| INVENTOR(S) | : Gallagher, Jr. et al. | |

It is certified that error appears in the above-identified patent and that said Letters Patent is hereby corrected as shown below:

In the Claims:
Column 195, Claim 15, Line 26: Please correct "$R^7$" to read -- $R^2$ --
            Line 37: Please correct "$R^7$" to read -- $R^3$ --

Column 197, Claim 16, Compound ER 813493: Please correct

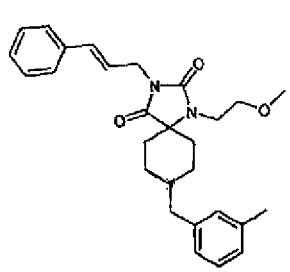    to read    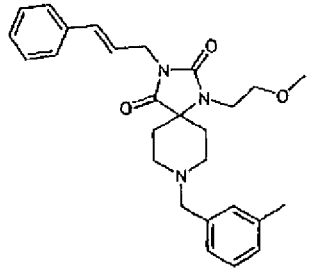

Column 212, Claim 20, Line 20: Please correct "is an substituted" to read
            -- is an optionally substituted --
        Line 29: Please delete the word "optionally" which follows "$R^3$ is"

Column 212, Claim 21, Line 53: Please correct "(CH$_2$)$_2$O—" to read
            -- —(CH$_2$)$_2$O— --
        Line 53: Please correct "(CH$_2$)$_4$O—" to read
            -- —(CH$_2$)$_4$O— --
        Line 59: Please correct "CH$_2$CH=C" to read
            -- —CH$_2$CH=C --
        Line 61: Please correct "(CH$_2$)$_4$C(=O)" to read
            -- —(CH$_2$)$_4$C(=O) --

Column 213, Claim 22, Line 42: Please correct ", or" to read
            -- , or —(CH$_2$)$_2$S --

Signed and Sealed this
Eighth Day of March, 2011

David J. Kappos
*Director of the United States Patent and Trademark Office*